United States Patent
Davis et al.

(10) Patent No.: US 10,406,287 B2
(45) Date of Patent: *Sep. 10, 2019

(54) SYSTEM AND METHOD FOR PROVIDING ALERTS OPTIMIZED FOR A USER

(71) Applicant: DexCom, Inc., San Diego, CA (US)

(72) Inventors: Anna Leigh Davis, Cardiff by the Sea, CA (US); Scott M. Belliveau, San Diego, CA (US); Naresh C. Bhavaraju, San Diego, CA (US); Leif N. Bowman, San Diego, CA (US);

(Continued)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,476

(22) Filed: Jul. 6, 2018

(65) Prior Publication Data

US 2018/0326150 A1 Nov. 15, 2018

Related U.S. Application Data

(63) Continuation of application No. 15/582,467, filed on Apr. 28, 2017, now Pat. No. 10,052,073, which is a (Continued)

(51) Int. Cl.
*A61M 5/172* (2006.01)
*G16H 50/20* (2018.01)
(Continued)

(52) U.S. Cl.
CPC ......... *A61M 5/1723* (2013.01); *A61B 5/0022* (2013.01); *A61B 5/024* (2013.01);
(Continued)

(58) Field of Classification Search
None
See application file for complete search history.

(56) References Cited

U.S. PATENT DOCUMENTS 6,653,930 B1 * 11/2003 Bonomo ............... H04M 19/04
340/7.21
6,923,763 B1 8/2005 Kovatchev et al.
(Continued)

FOREIGN PATENT DOCUMENTS

WO  WO 2005-082436  9/2005
WO  WO 2007-149533  12/2007
(Continued)

OTHER PUBLICATIONS

Ambrosiadou et al. 1996. Computer Methods and Programs in Biomedicine 49:105-115. Clinical evaluation of the Diabetes expert system for decision support by multiple regimen.
(Continued)

*Primary Examiner* — Curtis J King
(74) *Attorney, Agent, or Firm* — Knobbe Martens Olson & Bear, LLP

(57) ABSTRACT

Systems and methods are disclosed that provide smart alerts to users, e.g., alerts to users about diabetic states that are only provided when it makes sense to do so, e.g., when the system can predict or estimate that the user is not already cognitively aware of their current condition, e.g., particularly where the current condition is a diabetic state warranting attention. In this way, the alert or alarm is personalized and made particularly effective for that user. Such systems and methods still alert the user when action is necessary, e.g., a bolus or temporary basal rate change, or provide a response to a missed bolus or a need for correction, but do not alert when action is unnecessary, e.g., if the user is already estimated or predicted to be cognitively aware of the
(Continued)

diabetic state warranting attention, or if corrective action was already taken.

17 Claims, 29 Drawing Sheets

(72) Inventors: Rita M. Castillo, Ramona, CA (US); Alexandra Elena Constantin, San Diego, CA (US); Rian Draeger, San Diego, CA (US); Laura J. Dunn, San Diego, CA (US); Gary Brian Gable, Boise, ID (US); Arturo Garcia, Chula Vista, CA (US); Thomas Hall, San Diego, CA (US); Hari Hampapuram, Portland, OR (US); Christopher Robert Hannemann, San Diego, CA (US); Anna Claire Harley-Trochimczyk, San Diego, CA (US); Nathaniel David Heintzman, San Diego, CA (US); Andrea J. Jackson, Solana Beach, CA (US); Lauren Hruby Jepson, San Diego, CA (US); Apurv Ullas Kamath, San Diego, CA (US); Katherine Yerre Koehler, Solana Beach, CA (US); Aditya Sagar Mandapaka, San Diego, CA (US); Samuel Jere Marsh, San Diego, CA (US); Gary A. Morris, La Jolla, CA (US); Subrai Girish Pai, San Diego, CA (US); Andrew Attila Pal, San Diego, CA (US); Nicholas Polytaridis, San Diego, CA (US); Philip Thomas Pupa, San Diego, CA (US); Eli Reihman, San Diego, CA (US); Ashley Anne Rindfleisch, San Diego, CA (US); Sofie Wells Schunk, San Diego, CA (US); Peter C. Simpson, Cardiff, CA (US); Daniel Smith, San Diego, CA (US); Stephen J. Vanslyke, San Diego, CA (US); Matthew T. Vogel, Encinitas, CA (US); Tomas C. Walker, Henderson, NV (US); Benjamin Elrod West, San Diego, CA (US); Atiim Joseph Wiley, San Diego, CA (US)

Related U.S. Application Data continuation of application No. 15/582,057, filed on Apr. 28, 2017.

(60) Provisional application No. 62/330,729, filed on May 2, 2016.

(51) Int. Cl.
| | | |
|---|---|---|
| G06N 20/00 | (2019.01) | |
| A61B 5/024 | (2006.01) | |
| A61B 5/11 | (2006.01) | |
| A61B 5/145 | (2006.01) | |
| A61B 5/16 | (2006.01) | |
| A61B 5/00 | (2006.01) | |
| G06F 19/00 | (2018.01) | |
| G08B 21/04 | (2006.01) | |
| H04M 1/725 | (2006.01) | |
| G06N 5/04 | (2006.01) | |
| G16H 20/17 | (2018.01) | |
| G16H 40/67 | (2018.01) | |
| G16H 40/63 | (2018.01) | |

(52) U.S. Cl.
CPC ........ *A61B 5/1112* (2013.01); *A61B 5/14517* (2013.01); *A61B 5/14532* (2013.01); *A61B 5/14546* (2013.01); *A61B 5/165* (2013.01); *A61B 5/4866* (2013.01); *A61B 5/742* (2013.01); *A61B 5/746* (2013.01); *G06F 19/00* (2013.01); *G06F 19/3418* (2013.01); *G06F 19/3468* (2013.01); *G06N 5/043* (2013.01); *G06N 20/00* (2019.01); *G08B 21/0453* (2013.01); *G16H 20/17* (2018.01); *G16H 40/63* (2018.01); *G16H 40/67* (2018.01); *G16H 50/20* (2018.01); *H04M 1/7253* (2013.01); *A61M 2205/18* (2013.01); *A61M 2205/3584* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/8206* (2013.01); *A61M 2230/201* (2013.01); *Y02A 90/26* (2018.01)

(56) References Cited

U.S. PATENT DOCUMENTS

| | | | |
|---|---|---|---|
| 7,022,072 | B2 | 4/2006 | Fox et al. |
| 7,025,425 | B2 | 4/2006 | Kovatchev et al. |
| 7,052,472 | B1 * | 5/2006 | Miller ............... A61B 5/01 600/549 |
| 7,137,951 | B2 | 11/2006 | Pilarski |
| 7,261,691 | B1 | 8/2007 | Asomani |
| 7,344,251 | B2 | 3/2008 | Marshall |
| 7,384,396 | B2 | 6/2008 | Samuels et al. |
| 7,438,418 | B2 | 10/2008 | Marshall |
| 7,591,801 | B2 | 9/2009 | Brauker et al. |
| 7,727,147 | B1 * | 6/2010 | Osorio ............... A61B 5/14528 600/345 |
| 7,768,386 | B2 | 8/2010 | Hayter et al. |
| 7,874,985 | B2 | 1/2011 | Kovatchev et al. |
| 7,905,832 | B1 | 3/2011 | Lau et al. |
| 7,988,630 | B1 | 8/2011 | Osorio et al. |
| 8,226,556 | B2 | 7/2012 | Hayes et al. |
| 8,269,634 | B2 | 9/2012 | Fischell et al. |
| 8,290,562 | B2 | 10/2012 | Goode et al. |
| 8,301,231 | B2 | 10/2012 | Fischell et al. |
| 8,514,086 | B2 | 8/2013 | Harper et al. |
| 8,538,703 | B2 | 9/2013 | Kovatchev et al. |
| 8,548,544 | B2 | 10/2013 | Kircher et al. |
| 8,562,587 | B2 | 10/2013 | Kovatchev et al. |
| 8,585,593 | B2 | 11/2013 | Kovatchev et al. |
| 8,589,082 | B2 | 11/2013 | Chakrabarty et al. |
| 8,798,934 | B2 | 8/2014 | Wei et al. |
| 8,808,228 | B2 | 8/2014 | Brister et al. |
| 8,884,767 | B2 | 11/2014 | Kidmore |
| 8,922,352 | B2 | 12/2014 | Tsui et al. |
| 8,930,222 | B2 | 1/2015 | Rhine-Pallas et al. |
| 8,930,290 | B2 | 1/2015 | Cragun et al. |
| 8,954,373 | B2 | 2/2015 | Atlas et al. |
| 8,974,385 | B2 | 3/2015 | Lee et al. |
| 8,974,746 | B2 | 3/2015 | Matsumura |
| 8,992,475 | B2 | 3/2015 | Mann et al. |
| 9,041,730 | B2 | 5/2015 | Johnson et al. |
| 9,076,317 | B2 | 7/2015 | Nothacker et al. |
| 9,119,528 | B2 | 9/2015 | Cobelli et al. |
| 9,135,402 | B2 | 9/2015 | Mensinger et al. |
| 9,330,237 | B2 | 5/2016 | Cohen et al. |
| 9,386,522 | B2 | 7/2016 | San Vicente et al. |
| 9,398,869 | B2 | 7/2016 | Kovatchev et al. |
| 9,430,022 | B2 | 8/2016 | Kovatchev et al. |
| 9,439,602 | B2 | 9/2016 | Sparacino et al. |
| 9,446,194 | B2 | 9/2016 | Kamath et al. |
| 9,579,456 | B2 | 2/2017 | Budiman et al. |
| 9,622,691 | B2 | 4/2017 | Budiman |

(56) References Cited

U.S. PATENT DOCUMENTS

| | | |
|---|---|---|
| 9,730,621 B2 | 8/2017 | Cohen et al. |
| 2003/0125612 A1* | 7/2003 | Fox .................... A61B 5/14532 600/347 |
| 2003/0191376 A1* | 10/2003 | Samuels ................ A61B 5/00 600/309 |
| 2003/0195404 A1 | 10/2003 | Knobbe et al. |
| 2005/0027182 A1* | 2/2005 | Siddiqui ............ A61B 5/14532 600/365 |
| 2006/0203197 A1* | 9/2006 | Marshall ................ A61B 3/112 351/246 |
| 2007/0291232 A1* | 12/2007 | Marshall ................ A61B 5/16 351/246 |
| 2008/0071157 A1 | 3/2008 | McGarraugh |
| 2008/0154513 A1 | 6/2008 | Kovatchev et al. |
| 2008/0220403 A1 | 9/2008 | Marling |
| 2009/0082692 A1* | 3/2009 | Hale .................... A61B 5/0476 600/544 |
| 2009/0143725 A1 | 6/2009 | Peyser et al. |
| 2009/0171589 A1 | 7/2009 | Kovatchev |
| 2010/0138203 A1 | 6/2010 | Alferness et al. |
| 2010/0174553 A1* | 7/2010 | Kaufman ............ A61B 5/14532 705/2 |
| 2010/0179768 A1 | 7/2010 | Kovatchev et al. |
| 2010/0198520 A1 | 8/2010 | Breton et al. |
| 2010/0249561 A1 | 9/2010 | Patek et al. |
| 2010/0261987 A1 | 10/2010 | Kamath et al. |
| 2010/0292634 A1 | 11/2010 | Kircher et al. |
| 2010/0302042 A1* | 12/2010 | Barnett ................ G08B 19/00 340/573.1 |
| 2010/0324932 A1 | 12/2010 | Galley et al. |
| 2011/0054264 A1* | 3/2011 | Fischell ................ A61B 5/0031 600/300 |
| 2011/0054334 A1* | 3/2011 | Fischell ................ A61B 5/0402 600/509 |
| 2011/0118578 A1 | 5/2011 | Timmerman |
| 2011/0193704 A1 | 8/2011 | Harper et al. |
| 2012/0004512 A1 | 1/2012 | Kovatchev et al. |
| 2012/0078067 A1 | 3/2012 | Kovatchev et al. |
| 2012/0123234 A1 | 5/2012 | Atlas et al. |
| 2012/0231431 A1 | 9/2012 | Angelides |
| 2012/0235820 A1* | 9/2012 | Kidmose .............. A61B 5/0006 340/573.1 |
| 2012/0245556 A1 | 9/2012 | Kovatchev et al. |
| 2013/0011819 A1* | 1/2013 | Horseman ............ A61B 5/6887 434/257 |
| 2013/0035563 A1 | 2/2013 | Angelides |
| 2013/0035871 A1* | 2/2013 | Mayou ................ A61B 5/14532 702/26 |
| 2013/0072765 A1 | 3/2013 | Kahn et al. |
| 2013/0116649 A1 | 5/2013 | Breton et al. |
| 2013/0282302 A1 | 10/2013 | Harper |
| 2013/0307686 A1 | 11/2013 | Frauenthal et al. |
| 2014/0006322 A1* | 1/2014 | Cragun .................... G06N 5/04 706/14 |
| 2014/0031786 A1 | 1/2014 | Kircher et al. |
| 2014/0039383 A1 | 2/2014 | Dobbles et al. |
| 2014/0046159 A1 | 2/2014 | Kovatchev et al. |
| 2014/0066889 A1 | 3/2014 | Grosman et al. |
| 2014/0088398 A1 | 3/2014 | Bernstein et al. |
| 2014/0118138 A1* | 5/2014 | Cobelli ................ A61B 5/0022 340/539.12 |
| 2014/0118166 A1 | 5/2014 | Hampapuram et al. |
| 2014/0128803 A1 | 5/2014 | Dobbles et al. |
| 2014/0184422 A1* | 7/2014 | Mensinger ............ A61B 5/0004 340/870.02 |
| 2014/0188398 A1* | 7/2014 | Cohen ................ A61B 5/14532 702/19 |
| 2014/0200559 A1* | 7/2014 | Doyle, III ............ A61M 5/1723 604/891.1 |
| 2014/0243637 A1* | 8/2014 | Rahman ................ A61B 5/0008 600/365 |
| 2014/0253323 A1 | 9/2014 | Berven |
| 2014/0276238 A1* | 9/2014 | Osorio ................ A61B 5/0205 600/595 |
| 2014/0288494 A1 | 9/2014 | Brister et al. |
| 2014/0324800 A1 | 10/2014 | Soni et al. |
| 2014/0361900 A1* | 12/2014 | Nothacker ............ G08B 21/02 340/576 |
| 2015/0018633 A1 | 1/2015 | Kovatchev et al. |
| 2015/0118658 A1 | 4/2015 | Mayou et al. |
| 2015/0118668 A1 | 4/2015 | Mayou et al. |
| 2015/0119655 A1 | 4/2015 | Mayou et al. |
| 2015/0119667 A1* | 4/2015 | Reihman ............ A61B 5/6802 600/365 |
| 2015/0119668 A1 | 4/2015 | Mayou et al. |
| 2015/0120317 A1 | 4/2015 | Mayou et al. |
| 2015/0123810 A1 | 5/2015 | Hernandez-Rosas et al. |
| 2015/0134356 A1 | 5/2015 | Atlas et al. |
| 2015/0164390 A1 | 6/2015 | Larvenz et al. |
| 2015/0190098 A1 | 7/2015 | Patek et al. |
| 2015/0190100 A1* | 7/2015 | Fox .................... G16H 40/63 340/539.12 |
| 2015/0208975 A1* | 7/2015 | Ghajar ................ A61B 5/16 600/595 |
| 2015/0250429 A1 | 9/2015 | Hampapuram et al. |
| 2015/0289821 A1 | 10/2015 | Rack-Gomer et al. |
| 2015/0289823 A1* | 10/2015 | Rack-Gomer ......... G16H 40/63 600/365 |
| 2015/0324520 A1 | 11/2015 | Aykroyd et al. |
| 2016/0004813 A1 | 1/2016 | Kovatchev et al. |
| 2016/0081597 A1* | 3/2016 | Bhavaraju ............ A61B 5/1495 600/365 |
| 2016/0171183 A1 | 6/2016 | Breton et al. |
| 2016/0174911 A1 | 6/2016 | Palerm et al. |
| 2016/0213290 A1 | 7/2016 | Park et al. |
| 2016/0328991 A1* | 11/2016 | Simpson ................ A61B 5/742 |
| 2016/0331310 A1 | 11/2016 | Kovatchev et al. |
| 2017/0049386 A1 | 2/2017 | Abraham et al. |
| 2017/0056591 A1 | 3/2017 | Breton et al. |
| 2017/0132120 A1* | 5/2017 | Salameh ................ H04W 4/70 |
| 2017/0147769 A1 | 5/2017 | Bernstein et al. |
| 2017/0177825 A1* | 6/2017 | Wolpert ............. A61B 5/0022 |
| 2017/0185953 A1* | 6/2017 | Dalforno ............. G06Q 10/087 |
| 2017/0220750 A1 | 8/2017 | Davis et al. |
| 2017/0293732 A1 | 10/2017 | Cohen et al. |
| 2017/0311903 A1 | 11/2017 | Davis et al. |
| 2018/0353112 A1 | 12/2018 | Dassau et al. |

FOREIGN PATENT DOCUMENTS

| | | |
|---|---|---|
| WO | WO 2008-101172 | 8/2008 |
| WO | WO 2009-048462 | 4/2009 |
| WO | WO 2010-111660 | 9/2010 |
| WO | WO 2012-175181 | 12/2012 |
| WO | WO 2014-011488 | 1/2014 |
| WO | WO 2015-026579 | 2/2015 |
| WO | WO 2015-056259 | 4/2015 |
| WO | WO 2015-066051 | 5/2015 |
| WO | WO 2015-187366 | 12/2015 |
| WO | WO 2016-025874 | 2/2016 |
| WO | WO 2016-133879 | 8/2016 |
| WO | WO 2016-201120 | 12/2016 |
| WO | WO 2017-040927 | 3/2017 |
| WO | WO 2017-132663 | 8/2017 |

OTHER PUBLICATIONS

Carlson et al. 2013. Association for the Advancement of Artificial Intelligence, The MITRE Corporation Innovation Program, Project 51MS661-CA (Approved for Public Release, Di.

Desai, Junjal 2012, University of Massachusetts Lowell Ph.D. Thesis. Modeling Trust to Improve Human-Robot Interaction. [225 pages].

Glorennec et al. 1995. Predictive Fuzzy Model of Glycaemic Variations, pp. 411-420 in Fuzzy Logic and Soft Computing.

Herrero et al. 2012. J. Diabetes Science and Technology 6(5):1131-1141. Robust Fault Detection System for Insulin Pump Therapy Using Continuous Glucose Monitoring.

(56) References Cited

OTHER PUBLICATIONS http://www.wired.com/2014/06/trust-robots-2/, Printed Mar. 4, 2015. You Should Learn to Trust your Robots. It's for Your Own Good.
Lee & See 2004. Human Factors 46(1):50-80. Trust in Automation: Designing for Appropriate Reliance.
Lee, John D. 2008. Human Factors 50(3):404-410. Review of Pivotal Human Factors Article: "Humans and Automation: Use, Misuse, Disuse, Abuse."
Parasuraman 1997. Human Factors 39(2):230-253. Humans and Automation: Use, Misuse, Disuse, Abuse.
Pesl et al. Feb. 2014. A Mobile-Based Advanced Bolus Calculator for Diabetes Management. (Poster) Imperiod Collegel London, UK.
Reddy et al. 2015. Clinical Safety Evaluation of an Advanced Bolus Calculator for Type 1 Diabetes (ABC4D) (poster). Imperiod College of London, UK.
Reddy et al. Feb. 2015. J. Diabetes Technology & Therapeutics 17:A129-A130 (poster & abstract). Clinical Safety Evaluation of an Advanced Bolus Calculator for Type 1 Diabetes.
Scheiner 2015. Practical CGM: A Guide to Improving Outcomes through Continuous Glucose Monitoring. Chapter 2, pp. 17-34, American Diabetes Association, Inc., Alexandra, VA.
Scott 2014. SMBG Bolus Calculator Design. Abbott Diabetes Care presentation.
Stadelmann et al. 1990. Computer Methods and Programs in Biomedicine 32:333-337, DIABETEX decision module 2—calculation of insulin dose proposals and situation recognition.
Walsh 2014. J. Diabetes Science and Technology 8(1):170-178. Confusion Regarding Duration of Insulin Action: A Potential Source for Major Insulin Dose Errors by Bolus Calcu.
Benharref et al. 2014. Conf Proc. IEEE Eng. Med. Biol. Soc. 2014:2698-1701. Closing the loop from continuous M-health monitoring to fuzzy logic-based optimized recommendations.
Herrero et al. Apr 2015. Computer Methods and Programs in Biomedicine 119(1):1-8. Method for automatic adjustment of an insulin bolus calculator: In silico robustness evaluation under intra-day variability.
Herrero et al. Apr. 2013. DOI 10.1109/JBHI.2014.2331896, IEEE Journal of Biomedical and Health Informatics. Advanced Insulin Bolus Advisor based on Run-to-Run Control and Case-Based Reasoning.
Herrero et al. Feb. 2015 (pre-pubn). Comput. Methods Programs Biomed. (2015), http://dx.doi.org/10.1016/j.cmpb.2015.02.003. Method for automatic adjustment of an insulin bolus calculator: in silico robustness evaluation under intra-day variability.
Herrero et al. Jun. 2014 (pre-pubn), Pubn May 2015. IEEE J. Biomed. & Health Inform. 19 (3):1087-1096 (2015). Advanced Insulin Bolus Advisor based on Run-to-Run Control and Case-Based Reasoning.
Hsu et al. 2016. Diabetes Technology and Therapeutics 18:59-68. Utilization of a cloud-based diabetes management program for insulin initiation and titration enables collaborative decision making between healthcare providers and patients.
Parasuraman et al. 2000. IEEE Transactions on Systems, Man and Cybernetics—Part A: Systems and Humans 30(3):286-297. A Model for Types and Levels of Human Interaction with Automation.
Pesl et al. 2015. IEEE J Biomedical and Health Informatics, DOI 10.1109/JBHI.2015.2464088. An Advanced Bolus Calculator for Type 1 Diabetes: System Architecture and Usability Results.
Pesl et al. Aug. 2015 (pre-pubn). IEEE Journal of Biomedical and Health Informatics DOI 10.1109/JBHI.2015.2464088. An Advanced Bolus Calculator for Type 1 Diabetes: System.
Pesl et al. Jan 2016. IEEE Journal of Biomedical and Health Informatics 20(1):11-17. An Advanced Bolus Calculator for Type 1 Diabetes: System Architecture and Usability Results.

* cited by examiner 0 min

SYSTEM AND METHOD FOR PROVIDING ALERTS OPTIMIZED FOR A USER

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/582,467, filed Apr. 28, 2017, which is a continuation of U.S. application Ser. No. 15/582,057, filed Apr. 28, 2017, which claims the benefit of U.S. Provisional Application No. 62/330,729, filed May 2, 2016. Each of the aforementioned applications is incorporated by reference herein in its entirety, and each is hereby expressly made a part of this specification.

FIELD

Alerts for users, particularly in the medical field where physiological parameters are being monitored, are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high glucose, which may cause an array of physiological derangements (for example, kidney failure, skin ulcers, or bleeding into the vitreous of the eye) associated with the deterioration of small blood vessels.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful clinical information, such as glucose expressed in mg/dL.

Where the analyte is glucose, and in the case of continuous glucose monitors (CGM), some CGMs provide for the activation of various alerts or alarms when the user's glucose value enters dangerous or undesired ranges. For example, many CGM's provide alerts if a user's glucose values stray into a range of mild hypoglycemia or hyperglycemia, and alarms if the situation becomes more dire. In some cases, such alerts/alarms use predictive algorithms to determine if the user is approaching a dangerous state and thus if an alert or alarms should be activated.

While useful, such alerts and alarms are not without problems. For example, users can quickly grow used to such alerts and alarms and begin to "tune them out" or otherwise ignore them. In some cases, users are unnecessarily re-alerted to a condition of which they are already aware. In many of these cases, "alert fatigue" can set in, causing the user to either disregard the alert or turn the same off without adequate consideration as to its cause or potential steps to address.

Other problems are now described. Examples will first be given in the category of "high" glucose alerts. In post meal time frames, users are often annoyed when they receive high alerts after eating and subsequent to dosing for a meal. Such high alerts can even occasionally lead to "stacking" or dosing insulin when insulin is already "on board". In such cases, users are receiving alerts that they do not need to take action for, or which can cause users to take unnecessary action. In many cases, responses to such unnecessary post-meal alerts include that the user starts ignoring alerts, sets higher alert thresholds (and thus prevents the user from using a proper threshold as their target range boundary), or in some cases even turning off their high alerts. Such remedies can cause users to miss future unexpected high glucose levels.

Unnecessary re-alerts are another example of a high alert problem. In this case, users are annoyed when they receive multiple high alerts for the same height glucose event. Such situations are often caused by glucose levels hovering above and below their high threshold. In some cases users can activate a "snooze" time, and such as some degree of effectiveness. However, as with post-meal alerts, users do not want to be re-alerted for the same high event before their set snooze time. Remedies for these situations are similar to those above, including that users ignore alerts or turn off their high alert, again missing future unexpected high glucose levels.

Another "high alert" problem includes missed boluses. For example, users often receive a high alert if they have forgotten to dose for a meal. The high alert reminds users to dose, but the same is typically too late and does not prevent further rising. Remedies for missed boluses include that users set lower high alert thresholds, or set a rise rate alert. However, such remedies may result in additional false alerts for the user. In addition, the high alert and rise rate alert are sometimes not effective or accurate enough to catch missed boluses.

Another "high alert" problem is that certain users, e.g., those with a goal of tighter glucose control, want to be alerted if they are close but to below their high threshold for a long period of time. Such users may be using their high alert thresholds for their target zone boundaries, and in such cases, users may be unaware of how to accurately set or change their high alert thresholds.

Other high alert problems include that users do not know how to react to their initial alert settings. Still other high alert problems will also be understood.

Other problems exist in the use of "low alerts". For example, alert fatigue as noted above can lead to mistrust in the system. For example, users may set a higher low alert threshold in order to give themselves more time to prevent severe hypoglycemic events. However, this may lead to more frequent alerts and consequent annoyance. For example, such users may receive many alerts of low blood glucose levels that do not lead to severe lows. While users desire more warnings for severe lows, frequent low alerts at a higher alert threshold cause mistrust in the system.

Relatedly, false alerts caused by faults such as compression may also cause mistrust in the system. In response to alert fatigue, users sometimes set lower alert thresholds, but then they have consequently less time to prevent urgent lows. As another remedy, users may turnoff low alerts and use fall rate alerts or urgent low alerts instead. For example, a fall rate alert may be set at −2 or −3 mg/dL. As yet another remedy, users may turn off their low alerts and rely on urgent low alerts instead. In many of these cases, user responses do not prevent low blood sugars.

Another "low alert" problem is similar to a high alert problem, and constitutes the issue of unnecessary re-alerts. That is, users are annoyed when they receive multiple low alerts for the same low glucose event. In many cases, such unnecessary re-alerts are caused by their glucose levels hovering just above or below their low threshold. Such may also be caused when users go above 55 but are still below their low threshold. In reaction to unnecessary re-alerts, users sometimes start ignoring alerts, or may turn off their low alert, or may over treat their condition, e.g., stacking carbs (which is often a particular problem at night). But such remedies cause the user to miss future unexpected low glucose levels.

Other low alert problems include that users may set their low alert threshold as the bottom boundary for their target range. Other low alert problems will also be understood.

Prior art in the field has dealt with certain alerting issues in the following ways.

In one way, as disclosed in U.S. Patent Publication No. US-2015/0289821, filed 16 Mar. 2015 and entitled GLYCEMIC URGENCY ASSESSMENT AND ALERTS INTERFACE, an actionable alert is disclosed as being provided based on a glycemic urgency index, which is a value that is more representative of a user's diabetic state than just a glucose value. Another publication, U.S. Patent Publication No. US-2014/0118138, granted as U.S. Pat. No. 9,119,528 on 1 Sep. 2015, and entitled SYSTEMS AND METHODS FOR PROVIDING SENSITIVE AND SPECIFIC ALARMS, discusses the occurrence of alarms that may be annoying to a user, but is directed to remedies such as waiting a particular time period or using a time delay. In yet another application, U.S. Patent Publication No. US-2015/0119655, filed 28 Oct. 2014 and entitled ADAPTIVE INTERFACE FOR CONTINUOUS MONITORING DEVICES, a user interface is adapted according to certain inputs, e.g., goals, population data, and the like. However, there is no disclosure of adapting the alerts themselves. In yet a further application, U.S. Patent Publication No. US-2014/0012510, filed 13 Mar. 2013 and entitled SYSTEMS AND METHODS FOR LEVERAGING SMARTPHONE FEATURES IN CONTINUOUS GLUCOSE MONITORING, disclosures are provided such that, e.g., if the user is in a meeting, an alert may be silenced. The reference discloses changing the timing of an alert, but only as part of a global setting, and not on a real-time basis. In yet another application, U.S. Ser. No. 62/289,825, filed 1 Feb. 2016, and entitled SYSTEM AND METHOD FOR DECISION SUPPORT USING LIFESTYLE FACTORS, feedback is provided to the user for decision-support purposes, e.g., informing the user of something useful for them and their treatment.

All of the above cited applications are owned by the assignee of the present application and herein incorporated by reference in their entireties.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways. In particular, systems and methods according to present principles only alert users when it makes sense to do so, e.g., only alert the user when the system can predict or estimate that the user is not already cognitively aware of their current condition, e.g., particularly where the current condition is a diabetic state warranting attention. In this way, the alert or alarm is personalized and made particularly effective for that user. Such systems and methods still alert the user when action is necessary, e.g., a bolus or temporary basal rate change, or provide a response to a missed bolus or a need for correction, but do not alert when action is unnecessary, e.g., if the user is already estimated or predicted to be cognitively aware of the diabetic state warranting attention, or if corrective action was already taken.

In a first aspect, a non-transitory computer readable medium is provided, including instructions for causing a computing environment to perform a method of dynamically adjusting or tuning user alerts based on a cognitive awareness determination, thereby providing data relevant to treatment of a diabetic state warranting attention, the method including steps of: (a) identifying a current or future diabetic state warranting attention, the identifying based at least partially on a glucose concentration value; (b) estimating or predicting a cognitive awareness of the user of the identified current or future diabetic state warranting attention; and (c) if the result of the estimating or predicting is that the user is cognitively unaware of the identified current or future diabetic state warranting attention, then alerting a user with a user prompt on a user interface of a monitoring device, the user prompt indicating the diabetic state warranting attention; (d) whereby the user is only alerted of the diabetic state warranting attention if and at a time that the user is unaware of the diabetic state warranting attention and that the notification is effective for the user.

Implementations of the aspects and embodiments may include one or more of the following. The alerting may be optimized for cognitive awareness of the patient such that fewer alarms occur than would otherwise be provided without consideration of user cognitive awareness. The monitoring device may be a smart phone, a smart watch, a dedicated monitoring device, or a tablet computer. In systems and methods according to present principles, overprompting, repeat prompts, or nuisance prompts are minimized or avoided. In systems and methods according to present principles, the user is enabled to build trust that the system will only alert on notifications optimized or effective for the user. The estimating or predicting a cognitive awareness of the user may include determining if the identified current or future diabetic state warranting attention includes an atypical glucose trace. The atypical glucose trace may include an atypical pattern or an atypical glucose response.

The estimating or predicting a cognitive awareness of the user may include determining if the user has previously treated a like identified diabetic state warranting attention by taking an action without a user prompt. The action may be dosing of a medicament, eating a meal or exercising. The estimating or predicting a cognitive awareness of the user may include determining if the user has entered meal or bolus data, or has requested a bolus calculation. The estimating or predicting a cognitive awareness of the user may include determining if user behavior is consistent with cognitive awareness. The estimating or predicting a cognitive awareness of the user may include receiving user input and basing the estimating or predicting at least in part on the received input. The estimating or predicting a cognitive awareness of the user may include analyzing historic data of glucose values of the user versus time.

The steps of identifying and estimating or predicting are repeated until such a time as the user is estimated or predicted to be cognitively unaware of the identified diabetic state warranting attention, and then performing a step of alerting the user with the user prompt. The estimating or predicting a cognitive awareness of the user may include receiving data from an application or website through an appropriate API. The estimating or predicting may be based at least partially on location data, namely GPS data. The location data may be that of the user or that of a follower of the user.

The estimating or predicting a cognitive awareness of the user may be based at least partially on one or more of the following: population data, data associated with behavioral or contextual information, data associated with a life goal of the user, data associated with a user privacy setting, or a combination of these. The estimating or predicting a cognitive awareness of the user may be based at least partially on real-time data, and where the real-time data may include one or more of the following: data associated with a GPS application in the monitoring device, data associated with an accelerometer in the monitoring device, data associated with behavioral or contextual information, data associated with a location of a follower of the user, data associated with a metabolic rate of the user, data associated with a glycemic urgency index of the user, heart rate data, sweat content data, data associated with a wearable sensor of the user, insulin data, or a combination of these.

The estimating or predicting a cognitive awareness of the user may include recognizing one or more individualized patterns associated with the user. The individualized pattern may correspond to an envelope of characteristic analyte concentration signal traces occurring before or after an event. The event may be associated with a meal, exercise, or sleep. The determination may be that the user is cognitively unaware if a current signal trace falls outside the envelope of characteristic analyte concentration signal traces.

The method further may include indicating a confidence level associated with the user prompt. If the result of the estimating or predicting is that the user is not cognitively aware of the diabetic state warranting attention, then the method may further include displaying the user prompt immediately. The estimating or predicting may further be based on location information of the user, where the location information indicates that the user is within a predetermined threshold proximity of a food store or restaurant. If the result of the estimating or predicting is that the user is not cognitively aware of the diabetic state that warrants attention, then the method may further include alerting the user with the user prompt after a time delay, a duration of the time delay based on at least the identified diabetic state warranting attention and the glucose concentration value rate of change.

The user prompt may include a query for a user to enter data. The query may request data for the user to enter about dosing, meals or exercise. If the user ignores the user prompt as determined by data from the user interface or data from an accelerometer associated with the monitoring device, and if the user prompt does not correspond to a danger condition, then the method may further include storing information about the user ignoring the user prompt under prior conditions and using the stored information as part of a subsequent estimating or predicting step.

The identifying a current or future diabetic state warranting attention may include determining a clinical value of a glucose concentration and/or a glucose rate of change and/or a glycemic urgency index value. The identifying a current or future diabetic state warranting attention may include measuring a glucose signal signature and comparing the measured signature with a plurality of binned signatures, and classifying the diabetic state warranting attention into one of a plurality of bins based on the comparison. The identifying a current or future diabetic state warranting attention may include determining one or more time-based trends in the glucose concentration value, and basing the identified state on the determined trend. The trend may correspond to whether the glucose concentration value is hovering within a range or is rising or falling, where hovering constitutes staying within a predetermined range for a period of greater than 5 or 10 or 15 or 30 minutes. Fuzzy boundaries may be employed for defining the range.

The method may further include transmitting an indication of the diabetic state warranting attention to a medicament pump. If the result of the estimating or predicting is that the user is not cognitively aware of the diabetic state warranting attention, then the method may further include activating the medicament pump to provide a medicament bolus. The medicament bolus may be a meal bolus of insulin. If the result of the estimating or predicting is that the user is not cognitively aware of the diabetic state warranting attention, then the method may further include activating the medicament pump to change a basal rate. The medicament may be insulin. The method may further include determining if the medicament pump can treat the diabetic state warranting attention either fully or partially, and if so, then not alerting the user or altering the user prompt, respectively, as compared to a case where the medicament pump cannot treat the diabetic state. If the result of the estimating or predicting is that the user is not cognitively aware of the diabetic state warranting attention, then the method may further include determining when to alert the user with the user prompt. The user prompt, if displayed, may include a color or arrow instead of or in addition to a glucose concentration value. The user prompt, if displayed, may include a prediction of a glucose concentration value. The user prompt, if displayed, may include an audible indicator, and where the volume of the audible indicator is automatically adjusted for ambient noise as measured by the monitoring device or by a device in signal communication with the monitoring device, where the adjusting for ambient noise may include raising the volume of the audible indicator relative to the ambient noise until a threshold level of signal to noise ratio is achieved. The user prompt may be related to a diabetic state warranting attention occurring during a period when the user has a glycemic urgency index that is low.

If the result of the estimating or predicting is that the user is not cognitively aware of the diabetic state warranting attention, then the method may further include alerting the user with the user prompt after a delay based not on a time duration but on the identified diabetic state warranting attention and on the glucose concentration value and/or a glucose concentration value rate of change. If the result of the estimating or predicting is that the user is not cognitively aware of the diabetic state warranting attention, then the method may further include alerting the user with the user prompt after a delay based not on a time duration but on an individualized pattern learned by the monitoring device.

The identified diabetic state warranting attention may correspond to an atypical glucose response or an atypical pattern, where the atypical response or atypical pattern is learned by a monitoring device and not by user entry. The user prompt may be displayed with dynamic timing on a predesigned user interface and not on an adaptive user interface. If the result of the estimating or predicting is that the user is not cognitively aware of the diabetic state warranting attention, then the method may further include alerting the user with the user prompt immediately regardless of indications to not alert the user with a user prompt received from other monitoring device applications. If the result of the estimating or predicting is that the user is not cognitively aware of the diabetic state warranting attention, then the method may further include alerting the user with the user prompt immediately regardless of indications to not alert the user with a user prompt based on other user-entered data or settings. The estimating or predicting if the user is cognitively aware of the diabetic state warranting attention may be based at least in part on real-time data and not entirely on retrospective data.

In a second aspect, a system for providing smart alerts corresponding to diabetic states warranting user attention is provided, including: a CGM application running on a mobile device, the CGM application configured to receive data from a sensor on an at least periodic or occasional basis and to calibrate and display glucose concentration data in clinical units; and a smart alerts application running as a subroutine within the CGM application or running as a parallel process with the CGM application on the mobile device and receiving data from the CGM application, the smart alerts application configured to perform the method contained on the medium of claim In a third aspect, a non-transitory computer readable medium is provided, including instructions for causing a computing environment to perform a method of safely reducing alerting of users to diabetic states that require attention, the method including steps of: (a) identifying a current or future diabetic state warranting attention, the identifying based at least partially on a glucose concentration value; (b) determining if the identified diabetic state warranting attention is atypical for the user; (c) if a result of the determining is that the identified diabetic state is atypical for the user, then alerting the user with a user prompt on a user interface of a monitoring device, the user prompt indicating the diabetic state warranting attention; (d) whereby the user is only notified of the diabetic state warranting attention if the identified diabetic state is atypical for the user.

Implementations of the aspects and embodiments may include one or more of the following. The determining if the identified diabetic state warranting attention is atypical for the user may include determining if the identified diabetic state may include a glucose trace following a pattern that is not typical of other patterns associated with the user. The determining if the identified diabetic state warranting attention is atypical for the user may include determining if the identified diabetic state may include a glucose trace following a trend that is not typical of other trends associated with the user.

In a fourth aspect, a non-transitory computer readable medium is provided, including instructions for causing a computing environment to perform a method of prompting a user about a diabetic state that warrants attention, the computing environment in signal communication with a medicament delivery device, the user prompt optimized for effectiveness to the user at least in part by being reduced in number, the user prompt providing data relevant to treatment of the diabetic state warranting attention, the method including steps of: (a) identifying a current or future diabetic state warranting attention, the identifying based at least partially on a glucose concentration value; (b) performing a first estimating or predicting of a cognitive awareness of the user of the identified current or future diabetic state warranting attention; (c) if the result of the first estimating or predicting is that the user is cognitively unaware of the identified current or future diabetic state warranting attention, then performing a second estimating or predicting of a computer awareness of the medicament delivery device of the identified current or future diabetic state warranting attention; (d) if the result of the second estimating or predicting is that the medicament delivery device is unaware of the identified current or future diabetic state warranting attention, then alerting the user with a user prompt on a user interface of a monitoring device, the user prompt indicating the diabetic state warranting attention; (e) whereby the user is only notified of the diabetic state warranting attention if and at a time that both the user and the medicament delivery device are unaware of the diabetic state warranting attention and that the notification is effective for the user.

Implementations of the aspects and embodiments may include one or more of the following. The method may further include steps of determining if the medicament delivery device is capable of treating the identified current or future diabetic state warranting attention, and if the result of the determining is that the medicament delivery device is incapable of treating the identified diabetic state, then alerting the user with the user prompt. The current or future diabetic state may include hypoglycemia, the medicament delivery device may be an insulin delivery device, and the method may further include shutting off or reducing activity of the insulin delivery device based on the diabetic state of hypoglycemia. The shutting off or reducing activity may occur sooner in the case where the user is cognitively unaware of the hypoglycemia. The performing a first estimating or predicting may be based at least partially on user interaction with the medicament delivery device.

In further aspects and embodiments, the above method features of the various aspects are formulated in terms of a system as in various aspects. Any of the features of an embodiment of any of the aspects, including but not limited to any embodiments of any of the first through fourth aspects referred to above, is applicable to all other aspects and embodiments identified herein, including but not limited to any embodiments of any of the first through fourth aspects referred to above. Moreover, any of the features of an embodiment of the various aspects, including but not limited to any embodiments of any of the first through fourth aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through fourth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through fourth aspects referred to above.

People with diabetes face many problems in controlling their glucose because of the complex interactions between food, insulin, exercise, stress, activity, and other physiological and environmental conditions. Established principles of management of glucose sometimes are not adequate because there is a significant amount of variability in how different conditions impact different individuals and what actions might be effective for them, and as noted above, even providing alerts or alarms is problematic because different situations call for different actions among different individuals. Providing alerts and alarms customized to the user and anticipatory of situations users may not be cognitively aware of is thus highly beneficial and desirable to users.

Accordingly, systems and methods according to present principles provide techniques to alert and/or alarm users pertaining to diabetic situations or states warranting their attention, but generally only when the system can determine, e.g., estimate or predict, that the user is not already cognitively aware of the situation. Consequently, such systems and methods according to present principles reduce the uncertainty that diabetes is typically associated with and improve quality of life.

Advantages may include, in certain aspects or embodiments, one or more of the following. "Smart alerts" are provided to advantageously notify users of diabetic states warranting attention, particularly where the user is otherwise cognitively unaware of the diabetic state. Such smart alerts thus do not annoy the user as they only happen when needed, and not when unnecessary, e.g., smart alert functionality would not alert the user if the user doses a proper amount of insulin at a proper time relative to a meal. Such smart alerts alert users of dangerous or urgent conditions more efficiently than in the case of prior art alerts, and provide greater assurance and confidence. Such "smart" alerts further avoid the problems of alert fatigue. In particular, because CGM apps running on smart phones have not previously been able to quantify the cognitive state of a user, alert fatigue commonly occurs with threshold-based alerting algorithms. Embodiments described herein infer cognitive state data by converting physiological and non-physiological data into an estimation or prediction of a user's cognitive state, providing for smarter alerts and reduced alert fatigue. Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and non-obvious systems and methods according to present principles, shown in the accompanying drawings, which are for illustrative purposes only. These drawings include the following figures, in which like numerals indicate like parts.

Like reference numerals refer to like elements throughout. Elements are not to scale unless otherwise noted.

DETAILED DESCRIPTION

Definitions

Figure 1:
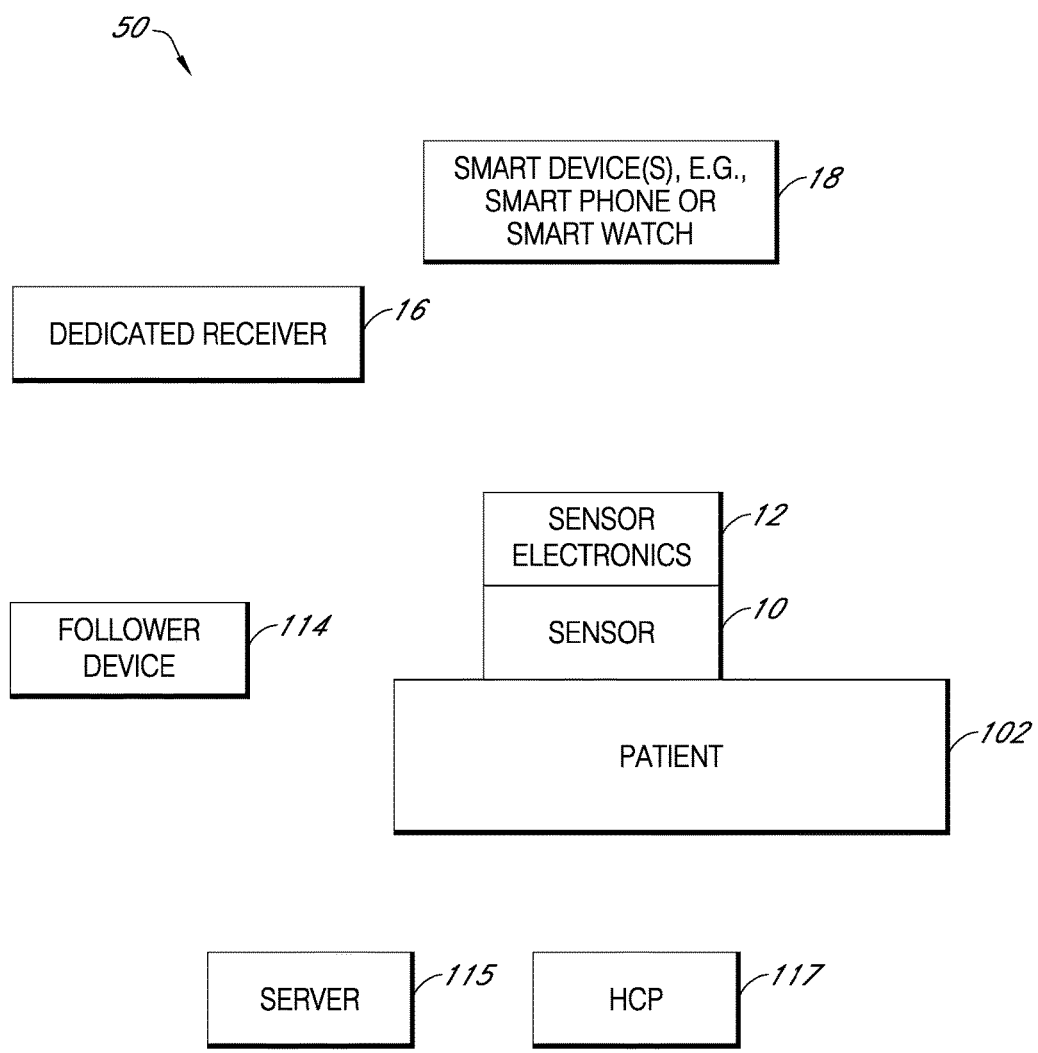
FIG. 1 is a schematic illustration of a system according to present principles.

In order to facilitate an understanding of the preferred embodiments, a number of terms are defined below.

The term "analyte" as used herein generally relates to, without limitation, a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle)), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine;

carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculusmedinensis, Echinococcusgranulosus, *Entamoeba histolytica*, enterovirus, *Giardia duodenalisa*, *Helicobacter pylori*, hepatitis B virus, herpes virus, HIV-1, IgE (atopic disease), influenza virus, Leishmaniadonovani, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii*, Trepenomapallidium, *Trypanosoma cruzi*/rangeli, vesicular *stomatis* virus, Wuchereriabancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "calibration" as used herein generally relates without limitation to the process of determining the relationship between sensor data and corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein generally relate without limitation to data that has been transformed from its raw state (e.g., digital or analog) to another state using a function, for example a conversion function, to provide a meaningful value to a user.

The term "algorithm" as used herein generally relates without limitation to a computational process (for example, programs) involved in transforming information from one state to another, for example, by using computer processing. In implementations described here, algorithms may implement decision-support application/functionality, which takes input from sensors, computer applications, or user input, and converts the same into outputs rendered to a user on a user interface or to other devices.

The term "sensor" as used herein generally relates without limitation to the component or region of a device by which an analyte can be quantified.

The terms "glucose sensor" generally relates without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

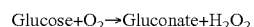

Glucose+$O_2$→Gluconate+$H_2O_2$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein generally relate without limitation to one or more components being linked to another component(s) in a manner that allows transmission of signals between the components. For example, one or more electrodes can be used to detect the amount of glucose in a sample and to convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "variation" as used herein generally relates without limitation to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein generally relate without limitation to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, and thus a physiologically feasible rate of change can be set at the maxima and minima based on continuous studies of glucose data. As a further example, it has been observed that the best solution for the shape of the curve at any point along a glucose signal data stream over a certain time period (for example, about 20 to 30 minutes) is a straight line, which can be used to set physiological limits. These terms are broad enough to include physiological parameters for any analyte.

The term "measured analyte values" as used herein generally relates without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein generally relates without limitation to an analyte value or set of analyte values, which have been algorithmically extrapolated from measured analyte values.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

The phrase "continuous glucose sensor" as used herein generally relates without limitation to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer.

The phrases "continuous glucose sensing" or "continuous glucose monitoring" as used herein generally relate without limitation to the period in which monitoring of the glucose concentration of a host's bodily fluid (e.g., blood, serum, plasma, extracellular fluid, tears etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60 seconds.

The term "substantially" as used herein generally relates without limitation to being largely but not necessarily wholly that which is specified, which may include an amount greater than 50 percent, an amount greater than 60 percent, an amount greater than 70 percent, an amount greater than 80 percent, an amount greater than 90 percent, or more.

The terms "processor" and "processor module," as used herein generally relate without limitation to a computer system, state machine, processor, or the like, designed to perform arithmetic or logic operations using logic circuitry that responds to and processes the basic instructions that drive a computer. In some embodiments, the terms can include ROM and/or RAM associated therewith.

The terms "decision-support application" and "decision-support application/functionality," as used herein generally relate without limitation to algorithms that use sensor data and/or other data, e.g., user-entered data, derived data, or data from other applications or sensors, to provide a user prompt on a display and/or a command to a mechanical device.

The term "distinct" in regard to variables or parameters as used herein generally relate without limitation to a parameters and/or variables that are independent and do not rely one upon the other. Conversely, the term "related" in regard to variables or parameters as used herein generally relates without limitation to parameters and/or variables that depend in some way on each other or are derivable from each other. For example, a sensor signal time derivative is related to a sensor signal, while a user's gender and current analyte concentration would be considered distinct. It is noted here, however, that multiple parameters used in decision-support application/functionality may involve a single act or event, e.g., the same may concern a timing and duration of exercise. The term "independent" is used in the same way as "distinct", and similarly "dependent" is used in the same way as "related", although "independent" may also refer to variables used in a function, wherein the output of the function is a "dependent" variable, with the dependency based on the underlying independent variables.

The term "insulin sensitivity" as used herein generally relates without limitation to the relationship between how much insulin needs to be produced in order to deposit a certain amount of glucose. It is a physiologic measure everyone has, and is not limited to diabetes. The same may vary throughout a person's day, e.g., and may be driven by hormones, activity, and diet. It may further vary throughout a person's life, and may be driven by, e.g., illness, weight, obesity, and so on. It is a general measure, e.g., like weight, blood pressure, heart rate, and so on. There are healthy ranges for insulin sensitivity, as well as unhealthy ranges. In diabetes management, users should generally know their insulin sensitivity factor (ISF) when making decisions about boluses. The term ISF is sometimes used interchangeably with "correction factor" (CF). For example, a typical calculation users may be required to perform may be, e.g., "if my blood glucose is too high by 100 mg/dL, how many units of insulin do I need to take to correct the high and bring my blood glucose down by that 100 mg/dL?" Many users use a default CF of 1:50, which means that one unit of insulin will reduce blood glucose by 50 mg/dL. The determination of insulin sensitivity, as well as the determination of other types of sensitivities, are discussed in greater detail below, but here it will be noted that knowledge of insulin sensitivity may be based on, e.g., real-time analysis of data from CGM, activity monitors, and insulin pump data, as well as on data from retrospective analysis of such sensors as well as data from, e.g., an electronic health record. Other factors that may bear on insulin sensitivity or ISF may include correlations with time of day, pain, and/or exercise; heart rate variability, stroke volume, other cardiovascular health related to metabolic issues; ability to distribute insulin; temperature; insulin type, based on insulin sensitivity measurements, profiles, peaks, time between peaks; atmospheric pressure (thus "airplane mode" may be an input); whatever activity affects the patient or user the most; and so on.

The term "insulin resistance" as used herein generally relates without limitation to a medical condition in which the cells in a person's body cannot make proper use of insulin for the normal processes of cells importing glucose, or other metabolites, from the bloodstream. Insulin resistance reduces insulin sensitivity. While everyone has an insulin sensitivity, only certain individuals suffer from having insulin resistance.

The term "lifestyle factors" generally refers without limitation to quantitative or qualitative (but in some way convertible to quantitative) parameters that are generally not measured directly with a physiological sensor but which are related to disease management. In some cases the same relates to a trend or recurring event, however minor, that systems and methods according to present principles may determine and use in providing a therapy prompt to a user or in changing or altering a therapy prompt to a user. However, trend information need not necessarily correspond to a pattern, although some patterns will constitute trend information. In some implementations, a lifestyle factor may be equated to the correlative parameter discussed elsewhere. Lifestyle factors (also termed "lifestyle context") may be related to certain quantities that are physiological, e.g., insulin sensitivity, but may also be related to more external parameters, such as sleep sensitivity, meal sensitivity, exercise sensitivity, and so on. In other words, lifestyle factors are generally quantitatively determinable, but in most cases are not directly measured by a sensor.

The term "state" and "state model" generally refer without limitation to a data structure useful for modeling a patient for purposes of, e.g., decision-support or smart alerts. Generally a state model of a patient envisions the patient as occupying one of a plurality of states, the states dependent on various lifestyle factors and clinical factors. As a specific example, the state of a patient may correspond to a current insulin sensitivity profile. The plurality of states or state model may then be employed in combination with a real-time input, e.g., time, calendar, CGM glucose value, rate of change, and the like, in order to provide a therapy prompt to the user supporting a therapeutic decision. In one implementation a number of diabetes decision states are defined by one or more highly correlative parameters, which can be lifestyle parameters, and which can be selected by the user through a user interface or learned over time via machine learning and/or cloud analytics.

The term "diabetic state warranting attention" generally refers to a biological state of a diabetic user in which it is desirable that an action be taken. For example, a condition of hypoglycemia or hyperglycemia is a diabetic state warranting attention. Where such conditions are impending or likely to occur, but has not happened yet, the user is also considered to be in a diabetic state warranting attention. Diabetic states warranting attention may vary in urgency, but generally refer to user conditions in which an action is estimable or determinable and is beneficial to the user, generally leading the user towards a condition of euglycemia or towards a center of a target range of glucose values, e.g., a target range corresponding to euglycemia.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (HCP, e.g., doctor, physician, nurse, caregiver), who may be using the sensor.

Although much of the description and examples are drawn to a glucose sensor capable of measuring the concentration of glucose in a host, the systems and methods of embodiments can be applied to any measurable analyte. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Publication No. US-2011/0027127. In some embodiments, the analyte sensor is a transcutaneous glucose sensor, such as described with reference to U.S. Patent Publication No. US-2006-0020187-A1. In yet other embodiments, the analyte sensor is a dual electrode analyte sensor, such as described with reference to U.S. Patent Publication No. US-2009/0137887-A1. In still other embodiments, the sensor is configured to be implanted in a host vessel or extracorporeally, such as is described in U.S. Patent Publication No. US-2007/0027385-A1. These patents and publications are incorporated herein by reference in their entirety.

The following description and examples describe the present embodiments with reference to the drawings. In the drawings, reference numbers label elements of the present embodiments. These reference numbers are reproduced below in connection with the discussion of the corresponding drawing features.

Systems and methods according the present principles provide ways to incorporate "smart alerts" in analyte monitoring systems, and in particular continuous glucose monitoring systems. In one implementation, smart alerts can be provided by its own application or algorithm, which generally runs alongside a CGM application. In another implementation, smart alerts can be implemented by additional programming/instructions added to an existing application, e.g., a CGM application. For this reason, in this specification, the smart alerts provided are generally referred to as smart alerts application/functionality.

Certain exemplary aspects are shown in FIG. 1. In the figure, a system 50 is illustrated in which a patient 102 wears a sensor 10, and the sensor transmits measurements using sensor electronics 12. The sensor electronics may transmit data corresponding to analyte measurements to a smart device 18, e.g., a smart phone and/or smart watch, to a dedicated receiver 16, or to other devices, e.g., laptops, insulin delivery devices or other computing environments. Currently measured data, historical data, analysis, and so on, may be transmitted to a server 115 and/or a follower device 114'. Such data may also be transmitted to a healthcare professional (HCP) device 117. More detailed aspects of the sensor itself and sensor electronics are described below with respect to FIGS. 45 and 46.

Figure 2:
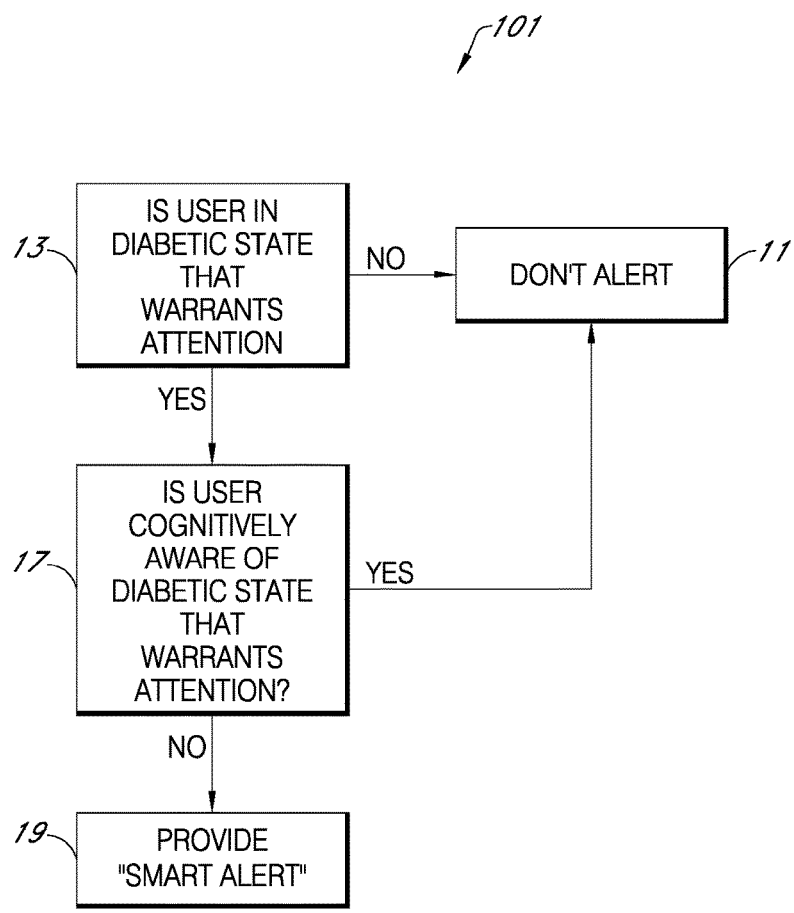
FIG. 2 is a flowchart of a first method according to present principles.

Referring to the flowchart 101 of FIG. 2, a method according to an implementation of present principles is seen for enabling smart alert functionality within an analyte monitoring system, e.g., within a continuous glucose monitor. A first step is a determination as to whether the user is in a diabetic state that requires or warrants attention (step 13). This step is generally performed in most implementations as, if the diabetic state does not warrant attention, a smart alert need not be given (step 11). As noted, however, even if the user is in a diabetic state that warrants attention, an alert is not always given.

In particular, an estimation or prediction is made by the system using various data, which may be past date and/or real time data, and which may be from a sensor and/or other measurement devices, as to whether the user is cognitively aware of the diabetic state that warrants attention (step 17). If the result of the estimation or prediction is that the user is cognitively aware, then again a determination will be to not alert (step 11). However, if the result of the estimation or prediction is that the user is not cognitively aware, then a smart alert may be provided (step 19).

Generally the estimation or prediction will be done in an automatic manner, and will be based on stored data, or current data received or determined. While various types of input data will be described below, here it is noted that such data may relate to data having the signature of a pattern (if the user has experienced the pattern many times before, it may be assumed that they are cognitively aware), behavioral data, historical data (including the use of retrospective analyses in some implementations), and so on. The result of the estimation or prediction may be a binary yes/no, but in many other cases will be in the nature of a quantitative estimation or prediction, e.g., with a percentage likelihood that the user is cognitively aware. Of course, by comparing the percentage with a single threshold, the same may be transformed into a yes/no response. In various other cases, however, particularly where multiple thresholds are involved, multiple and different responses may result depending on the value of the percentage likelihood.

Other alternative implementations may include the use of user input. For example, by the use of slider bars, a selection of a choice of radio buttons, or other user interface mechanisms, users may affect the operation of the smart alerts functionality. Users may also affect the sensitivity of the functionality, depending on their desire for reminders and alerts. Users may further affect the content of the reminders, by selecting what information they would like to review upon the occurrence of one or more categories of alerts/events. Via a suitable selection, users can thus affect the operation, timing, and display of smart alerts.

Details of the above-described functionality are now described.

Figure 3:
FIG. 3 illustrates schematically where a smart alerts application may run or be instantiated, according to present principles.

Referring to FIG. 3, the smart alerts functionality may operate as a secondary application 25, running alongside a primary analyte monitoring application, e.g., a primary CGM app, on a smart device 18, or the same may be provided as functionality within the CGM app (or another app) running on the smart device 18. In either case, other functionality may be implemented as part of such a secondary application or functionality. Implemented as a secondary application running alongside a primary monitoring application, additional or subsequent update functionality may be tested without affecting the functionality of the main CGM app. Generally, the smart alerts functionality provides technological improvements to the operating of the monitoring application, as fewer alerts are usually needed, which is less expensive computationally, saves on battery power, and so on. In addition, the device itself is provided with technological functionality related to data that prior systems lacked, e.g., data about cognitive awareness of the user of their diabetic state.

Figure 4:
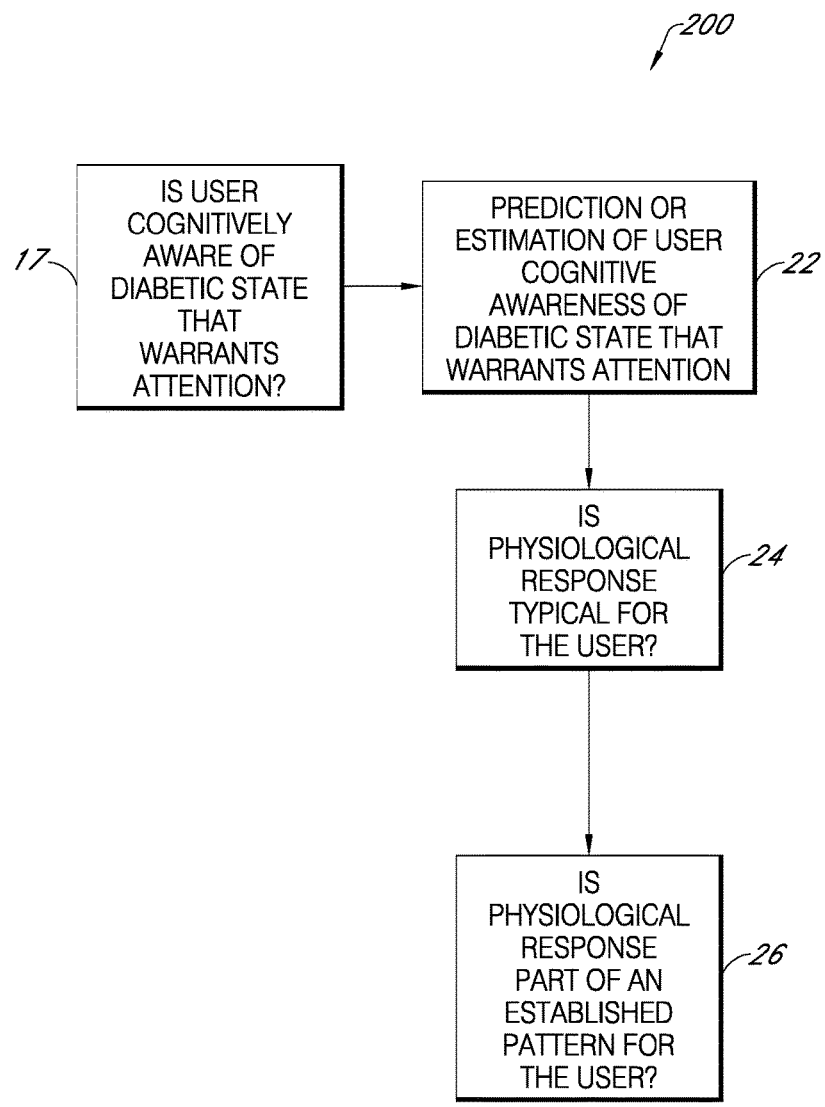
FIG. 4 is a flowchart of a second method according to present principles.

Referring next to the chart 200 of FIG. 4, additional details are provided for step 17, that is, for the system to utilize machine learning and stored and/or real-time data to determine whether the user is cognitively aware of the diabetic state that warrants attention. As noted above, in some implementations this step is potentially phrased as constituting machine or system learning for prediction or estimation of the user cognitive awareness of the diabetic state that warrants attention (step 22). That is, the system determines metrics that are used in machine learning but also used in real time to obtain or determine data that is in some way compared to other data, e.g., compared to a threshold, to provide a prediction or estimation as to the user cognitive awareness, and the same then employed in a determination to provide a smart alert.

One way the system can determine such metrics allowing prediction or estimation of user cognitive awareness of such a diabetic state is by determining data about if the diabetic state, or put another way the physiological glucose response experienced, is typical of data previously seen and/or experienced by the user (step 24). If the machine learning learns what is typical data for the user, and if metrics obtained or determined indicate that current real-time data is similar to such typical data, then in many cases no alert need be given, as the system determination may be that the user is already cognitively aware, i.e., the estimation or prediction results in a high likelihood that the user is aware of their diabetic state that warrants attention. Such similarity in data may be determined in a number of ways, including determining if a real-time current glucose trace has a characteristic signature that is similar to a previously determined characteristic signature, e.g., duration, rise time, width, FWHM, and so on. Conversely, if the physiological response is atypical for the user, then there is a correspondingly lessened quantitative likelihood that the user has such cognitive awareness, and in this case a smart alert may be generated based on the data of the lessened quantitative likelihood, the smart alert resulting in a rendering on a screen or display of an indication of the diabetic state warranting attention, where it is understood that such rendering results in an alteration of the user interface portrayed on such a screen or display. For example, the physiological response may include a series of measured glucose values with respect to time. If the series of measured glucose values is similar to prior series of measured glucose values encountered, e.g., over the same or a similar time period, e.g., a quantified similarity is greater than a predetermined threshold criterion, then such similarity increases the likelihood that the user is aware of their diabetic state that warrants attention.

In a particular implementation, it may be determined if the physiological response is part of an established pattern for the user (step 26). Here the term "pattern" is used to relate to a repeating data arrangement identified in received data, e.g., in glucose monitoring, an occurrence of "overnight lows" that commonly occurs with the user. If the physiological response is part of a pattern that the user has encountered before, then again the estimation or prediction of likelihood of user cognition may be high, or in a more quantitative and/or granular calculation, may be raised or heightened. The degree of heightening or raising may be based at least in part on the frequency or number of times the user has experienced the pattern previously. The identification of an established pattern may include the following steps, which generally pertain to a series of measured glucose values with respect to time. The identifying may include: quantifying a similarity in the received data over two or more periods of time, and if the quantified similarity is greater than a predetermined threshold criterion, then identifying the similarity as an established pattern. Typical identified patterns may include overnight lows, post-meal highs, post-meal lows, time of day highs, time of day lows, weekend versus weekday highs/lows, post event highs/lows, and best days. To the extent these identified patterns occur in a given patient, smart alerts functionality may be configured to not cause an alert to be given to the patient, as there is a high likelihood of cognitive awareness. It is further noted that in many cases events precede physiological responses, and such events may be detected and identified as being common to and/or preceding the repeating data arrangement constituting the detected pattern, e.g., having appeared in two or more data arrangements, half the data arrangements, 75% of the data arrangements, or the like. In this sense the term "common" is used to refer to appearing in more than one data arrangement constituting a pattern, and not necessarily common to the user in general. The prevalence of the event may be measured with reference to a predetermined ratio or percentage, such as appearing in at least 25% of the data arrangements constituting the pattern, 50%, 75%, 90%, 95%, 99%, and so on. To the extent an alert is to be predicated on the occurrence of an event, and to the extent the alert would include recitation of the event as a cause, smart alerts functionality may further be configured to suppress or not alert on the particular event, as again the user may be estimated or predicted to be cognitively aware of the event.

In a specific implementation, it is noted that past systems predicated the issuance of an alert based on the passing of a threshold glucose alert, before an alert would be sounded that a user was going out of range. Predictive algorithms have been employed to develop predicted data using a prediction algorithm which is in turn compared to a threshold to provide users advance warning that they are going out of range. In both cases, however, the system tolls the issuance of an alert until some degree of present or expected glucose excursion has occurred.

In systems and methods according to present principles, however, past data, as well as current real-time data corresponding to glucose responses to events such as exercising or eating, may be leveraged via machine learning to identify a typical response for users. When the user is having a typical response, the system may suppress the issuance of an alert or the system may never generate the alert in the first place.

However, when the systems or methods identify that a current glucose trace is not typical as compared to prior glucose traces, i.e., the user is having an atypical response, users are alerted to take appropriate action. For example, a user may, at lunch, be determined to have atypical glucose response of a rise at 2 mg/dL to a high of 160-220 mg/dL within one hour. If the smart alerts functionality identifies an atypical response, e.g., such as a glucose trace showing a rise of 3 mg/dL or achieving a range of above 160 mg/dL within 30 minutes, then the system can base a smart alert on the atypical trace, causing a rendering of an indication of the smart alert on a screen or displaying, alerting the user of a likely high glucose. Importantly, such a notification is not based just on a glucose trace passing a threshold or a predicted glucose value as in prior systems, but rather on the glucose response being atypical or abnormal and thus likely leading to a uniquely high glucose level after this particular lunch. In this way, the smart alerts functionality operates in a unique and very different way than prior systems.

A particular benefit of this implementation is that the user is not being informed simply that their glucose is out of range or will soon be out of range, but rather the user is being informed of additional information, i.e., that their glucose response is not typical for them. That is, based on the determined or obtained data, a unique and customized smart alert notification is portrayed on a user interface rendered on a display or screen, displaying data of a type that has not been displayed before and further has not even been calculated before. Such notification allows the user to take additional precautions, unknown using the technology of prior systems, to manage and treat this more unique scenario.

Figure 5:
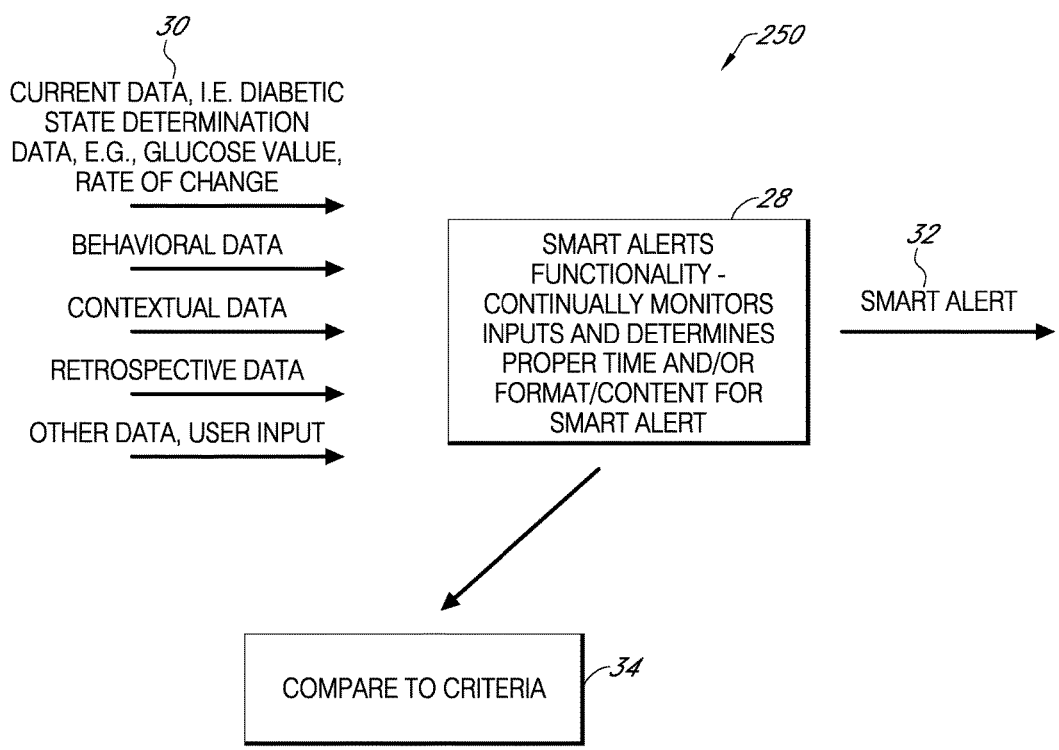
FIG. 5 is a logical diagram of inputs to a smart alerts functionality or application, and a resulting smart alert output.

Referring next to the flowchart 250 of FIG. 5, the smart alerts functionality 28, which may be implemented by appropriate subroutines or modules, and which may operate alongside a monitoring application or provide functionality within a monitoring application, accepts various types of inputs data 30 and, depending upon the input data, generates a smart alert 32 in response thereto. In so doing, the smart alerts functionality or module may perform relatively continuous evaluations. That is, generally the application does not just delay the providing of an alert by a predetermined time so as to render the same more convenient for the user. Rather, the application continuously evaluates data inputs 30 and determines, based on the data, or based on other data, when and if to generate an alert. For example, if the system and method learn that a particular user generally emerges from a "high after lunch" (postprandial high) 45 minutes after eating, then no alert will be generated so long as the actually observed glucose trace, indicating the high, is consistent with that pattern or typical user response. If the physiological response becomes inconsistent with the pattern or typical user response, e.g., data of the measured and calibrated glucose data trace from the glucose sensor differs substantially from typical glucose data traces, e.g., is different by more than a predetermined threshold, thus making the response atypical, then the system will estimate or predict that the user is not cognitively aware, and a smart alert will be generated and an indication rendered on a screen or display. Individualized or personalized user information/data is generally employed in the determination of whether (or when) to generate the smart alert, particularly as the same is generally transformed into data usable for an estimation or prediction of user cognitive awareness, and data of the estimation or prediction of cognitive awareness may subsequently be employed in the determination of the timing of the alert, the way in which the alert is provided, the content of the alert, the format of the alert, and so on. In general the generation of the smart alert, and/or its content or other features, are personalized or dynamically adapted or tuned to the user.

Individual inputs are described below, and the same may include data received as measured by signals, calibrated data, data from a user interface of a monitoring device (including dedicated devices and smart phones/watches), e.g., data about keystrokes, taps, frequency of interaction, apps used, and so on. Here it is noted that the mechanics of the estimation or prediction of cognitive awareness, i.e., how the smart alerts functionality is performed, can generally include comparison to a criterion (step 34). For example, a criterion may include a known pattern, and a glucose trace, e.g., a physiological response corresponding to a diabetic state warranting attention, may be compared to the known pattern (criterion) in the determination of whether the physiological response is typical. For example, a similarity may be gauged in shape, rise slope/time, duration, time of day, day of week, and so on.

Inputs

Analyte Concentration

Various metrics may be employed in the building of appropriate algorithms to operate such smart alerts functionality, such metrics indicative either individually or in combination to derive an estimation or prediction of cognitive awareness of a diabetic state warranting attention. In some cases such metrics are transformed into the estimation or prediction data, and in other cases an algorithm is used to derive the estimation or prediction data. Such metrics include rate of change, time to a threshold glucose level (e.g., how fast their glucose changes the first 20 mg/dL), insulin on board, and so on. A primary driver in smart alerts functionality is a real-time analyte concentration value, e.g., glucose value, measured by a glucose sensor, as well as glucose rate of change, derived from the glucose value measured by the sensor. However, other physiological quantities may also be employed. In some cases reception of data/calibration of data/display of data is performed by a single physical device, while in other cases multiple devices may be used, and in such cases data may be transmitted from one device to another as needed and according to appropriate data transmission protocols.

Besides quantities measured or derived from glucose sensor data, another quantity that may be employed is a glycemic urgency index, as described in US Patent Publication No. US-2014/0289821, filed Mar. 16, 2015, and entitled GLYCEMIC URGENCY ASSESSMENT AND ALERTS INTERFACE], owned by the assignee of the present application and herein incorporated by reference in its entirety.

User Input or Behavior

User input or behavior, as gleaned by data input to systems according to present principles, can also be employed in the estimation or prediction of cognitive awareness. For example, user behavior can indicate cognitive awareness as certain user behavior is consistent with user self-treatment of diabetic states warranting attention.

In one specific example, machine learning combined with system data of user interface usage may be employed to learn that the user responds to a first alert but rarely or never to subsequent ones. Thus, in this example, a first alarm may be made more evident, as it is known that future alarms will be ignored.

User "clicks" or icon "activations", as determined from user interface usage data, may further be employed to determine cognitive awareness. For example, if glucose trace data indicates that a user has entered a diabetic state warranting attention, but if the user immediately starts checking their monitoring app, e.g., calculating a bolus or rescue carb amount, then such activity strongly indicates the user is cognitively aware of their diabetic state, i.e., tending to raise the likelihood of cognitive awareness higher in a quantitative estimation or prediction. In such cases smart alerts may be suppressed or never generated.

In the same way, entering certain types of data may be used in the estimation or prediction algorithm. For example, if a user has a diabetic state warranting attention of hypoglycemia, but the user enters current meal data, then the user-entered data indicates cognitive awareness of the hypoglycemic state, and thus would cause suppression of a smart alert, or the lack of generation thereof. In some cases, where it is a "closer call", such a calculation may involve converting the user entered data to carbohydrate data in order to determine if the user is intending to treat a low or is simply eating without such awareness. The same is true of entering bolus data in response to hyperglycemia, and so on. Entering data (by the user) for a bolus calculation may further indicate user cognitive awareness, as can entering data (by the user) setting parameters for the user interface, e.g., manipulation or tuning of slider bars. The value of the parameters themselves, e.g., low aggressiveness, medium aggressiveness, high aggressiveness, may themselves be used as separate inputs into smart alert functionality. Thus, in these implementations, relevant data includes: (1) the entry of data into an application pertaining to health and diabetes management, along with (2) the value of the data itself.

Entry of meal data may cause other variations in processing, which can further affect the generation or suppression of smart alerts. In some implementations, these aspects serve as an incentive for the logging of insulin and carbohydrates. For example, if a user logs a significant amount of carbs, the monitoring application may automatically raise an alert threshold level by a predetermined amount for a predetermined duration of time, e.g., may automatically raise a high alert level by 100 mg/dL for 2 hours. In this way, the same "desensitizes" the high alert level for the postprandial meal spike. Put another way, instead of basing an alert based on cognitive awareness of the diabetic state warranting attention, this aspect modifies the system definition of the diabetic state warranting attention. In implementations, the amount of alert level increase can be configurable, e.g., from 0 to 200 mg/dL in 25 mg/dL increments, with the default level being 100 mg/dL. Where the level increase is 0, such essentially turns off the feature. The duration of time may be configurable from, e.g., 30 minutes to 3 hours in 15 minute increments, with the default period of time of two hours. The threshold level of carbs at which this desensitization subroutine is initiated may vary, but the same may be, e.g., 2 or 3 carb units. It will be understood that such generally depends on insulin/carb ratio. If known, parameters such as insulin on board and carbs on board may be taken into account in the desensitization subroutine. Benefits of such desensitization subroutines are many-fold, including that only one setting screen is added, and that if the default values are applicable, no initial setup is required. If the user has a connected pump and the insulin/carb ratio data is communicated using an appropriate transmission protocol from the pump's bolus calculator, then the set-up is automatic and no additional data entry is required. System or machine learning may still be advantageously employed in the implementation of this feature as well, as machine learning may be performed to determine when the user typically enters meal data vis-a-vis when the meal data is actually consumed, e.g., following consumption of the carbs, before consumption of the carbs, and so on. Such logging, when combined with glucose data indicating a potential hypoglycemic situation, may be analyzed and used to suppress the generation of a smart alert, which alert may be unnecessary given the expected postprandial rise.

Other relevant data may include user entered content data, which may be data entered on a form or using multiple-choice radio buttons or the like. For example, users may be requested to directly comment on the usefulness of a given alert. The user could be prompted to acknowledge the alert by depressing a button selected from a convenient and easy-to-understand user interface. Buttons may be provided such as "THANK YOU" or "GO AWAY". Responses such as these can allow the user to rapidly acknowledge the alert and yet still be transformed into highly useful data for future calculations in smart alerts functionality. For example, if an alert was provided two hours after a meal, but was noted by the user as being not helpful, a next iteration may have the user being alerted 2.5 hours after a meal (and if other alert criteria are met). As another example, if an alert is expressly noted as not helpful, the alert will not be repeated (i.e., defining criteria for smart alerts determinations in the future). If an alert is ignored, it may be not repeated if other data can be used to indicate user awareness of the diabetic state, in which case the alert may be determined to be being purposely ignored. If it is not clear if the ignoration is purposeful, the alert may be repeated. The system and method can also determine data based on machine learning from either purposeful ignoration or by user activation of an "ignore" button. For example, the system and method may alert a user at 180 mg/dL (and rising) multiple times with no response or with an activation of an "ignore" button. In such a situation, the monitoring app employing smart alerts functionality may ask the user if they do not desire this level of alerting, e.g., if they do not wish to be alerted again in a similar situation. Such data may then cause a change in how such smart alerts are output, i.e., will cause additional tuning or personalization to the user. In other words, such data may then be employed in algorithms optimizing the generation of smart alerts by applying calculations that take into account user interaction data (as determined by user interface interactions) or other non-physiological data as well as physiological data. Such algorithms may be operated on a smart phone type device as well as on other devices, e.g., smart watches.

Other relevant user entered data may include event data, e.g., if the user is about to perform or take part in an event that may bear on their glucose value. For example, if the user is about to exercise, e.g., do a long workout, where they know their glucose will be outside of their normal range, the user may activate a setting on their monitor, e.g., click a button on their smart phone, to activate a special "work out" alert schedule. Such a workout alert schedule may provide different alert values for the duration of the event. Other such events which could have special alert schedules may include meals, sleep, or the like.

Data pertaining to feedback from the user can be received from a user interface at various times during the resolution of a diabetic state warranting attention, e.g., during the event, well after the event, and so on.

Prompts or other questions inviting user response may be provided at various times so as to learn directly about user cognitive awareness or to learn about "markers" that indicate user cognitive awareness. In more detail, prompts or other invitations for user interactions, particularly with regard to entering data, may be provided to glean specific needed data, i.e., dated determined to be particularly useful in determining user cognition. Such data may be specific to a user or to a group of users, e.g., a user's cohort, or to a larger population. Put another way, the system using machine learning may prompt a user to enter a specific type of data so that the system receives data determined to be particularly useful. Such received or transmitted data pertains not just to the existence of user interaction but to the actual content and value of the user interaction.

Besides use of directly-entered user information, inferred user information may also be employed in smart alerts functionality. For example, a user's lack of action can be used. For example, if a user is at 40 mg/dL and has not performed any actions in an hour, alerts can become more pervasive. This situation may be detected by a firmware or software routine that is configured to measure the amount of time a user is in a dangerous or undesirable range and which has, as an additional input, keystroke or tap data from a user interface. As another example, if the user begins checking their display device with a high degree of interaction, then alerts may become more active, interactive, or aggressive, as the system can learn that, at that point in time, the user is in a mode where they desire a significant amount of interaction and information. Similarly, data from a user interface may be employed to measure what a "significant" amount of user interaction is, relative to a "normal" or "typical" amount. For example, a normal or typical amount may be determined by user input data over time, e.g., via an average number of apps opened or taps per minute or per hour. That number may be employed as the basis for a threshold, and once many more such taps are measured or detected, a user "high interaction" mode may be defined and used. Put another way, increased user interaction with the device can have a similar effect as a user moving a slider bar in a setting parameter to a more aggressive state. In part such automatic setting of a parameter may depend on to what extent the user interaction indicates user cognitive awareness. User interaction may be unrelated to a diabetic state warranting attention, e.g., if a user is responding to email or watching videos. Thus, user interaction may be discriminated in that only interactions related to analyte monitoring are considered, e.g., CGM, bolus calculation, and so on. Haphazard and frantic interaction of such apps may indicate user cognitive unawareness and a desire for interaction. The measurement of haphazard and frantic interaction may in some implementations take into account accelerometer data, e.g., where the device is being handled in a frantic way. The smart alert would be generated in this instance. User-focused interaction, e.g., a deliberate and "typical" performing of a bolus calculation, particularly with a keystroke or tap frequency that is usual for the user, e.g., within a range that is deemed "acceptable" or "usual" or "typical", would on the other hand indicate user cognitive awareness, and thus would contraindicate the generation of a smart alert. A complete lack of accelerometer signal variation may indicate that a user has fallen or has passed out. In this case, if an alert is not acknowledged or a lack of movement continues, smart alert functionality may be configured to send an alert to a follower or to another caregiver associated with the user. In general, any user interaction determinable or measurable in real time from the user interface of a device running an application related to health may be used in the determination of when and/or whether to alter a user interface using the application, e.g., to provide an alert, particularly when used in combination with real time glucose data, and such user interaction is defined as actions not only taken by a user on the user interface but also actions not taken by a user.

Prior or historical user responses (either physiological or through a user interface) may be employed to develop, generate, or refine future smart alerts functionality, e.g., to eliminate or reduce user "yo-yo" responses, or the like. In more detail, such prior or historical user responses are typically embodied in some form of data file, and retrieval, e.g. transmission, and analysis of such stored data may be employed to generate and refine smart alerts functionality so as to determine what smart alert led to a desired physiological response in the past (and conversely what types of smart alerts led to an undesirable physiological response in the past). Such analysis may include analysis of glucose trace data (and accompanying event data if necessary) to determine characteristics of desired and undesired responses, and then analysis of current physiological data to determine the existence of a current diabetic state warranting attention. If a smart alert is determined to be appropriate for generation, the smart alerts functionality may cause selection of the type of smart alert that led to a desirable physiological response in the past.

Detection and Use of Patterns

Patterns in glucose can be useful in understanding and helping patients manage their diabetes and how physicians manage their patients. Efforts have been made in the determination of patterns that highlight areas that require or need attention by a user.

U.S. patent application Ser. No. 14/874,188, filed 2 Oct. 2015 (not yet published), entitled SYSTEM AND METHODS FOR DATA ANALYTICS AND VISUALIZATION, and U.S. Patent Publication No. US-2013/0035575, filed 3 Aug. 2012 and entitled SYSTEMS AND METHODS FOR DETECTING GLUCOSE LEVEL DATA PATTERNS, both owned by the assignee of the present application and herein incorporated by reference in their entireties.

As noted above, pattern data may be employed in the determination of user cognition of diabetic states because if a user has a pattern of a certain physiological response, it can be inferred that upon the recurrence of such a physiological response, the user will recognize the pattern and take appropriate action. In other words, the user can be assumed to be cognizant of patterns experienced before, raising the estimation or prediction of user cognitive awareness. And further as noted above, the recurrence of a pattern may be determined by storage and analysis of prior data, particularly those identified as patterns (but not necessarily patterns), and comparison of the same to a currently measured (occurring) glucose trace to determine if the currently occurring glucose trace has curve or signature characteristics similar to those identified before.

One way of determining such patterns, or of detecting occurrences of glucose events not in patterns, is by "binning" certain events defined by particular characteristics. That is, portions of glucose traces may be detected that meet predefined criteria indicative of certain diabetic challenges, e.g., rebound hypoglycemia, and then patterns may be looked for in these events that have been "binned" accordingly (or may be determined to not be in such binned patterns)

Figure 6:
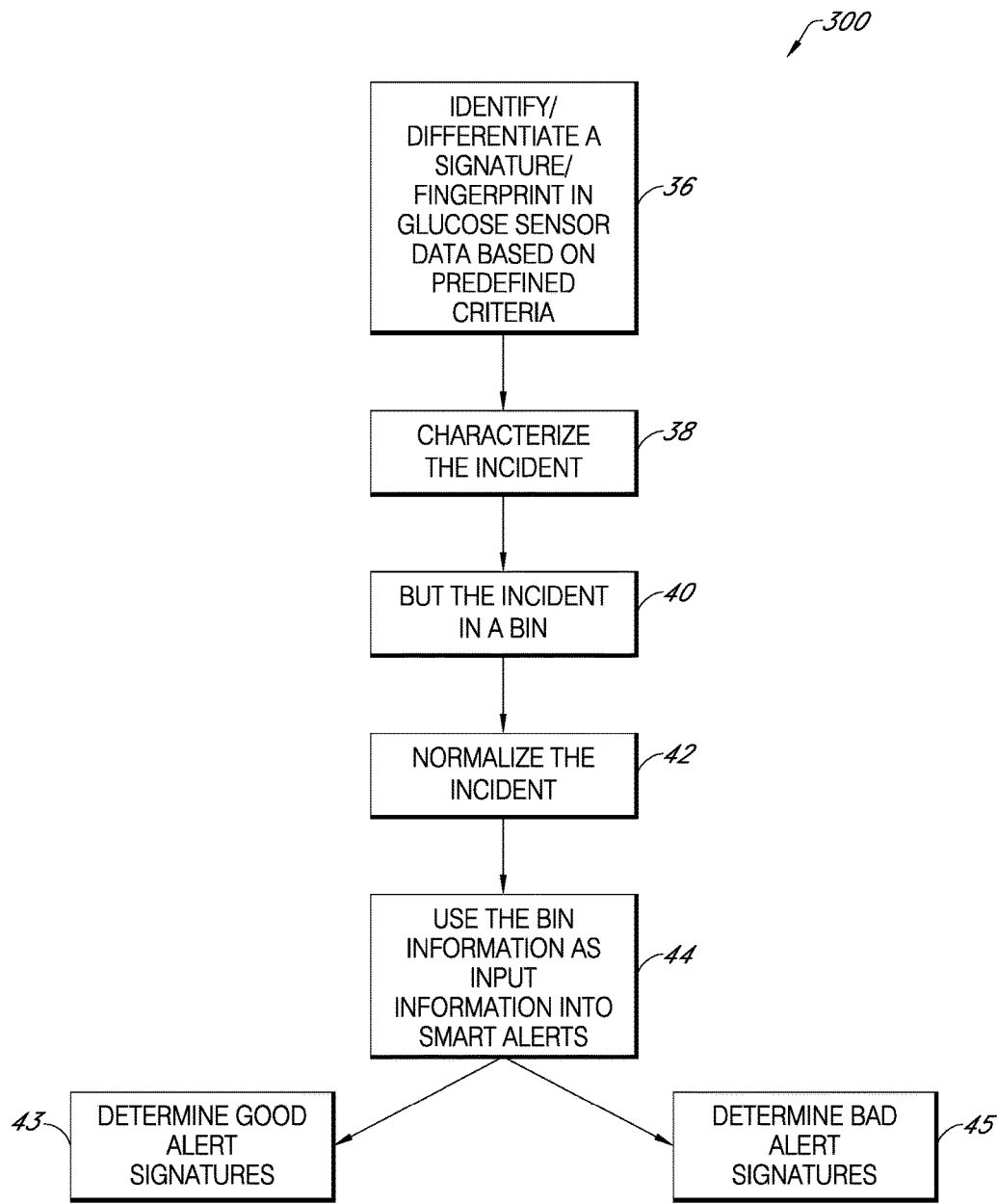
FIG. 6 is a flowchart of a third method according to present principles.

In more detail, and referring to the flowchart 300 of FIG. 6, a signature or "fingerprint" in glucose sensor data may be identified or differentiated within an individual patient based on some predefined criteria (step 36). Such criteria may include time-based criteria and/or may include detected specific incidents within specific constraints. In the present system, according to present principles, bins may be differentiated by different criteria. A supervised learning algorithm may be employed that allows for more bins to be learned for individual specific patterns. For example, bins can be based on insulin data, rate of change of glucose data (or acceleration/deceleration thereof), patterns of data identified before and used to characterize data, e.g., events occurring before small meals, responsiveness of an individual to their glucose information, and so on.

A next step is that the incident may be characterized, e.g., based on a decay curve, waveform signature, or the like (step 38). Exemplary incidents may include meal bolus indicators, e.g., based on insulin data, which may be classified into small, medium, and large meal bins. Such may correlate with insulin data. Different meal types may also be characterized, which may then be sub-binned into different meal compositions. These may correlate with rate of change/acceleration/deceleration. Incidents can also be characterized based on their correlation with events before a meal, and such corresponds to the patterns of data noted above. Incidents may further be based on behavioral patterns, e.g., how often a user reviews their glucose data or responds to alarms, and such can be correlated with the responsiveness data noted above. It will be understood that other bins may also be employed. Thus data about not only the incident but also user response data may be patterned, further providing data useful in algorithms for estimating or predicting user cognitive awareness, when such incidents and/or user responses recur.

The characterized incidents may then be placed into a bin (step 40). By then synchronizing by incident, bins may be tuned for specific patient physiology. The bins can then be normalized, i.e., a normal distribution of incidents in the bin may be defined (step 42).

The normalized bin information may then be used proactively as a data input into the smart alerts functionality (step 44), e.g., in the estimation or prediction of user cognition. The binning technique may be employed to determine when a patient is more tuned into their data, based on behavioral input, which may then allow for deductions, estimations, or predictions about user cognitive awareness.

Another use of such a binning technique is to identify good or successful alert signatures (step 43), e.g., ones representing diabetic states and alert types that the patient successfully responds to, from bad or unsuccessful alert signatures (step 45), i.e., ones representing diabetic states and alert types that the patient ignores. Smart alerts may then be provided based on this information, i.e., smart alerts may determine when and how to alert by comparison to the good alert signatures (if the diabetic state is within a predetermined proximity (in glucose traces) to that in a good alert signature, then such may provide a trigger for a smart alert). In this case that the use of good alert signatures does not depend on an estimation or prediction of user cognitive awareness, although the same may be used in combination with such estimations or predictions.

Patterns may also be identified by recognizing repeated occurrences of conditions or events over the course of CGM wear. In order to find these repeated occurrences, algorithms may synchronize CGM data, e.g., stored within buffers or data files, in each epoch (day, week, or month) and compute an average or distribution of CGM values as a function of time. The synchronization may be done by absolute time in order to look for, e.g., nighttime lows or early morning or afternoon highs/lows. One problem with this approach is that users may not always eat at the same time or take insulin at the same time, and thus patterns may not be clearly apparent. Accordingly, in systems and methods according to present principles, patterns may be identified that correspond to time of food intake or insulin dosing. Such patterns may be identified using the techniques noted above. For example, a sudden change in glucose within a predefined duration in the morning can be identified as "breakfast". With the use of smart phones and data communications between pumps and monitoring apps, data corresponding to a pre-meal bolus communication from a pump may be transmitted to a monitoring device such as a smart phone and used as an indicator for food intake. Other such indicators may include data from a GPS app, e.g., to determine likely food-intake-related glucose changes as may occur at frequented restaurants, changes in activity as determined by accelerometer data for exercise related effects on CGM, and so on. In this way patterns may be (machine) learned about responses closest in "time proximity" to a meal, or to nighttime, or on "geographic proximity", e.g., how far a user is from home or a source of food, and so on.

Once a specific time of synchronization is selected, data corresponding to CGM traces in each of these epochs can be overlaid on top of each other to generate statistics. For example, an average of the traces can be employed to distinguish real effects from random occurrences. Any true glucose effect due to a patient's physiology that is repeating is likely to be enhanced and other random effects are likely to be canceled or averaged out.

Data corresponding to distributions of CGM over time will provide the most likely glucose value after the synchronizing event and associated minima and maxima. Accordingly, these can be employed to create typical glucose variations in an individual due to the synchronizing event. For example, if glucose is synchronized based on food intake at lunch, then the post lunch glucose changes will capture typical changes in that individual. Any glucose changes beyond a predefined threshold may have an expected root cause. For example, an inadequate or missed bolus, an insulin stack up effect, and so on.

Trends in glucose patterns (average, high, or low) may also indicate slow changes in behavior that may also be detected and alerted upon. For example, a slow trending of mean glucose or minimum or maximum glucose as determined by machine learning may indicate a change in physiological parameters related to insulin dosing, e.g., insulin to carb ratio or insulin sensitivity. Tuning these parameters with a machine learning algorithm may also be performed using these patterns in cases where different parameters are needed for different times of day, week, or month. Where such trends are determined by the system to be occurring without a corresponding change in user behavior, e.g., as determined by meal data, exercise data, data entered on a user interface, or the like, the algorithm may use such data to estimate or predict that the user is cognitively unaware of the same, and upon such an estimation or prediction a smart alert may be generated and displayed. For example, if the estimation or prediction indicates a likelihood of cognitive awareness of greater than a threshold criterion level (and this is generally true for all estimations or predictions described herein).

These analyses can be run by algorithmic routines in the background while the user is enjoying other functionality of a smart phone, such routines using individual patient data to learn from the data over time in a supervised fashion or an unsupervised one. Thus, over time, pattern recognition may be performed and smart alerts can enable and allow more effective alerting.

As noted above, implementation of smart alerts involves more than simply displacing or delaying alerts in time so as to make the same more convenient to a user. However, the measure of time as determined by timing circuits or algorithms can be used along with additional information such as behavior or context information in the prediction or estimation of user cognitive awareness as well as in the determination of when and how to provide a smart alert. For example, the computing environment may identify an alert state, e.g., a diabetic state warranting attention, but may time when to provide the smart alert based on other input variables, including behavior and context data, i.e., which are in many cases variables that go into the determination of the smart alerts functionality. Even if, on this basis, a smart alert is delayed, the determination of the delay will still be based at least in part on real-time data as noted above.

Behavior and Context Inputs

Various types of behavioral and contextual information may also be employed as inputs into smart alert functionality, to determine, predict, or estimate user cognitive awareness.

Contextual and behavioral information is data that generally corresponds to how a patient uses their mobile device/monitoring app, and thus gives context to certain data determined by the device. Behavior input information may be obtained via the system and can include an amount of interaction, glucose alerts/alarms states, sensor data, number of screen hits, alarm analysis, events (e.g., characteristics associated with the user's response, time to response, glycemic control associated with the response, user feedback associated with the alarm, acknowledgment of alerts or alarms, not acknowledging alerts/alarms within X minutes, time to acknowledgment of alerts/alarms, time of alert state, and so on), diabetes management data (e.g., CGM data, insulin pump data insulin sensitivity, patterns, activity data, caloric data), data about fatty acids, heart rate during exercise, IgG-anti gliadin, stress levels (sweat/perspiration) from a skin patch sensor, free amino acids, troponin, ketones, adiponectin, perspiration, body temperature, user feedback, and the like. The inputs may be provided by a sensor in data communication with the monitoring device. In some implementations, the information may be obtained through an intermediary such as a remote data storage. User data noted above in connection with the user interaction is an example of behavioral data.

Contextual information can include user location, such as determined by a GPS, WiFi, or the location of sharers and followers. The same may relate to a person's biology, location, sensing surroundings (e.g., light, sound level), environmental data (e.g., weather, temperature, humidity, barometric pressure). The inputs may be received via a peer-to-peer or a mesh network via machine-to-machine communication. Context information can include daily routine information (which may change especially from weekdays to weekends) from a calendaring application. Context information can include a frequency of touching or grabbing the monitoring device, even if not interacted with, based on a sensed motion of the device, e.g., from an in-device accelerometer and/or application.

Photos from a user's smart phone can be converted into contextual data using image recognition algorithms. For example, photos of one or more of: a glucose meter reading, an insulin pen or pump IOB, a location (e.g., a gym, park, house, Italian restaurant), or a meal may be used to provide context information. The photos may be processed using image recognition algorithms to identify, for example, caloric intake for the meal shown in the photo. The type of insulin used, which may be determined by a barcode or the like imaged by a smart phone camera, may also be provided to the monitoring system as a useful input to the estimation or prediction of cognitive awareness. Indeed, reception of such insulin type data itself may be indicative of user cognitive awareness, particularly in combination with other data about the same. Context may also be provided by basal or bolus settings provided to or determined by the monitoring device. Such settings may be transmitted to the monitoring device using known data transmission methods and protocols, e.g., Bluetooth®. The transmission may occur on a push or pull basis, periodically, or on another basis.

Behavior/context data may be used in the system's prediction or estimation of user cognitive awareness as the same may indicate a knowledge of the user about their diabetic state. As one extreme, context GPS data may indicate the user is in their physician's office, and thus imply significant user cognitive awareness. At another extreme, behavior data may indicate sleep by way of accelerometer data, thus indicating significant cognitive unawareness. During such times, alerts and alarms may be appropriately modified, e.g., automatically enabled or disabled. For example, if a sleep state is determined, the alerting/alarming system may enter a "night mode" or "sleeping mode" that is more conservative about glucose, and more aggressive with low alarms. Such may then adjust system behavior, including alerting/alarming, and may further adjust target ranges dynamically, significantly enhancing convenience to the user. For example, in such a night mode, the target range may adjust the alarm for hypoglycemia to be more aggressive, e.g., somewhat higher, than in a "day mode". Instigating or initiating these modes may programmatically transform the monitoring device such that its processing occurs in a different fashion than before, enhancing efficiency of the computing device.

Other inputs to the estimation or prediction of cognitive awareness algorithm which constitute context/behavioral data may include certain data types referenced elsewhere, such as exercise information from a fitness bike or the like, glucose sensor information from a blood glucose (BG) meter or CGM, insulin delivery amounts from insulin delivery devices, insulin on board calculations for the device, and other device-provided or calculated information. Other context/behavioral data inputs may include: hydration level, heart rate, target heart rate, internal temperature, outside temperature, outside humidity, analytes in the body, hydration inputs, power output (cycling), perspiration rate, cadence, and adrenaline level, stress, sickness/illness, metabolic/caloric burn rate, fat breakdown rate, current weight, BMI, desired weight, target calories per day (consumed), target calories per day (expanded), location, favorite foods, and level of exertion.

For example, a high outside temperature coupled with low stress and high caloric intake may be determined by the system to be consistent with the user being on a vacation, which may in some individuals indicate a lessened attention to diabetic state. In this case, the system may determine that a user is likely to be not cognitively aware of the diabetic state warranting attention, and thus that a smart alert should be generated.

It is further noted in this regard that a high outside temperature may cause a smart alert to be rendered to the user regarding ensuring that their diabetes supplies are in a refrigerated container and are not exposed to high environmental temperatures.

For any of the above referenced behavior or contextual inputs, the system may be configured to receive and/or generate analytical metrics based on the inputs. For example, a composite value may be generated based on the glucose level, temperature, and time of data generated index value for the user. The composite value may then be considered in the estimation or prediction of cognitive awareness.

This information can be collected from various sensors within or outside of the device, such as an accelerometer, GPS, camera data, and the like, as well as third-party tracking applications, including sleep cycle applications, and may be used to affect outputs, as well. For example, a GPS may be employed to determine a rate of movement, so as to suppress a smart alert on a mobile device if in a moving car. In this context, the smart alert may be transmitted to be rendered on a smart watch, however. Thus, real time measured sensor (glucose) data is used to determine a diabetic state warranting attention, and other data, which may be real time or not (or a combination), is used to determine if a smart alert should be generated. If a smart alert should be generated, then other real-time data, in the above example GPS data, may be used to further determine the form of the smart alert, and in particular the device to which data is transmitted and rendered.

As noted, alerts can be affected by the proximity of sharers and followers. For example, when a sharer is in close proximity to a follower, alerts can become annoying as they may be activated in two locations, e.g., on the sharer's pump, receiver or smart device and also on the follower's smart device. In one implementation, a follower app can detect this situation and delay or suppress the alert on the follower's device. For example, when the follower app receives an alert, it may start an RF, e.g., Bluetooth®, scan for the sharer's mobile device (or dedicated receiver or pump). If it detects the sharer's device e.g., is within 30 feet (for a Bluetooth® detection), it can examine the RSSI (received signal strength) to determine how close (e.g., very near, near, far) it is to the sharer's device. If the follower device determines it is near or very near to the sharer, the follower application can delay the alert for a minute or two to give the sharer a chance to respond. Alternatively, the follower app can suppress the alert. In any case, if the sharer responds within a predetermined time frame, e.g., 1-2 minutes, then the alert may be suppressed on the follower device. Beacon technology may also be employed for this purpose, as disclosed in, e.g., U.S. Pat. No. 8,844,007, granted 23 Sep. 2014 and entitled SYSTEMS AND METHODS FOR PROCESSING AND TRANSMITTING SENSOR DATA; U.S. Patent Publication No. US-2013/0078912, filed 21 Sep. 2012 and entitled SYSTEMS AND METHODS FOR PROCESSING AND TRANSMITTING SENSOR DATA; U.S. Patent Publication No. US-2014/0273821, filed 14 Mar. 2013 and entitled SYSTEMS AND METHODS FOR PROCESSING AND TRANSMITTING SENSOR DATA; U.S. Patent Publication No. US-2015/0123810, filed 5 Nov. 2014 and entitled SYSTEMS AND METHODS FOR A CONTINUOUS MONITORING OF ANALYTE VALUES; U.S. patent application Ser. No. 15/001,756, filed 20 Jan. 2016 and entitled CONTINUOUS GLUCOSE MONITOR COMMUNICATION WITH MULTIPLE DISPLAY DEVICES; and U.S. Patent Application No. 62/271,880, filed 28 Dec. 2015 and entitled INTELLIGENT WIRELESS COMMUNICATION FOR CONTINUOUS ANALYTE MONITORING, all of which are owned by the assignee of the present application and herein incorporated by reference in its entirety.

In some cases, certain unexpected jumps in glucose as determined by analysis of the glucose trace can temporarily disable sharer functionality, to avoid embarrassment to users, and to accomplish user privacy goals and considerations. Such unexpected jumps can include certain health or stress events. In one implementation, a threshold level of an unexpected jump is predetermined, and the data of the unexpected jump is compared to the threshold level to determine if the sharer functionality should be employed to share data about the jump.

Heart rate data measured by a heart rate sensor may be employed in the estimation or prediction of user cognitive awareness. For example, off-the-shelf heart rate sensors may be used with measured results communicated by an appropriate transmission protocol to the monitoring device or other devices providing smart alerts functionality. In another implementation, the sensor electronics or transmitter (see FIGS. 45/46 below) may be equipped with a strong light and an optical sensor (not shown) to detect heart rate. Such heart rate data may be used by itself in the estimation or prediction of user cognitive awareness or it may be used indirectly to infer when a user is exercising, is undergoing stress, is asleep, and so on (which data may then be employed in the estimation or prediction). In a direct such use, a user may be in a diabetic state warranting attention. An accelerometer in a smart device may be used to determine that the device was just operated, and that the operation included viewing of the glucose monitoring app user interface. If the heart rate is suddenly seemed to rise, it may be inferred that the user has been informed of the diabetic state warranting attention, and that no smart alert need be given.

Moreover, context and behavior may also be determined by use of social networking information available about the user, where a social networking feed, associated with the user, is arranged to provide a source of data to the smart alerts functionality. By analysis of such data in a social networking feed, user cognition data may in some cases be determined, e.g., a user posting "I'm low right now." or posting content similar to content posted when previously the user was low. Techniques such as natural language processing may be employed to determine meanings of posts, and thus to allow a quantifiable measure of similarity to prior posts. Thus, posts may be employed not only directly, for their content ("I'm low right now."), but also to infer that the user is in a similar state as when the user previously posted similar comments.

Using such systems and methods according to present principles, the problems encountered by prior monitoring devices, which lacked consideration of such context/behavior aspects, may be effectively addressed. In particular, where available data from sensors and other sources, including context/behavior aspects, allow an estimation or prediction of user cognitive awareness of a diabetic state warranting attention, monitoring devices may be significantly improved by using cognitive awareness as a way to suppress alerts when they are not needed, which provides a significant technological advantage over monitoring devices that base such alerts on thresholds only (or even thresholds plus predictions). Such accordingly provide a significant technological advantage over prior monitoring devices, in which such cognitive awareness was never taken into account. Additional details about context and behavior information may be found in US Patent Publication No. US 2015/0119655, filed 28 Oct. 2014 and entitled ADAPTIVE INTERFACE FOR CONTINUOUS MONITORING DEVICES, owned by the assignee of the present application and herein incorporated by reference in its entirety, and in particular at FIG. 4 and accompanying text.

Behavioral and contextual inputs may also be employed to provide other useful alerting functions. For example, if there are multiple CGM receivers in a household, it becomes important for the users to be able to uniquely identify each one. In order to do this, there are currently no visual aids other than a different colored case to help distinguish the different units from each other. Thus, in systems and methods according to present principles, as part of the setup procedure for a new receiver, or for one that is being used by a new user, the user can be asked to select a unique identifiable mark, such as an initial, screen background, color theme, screensaver, animation, or the like, or a combination, that will be displayed in areas of the screen when displaying CGM information. For example, an initial may be displayed in a corner of the screen or in a status bar. The screensaver may be applied when the screen is not displaying CGM information. The same may be applied to entities such as fonts, backgrounds, and so on. An animation can be displayed in various selectable areas of the screen. In this way, a CGM receiver or CGM smart phone application can display an indicia of the appertaining user when displaying the user's CGM data, thus avoiding confusion when multiple data sources (e.g., hosts with sensors) are transmitting data in a common location at a substantially common time.

Also as part of the set up procedure thresholds may also be set, the user can indicate various types of alerts or alarms that they wish to receive, e.g., a desire to receive alerts after versus before a meal. Smart alerts functionality or the smart alerts app may then be configured to query the user occasionally or periodically post set up, e.g., to determine if the user is satisfied with their set up selections or if they wish to revise them, e.g., to choose to receive alerts prior to meals. Such may also prompt and allow users to revise alert thresholds to better fit their lifestyle, i.e., perform alert optimization.

Other Inputs

Other data sources besides user input, glucose data including derived data such as rates of change and pattern data, and sources of behavioral/contextual data, may also be employed.

For example, data derived concerning signal trends (besides patterns) may also be employed in smart alerts functionality. For example, smart alerts can be based on proximity and duration, e.g., at or near an alertable zone, also termed "hovering". That is, in many cases, even if a user is not in a danger zone, if they are close to one for a long period of time, they want to be alerted. The smart alerts functionality may be employed to provide alerts in this situation. In other words, in a hovering situation, when a user is typically cognitively unaware of their proximity to a danger zone, a smart alert will be generated. In this case, data indicative of hovering may be determined by analysis of measurement data, time duration data, and locations of thresholds. If the user is close to a zone threshold, e.g., +/−10%, for a predetermined duration of time, and if other data discussed above or below indicates that the user is not cognitively aware of the hovering situation, then the smart alerts functionality may cause the generation of a smart alert, where the smart alert indicates the existence of a hovering situation.

In another signal trend, a notification may be provided when a dangerous or undesired range is no longer an issue, thus potentially relieving stress on the user and notifying them that they are once again in target. This is similar to home automation aspects of dimmer switches. In particular, when a dimmer switch is turned off, steps include: light is on, then home automation sends a command to turn off the light, then the lights sends a command that it is starting to turn off the light, and finally the lights sends a command when the light is off. In the same way, in a garage door situation: garage is open, then the home automation system sends a command to close the garage, the garage then sends a command that it is starting to close, finally the garage sends a command when the garage is closed.

For the garage, this functionality is important because if something is blocking the sensor and not allowing the door to close, it is important that the user (through the home automation system) be aware that the garage is not closed. In this case such notification can occur because the user never received the last command. In the present case, if a patient is in hypoglycemia or hyperglycemia, and tries to correct the situation by taking a medical action, the sensor electronics may send a notification indicating that the glucose has inflected and is starting to rise (or fall). The same may then send a notification that the user is no longer in the hypoglycemic (or hyperglycemic range. Rather than waiting for the periodic (e.g., every 5 minutes) measurement to determine if the patient is out of the undesired range, a more proactive approach may be taken to push a notification to announce that the patient is no longer in a undesired range. Thus, in this case, a smart alert can be based on if the second notification is never received. In particular, where the system would properly expect an "out of danger" condition to be determined, where such determination never occurs, the system may infer that the user is still in a dangerous situation and thus that a smart alert should be generated. Such is particularly true where the user has taken a remedial action intended to treat the diabetic state warranting attention. In this latter case, the user may be expecting to emerge from the dangerous situation without a further thought. Where this does not occur, a smart alert may be even more important. It will be understood that this functionality may be accomplished in numerous ways. For example, an "out of danger" notification may take the form of a flag that is set following the detection of the inflection point. The location in time of the remedial action, if known, may also be employed in the calculation, determination, and subsequent setting of an "out of danger" flag. If the user does not emerge from the dangerous situation within a predetermined time duration (determinable from user history and patterns) following the remedial action, a smart alert again may be generated.

Another input can include a user life goal. In particular, diabetes management goals, e.g., reduced hypoglycemic risk, reduced time out of range, reduced alert/alarms, postprandial optimization, rebound reduction, and so on, can be used as inputs to cognitive awareness prediction and estimation. A user may set a goal, or even set different goals for different times of the day, and the system will alter or change settings to enable the user to more easily achieve their desired goal. For example, a person might use a reduced hypoglycemic risk goal at night time, with the system using a predictive low alert with a higher threshold setting. For these settings, e.g., where values are used during nighttime, a user is presumed to be generally cognitively unaware as they are likely sleeping. As another example, such a user may also have a postprandial optimization setting that reminds the user to bolus about 30 minutes before their typical lunchtime, or which provides a reminder to include protein with their meal in cases where an estimation or prediction is made that the user is cognitively unaware.

Other inputs include data and signals from insulin sensors, or from other sources of data about insulin. For example, insulin sensor data can be used to detect insulin delivery, which in turn provides a way of estimating cognitive awareness of a diabetic state warranting attention, based on an estimation of when the insulin was injected. In more detail, if a hyperglycemic diabetic state warranting attention occurs, but the smart alerts functionality app uses data from an insulin sensor to detect that there is a degree of insulin on board, then the smart alerts functionality may suppress an alert until such time as it is determined that the current insulin is no longer able to control the hyperglycemia and that the user is not cognitively aware of a need for more. Insulin sensor data may be put to other uses as well. For example, besides insulin on board, information about timing of boluses may be employed to modify the behavior of smart alerts for both hypoglycemia and hyperglycemia. For example, if a user has recently taken a bolus of insulin, threshold alerts could be delayed, or predictive alerts could have their target threshold temporarily suspended or elevated, based on a recognition of likely user cognitive awareness and/or lessened user danger from the situation, e.g., lessening the danger of the "diabetic state warranting attention". As a particular example, if a prediction was used at 200 mg/dL, then knowledge of a bolus could set the alert to 250 mg/dL for one hour. Similarly, for a low glucose alert, knowledge of insulin could increase or decrease the sensitivity of the alert if the calculation suggests that the amount of insulin suggests a more modest or aggressive glucose drop.

Generally use of insulin sensor data in this context requires a degree of machine learning, particularly as each user has a different insulin sensitivity, and this sensitivity may change over time. Thus, knowledge of current insulin sensitivity can be a prerequisite for use of insulin sensor data, particularly when a high degree of accuracy is needed.

As another example, if information or data is known about insulin on board, or is subsequently or contemporaneously entered by the patient, the same may be used in the determination of when to provide smart alerts. Such information about insulin on board may be entered by the patient or received from a medicament delivery device, e.g., pump or pen. In one implementation, the user may input how much insulin they have taken, and then a calculation may be made as to how much insulin is remaining in their system over the next several hours. The insulin on board value may then be employed to notify when a patient is notified, e.g., is alerted or alarmed. In one implementation, if the patient normally wants to be alerted when they go above 200 mg/dL, and the system detects that they are above that value, or predicts that they will go above that value, the system may then determine or receive data about the insulin on board. If they have a lot of insulin in their system, e.g., five units, then the system may determine that the patient need not be alerted immediately, because the insulin would be taking care of the potential hyperglycemic condition. Similar steps may be taken as the patient approaches hypoglycemia. For example, if the patient desires to be notified if they drop below 80 mg/dL, and the system detects that they are above this value, but have a significant level of insulin in their system, then the system, i.e., with smart alerts functionality, may be caused to alert the user earlier that they are heading low.

Another potential input includes type of diabetes and the particular manifestation of diabetes for a given user. The cognitive awareness of a type I patient may be different from the cognitive awareness of a type II patient. Thus, the generation of a smart alert may differ between the two, and the timing of the alert may similarly differ. In one implementation, the difference between the two situations is limited to the threshold level at which the estimation or prediction determines cognitive awareness. In other words, the threshold level is altered between the two types of diabetes, the threshold level being that which is compared to the estimated or predicted cognitive awareness, and which results leads to the generation (or not) of a smart alert.

Other different and individualized physiology and pattern effects may be seen. For example, it may be common for a patient to hover around 70 mg/dL, but it may be very uncommon for that same patient to suddenly decelerate after they pass through 60 mg/dL. In this example, by determining the glucose concentration value and including in the estimation or prediction the rate of change of the same, an atypical response may be detected and alerted upon.

Systems and methods according to present principles, incorporating cognitive awareness in the determination of whether to alert users, are customized and/or two and for each individual user, and the customization/tuning occurs by machine learning, e.g., using data and sources noted above. Other significant sources of customization or personalization include varying the operation of the smart alerts functionality based on physiology, age of the patient, exact diagnosis, and so on. Thus, implementations of systems and methods according to present principles provide a significant advantage in the reduction of burden on the user or clinician, e.g., of setting alarm and alert thresholds, which in some cases are not even knowable because of day-to-day variations. That is, in many cases, there is simply no way for a user to figure out how to customize their alerts without the technological advancement of present systems and methods and their subsequent prediction or estimation of cognitive awareness.

In other variations, systems and methods may create multiple profiles for a patient, depending on activities, illness, pregnancy, menstruation, other cycles, and so on.

Yet other data sources may include telemetry, metabolic rate, and so on. Still other potential data and data sources may include correlation data (such as user cognition at night versus during the day), pain data, heart rate variability, stroke volume, cardiovascular health, ability to distribute insulin, body temperature (which affects insulin absorption rate), insulin type (based on insulin sensitivity measurements, profiles, peaks, time between peaks), atmospheric pressure (which affects CGM and insulin absorption), insulin sensitivity, determinations as to which factors bear most heavily for a given user, e.g., exercise versus meals, health or physiological conditions known to affect certain parameters, illness, whether a smart device is in a particular mode such as airplane mode, exception management (e.g. to identify what is normal for a particular patient and to run exception management rules), whether the smart device running the smart alerts functionality is in a training mode, clinician set up parameters, response triggered data, and so on. Thus, user cognition may relate not just to whether a user is aware of a high or low, but also whether the user is encountering a situation with a highly complex response that the user simply cannot be cognitively aware of due to its inherent complexity.

For any given input, fuzzy logic may be employed in the determination of the value of the input. In some cases, fuzzy processing may also be employed, as well as fuzzy outputs. In more detail, alerts or alarms, including smart alerts and alarms, can be triggered in a way that does not rely solely on the glucose value crossing a numeric threshold. In one implementation, an algorithm may be employed that triggers an alert when a user's glucose value is hovering just below a high alert threshold or just above a low alert threshold for a given predetermined duration, even if the threshold is not crossed. This implementation is similar to the hovering implementation described above. For example, a user's high alert threshold may be set at 180 mg/dL, and the user's consecutive glucose values may be 178 mg/dL, 175 mg/dL, 177 mg/dL, and 178 mg/dL. While the user's glucose value never reaches 180 mg/dL, the algorithm recognizes the proximity of the glucose value to the threshold and provides a smart alert to the user after 20 minutes (or after some other duration which may be configurable by the user). Such implementations are useful because the user may be prompted to take corrective action, e.g., a small insulin bolus or exercise, when the user would otherwise not have paid attention to their glucose value. In another implementation, an algorithm may be employed that attenuates the alert/alarm when the user's glucose value is crossing back and forth over the alert threshold but with a small rate of change. As an example, a user's high alert threshold may be set at 180 mg/dL, and the user's consecutive glucose values may be 170 mg/dL, 178 mg/dL, 182 mg/dL, 179 mg/dL, 181 mg/dL, 178 mg/dL, and 182 mg/dL. An alarm would be triggered at the transition from 178 mg/dL to 182 mg/dL, but if the user acknowledged or dismissed that alarm, the alarm would not be triggered again at the subsequent transition from 179 mg/dL to 181 mg/dL. Such an implementation may be particularly useful because it helps avoid the annoying situation users face when they are aware of the borderline glucose value and do not want or desire or need repeated alerts. In some implementations, use of this technique may be more safely performed at the high alert threshold then at the low alert threshold.

Other variations may include variations in a frequency in which input data is received or output data is displayed. In particular, systems and methods according to present principles may be configured to receive additional data, e.g., by updating more often, when a dynamic risk is on the horizon, e.g., updating every minute instead of every 5 minutes. For example, if an impending low is predicted based on a current glucose level and glucose rate of change, then the display may update every minute instead of every 5 minutes. In such an implementation, more advanced information may also be displayed, such as an indication as to whether a rising or falling glucose trend is accelerating. More advanced visuals may also be employed to indicate this deduced, calculated, estimated, or predicted information. In this way, the user is provided with better and more frequent information when they need it most. And by use of the most accurate information, the system may be enabled to even further suppress alerts, e.g., in cases where a dangerous situation is fixing itself. In this way, user annoyance at unnecessary alerts is further avoided.

As another example of an input to the estimation or prediction of cognitive awareness, signal metadata may be employed. For example, inflection points may be used which, once determined, cause a focusing on the area of inflection. As a particular example, the system can sample more often at inflection points than at non-inflection points. Such inflection points may include points at which a glucose signal is turning around or other such points where fine tuning or additional data may be useful in determining parameters helpful to a user, including parameters determinative or useful in determining user cognition of diabetic states warranting attention. The benefits are as noted above. It is noted in this regard that sampling more at such points allows sampling less at different points, and sampling less at different points may be particularly useful in saving battery life, reducing power requirements, sensor and monitor life, and so on. More frequent sampling and subsequent transmission of data for rendering may also be employed in situations where the user is nearing or is in hypoglycemia or hyperglycemia. In other words, such as zones may be used as the inflection points noted above.

Inputs may be received in some implementations from wearable sensors. In one implementation data available from a smart watch may be used either on a standalone basis or to augment other data. In a particular example, sensors and signals collected by smart watches such as the Apple watch and the Microsoft Band may be employed to augment detection of hypoglycemia. Such signals can include those from heart rate sensors, sympathetic/parasympathetic balance (which can be inferred from heart rate), perspiration/emotion/stress from conductance sensors, and motion data from accelerometers. Such signals may be used in addition to the CGM signal. The algorithms used to process these auxiliary signals can be trained on the patient's own data, using CGM to assist in the training. These algorithms can be optimized off-line, e.g., in the cloud. Then detection criteria can be sent to the patient's smart phone and/or smart watch. There may be instances when CGM fails to detect hypoglycemia, but when augmented with auxiliary signals indicating possible hypoglycemia, the patient may be alerted to the suspected hypoglycemia and thereby enabled to avoid the consequences. Alternatively, after the algorithms used to process the auxiliary signals have been trained, the smart watch signals may be able to detect hypoglycemia without the use of CGM. In this use case, adjustments to the algorithms may be necessary to optimize sensitivity or specificity.

In other implementations, smart watch sensors and machine learning may be employed to detect and quantify sleep. For example, if a user is asleep, as determined by motion data from an accelerometer, it may be inferred that the user is not cognitively aware of a diabetic state warranting attention, or indeed any diabetic state. Thus, alarm variations may be configured to not suppress any smart alerts if the system estimates or predicts that the user is sleeping. Other sleep sensors may also be employed in the estimation or prediction of cognitive awareness.

As an example of an alternate type of sleep sensor, temperature may be employed as a mechanism to determine whether or not a patient is sleeping. For example, such sleep sensors may be employed to observe times awake versus times spent sleeping. In implementations, a temperature sensor mounted on the skin, which may be a separate temperature sensor or one implemented within the adhesive patch attached to the patient, may take advantage of a strong correlation between temperature data and time spent asleep.

Still other inputs will be understood as disclosed in U.S. Patent Application Ser. No. 62/289,825, filed 1 Feb. 2016, and entitled SYSTEM AND METHOD FOR DECISION SUPPORT USING LIFESTYLE FACTORS, owned by the assignee of the present application and herein incorporated by reference in its entirety.

Outputs

The output of the smart alerts functionality is generally a displayed output, but the algorithm itself may have an "output" in the sense of a calculation, estimation, or prediction of user cognition, and thus the causing the suppression of an alert or simply causing the generation of an alert step to not occur (if, e.g., the user is estimated or predicted to be cognitively aware of the diabetic state warranting attention) are also considered "outputs" in this sense.

The output of the smart alerts functionality may also be in a number of forms, e.g., a visual display, an audible indication, a tactile indication, and so on. Such may be combined in various ways to support smart alerts functionality. For example, a visual display may be employed to provide an indication of the diabetic state, but an audible or tactile indication may be provided according to smart alerts functionality based on cognitive awareness. Alternatively, a visual display may be employed to provide an indication of the diabetic state (e.g., a value and a trace graph), but another visual display, e.g., overlaid on the first, may be employed to provide a smart alert. In another implementation, a prompt on the display may be employed and used to test for user cognitive awareness, and if such indicates the user is cognitively unaware, then a smart alert may be generated. How the prompt and its response indicates cognitive awareness may vary. The prompt on the display may be explicit, asking the user if they are aware of an impending diabetic state warranting attention, or may be more subtle or implicit, requesting lesser information, but which would provide data necessary for the estimation or prediction of cognitive awareness. Such implicit or subtle prompts or questions may be more appropriate for younger users or less experienced or sophisticated users, or those who have less experience with the biological symptoms of diabetic states. Thus, systems and methods according to present principles may use user profile information in the determination or calculation of what types of prompts or questions to render on a user interface.

The resulting rendered user interface in the output of the smart alerts functionality is strongly tied to the calculated estimation or prediction of user cognitive awareness. If the user is predicted or estimated to be cognitively aware of the diabetic state warranting attention, then the user interface will generally not display a smart alert. Conversely, if the user is estimated or predicted to be not cognitively aware, then the smart alert will be displayed, and the same will generally involve an alteration in the user interface. Such an output is generally believed to be far more effective and efficient for users then alerting based only on thresholds, for the reasons given above, e.g., as smart alerts cause less re-alerts, less alert fatigue, and so on. The same further allows significant savings of battery power and computing cycles.

In a given rendered output, the smart alert may further be displayed along with an expression of confidence or doubt. The level of confidence or doubt may be calculated by systems and methods according to present principles based on error bars calculated for data, known or determined calibration ranges or errors, known or determined sensor errors, or the like. The confidence or doubt may be expressed to foster trust between the user and the system. This trust is heightened when the system has performed additional machine learning steps, and has obtained enough data to make accurate, highly personalized suggestions and recommendations for a user. At such a time, systems and methods according to present principles may reduce the display of expressions of doubt in the smart alerts output, as the same are no longer or less pertinent. As a particular example, a low alert that occurs during a possible artifact (e.g., a "dip and recover" fault) may be expressed with a degree of doubt. An insulin dose recommendation may be made to account for the uncertainty in the glucose estimate. Such may occur during, e.g., day one of a CGM session. The recommendation expresses this uncertainty to the user in a way that in turn fosters trust in the monitoring app and smart alerts functionality, because the user is aware that the system is making a "guess" or prediction rather than making an unequivocal recommendation. In this way, the smart alert engages the user and fosters trust in the system. Later, after the fault is no longer present, the monitoring app and smart alerts functionality may express data without a degree of doubt, or with a lessened degree of doubt, heightening confidence in the monitoring app, not just in its accuracy but also in its error awareness and handling.

Where a smart alert is generated and displayed, the same may be configured on the user interface to be minimally intrusive to the user, and may be such that the rendering of the glucose value itself is deemphasized while trend information, e.g., achieved by rendering on the display or screen various arrows or zones, is emphasized. Such may be implemented by a control setting, adjusted by a physician or by the user, that adjusts the rendering of the display to focus on trend or trend arrows, with a less visible glucose number.

Aggressiveness of the smart alerts functionality can be tuned by user-configurable settings, e.g., slider bars. The slider bars can affect not only the inputs but also the outputs. That is, slider bars may be employed to affect the operation of the smart alerts functionality on the input side and also on the output side. For a user who desires settings with high aggressiveness, more smart alerts will generally be provided than for users who desire a lesser degree of aggressiveness. Put another way, if the user interface setting is set at a high degree of aggressiveness, the system may automatically control a threshold level of cognitive awareness (on which smart alerts are based) to be higher. If it is higher, more smart alerts will be generated, as the threshold level for cognitive awareness is more difficult to attain. In this way, the system becomes more aggressive. Conversely, if the user controls the user interface setting to be a lower level of aggressiveness, the threshold level of cognitive awareness may be decreased, causing fewer smart alerts.

Figure 8:
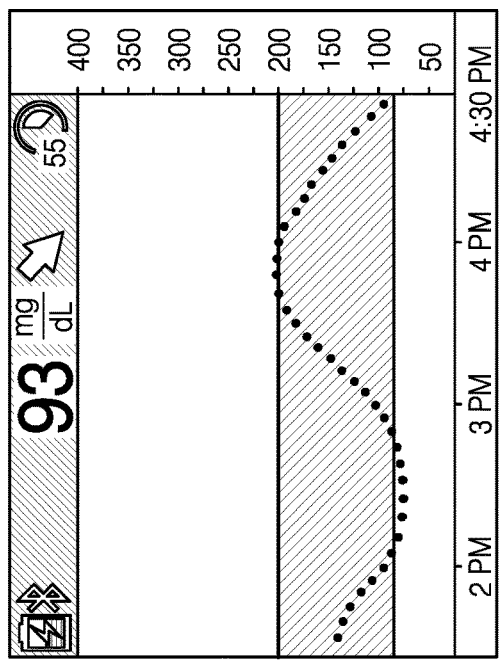
FIGS. 7 and 8 show a smart alert (FIG. 7) and a glucose trace atop which the smart alert appears.
Figure 7:
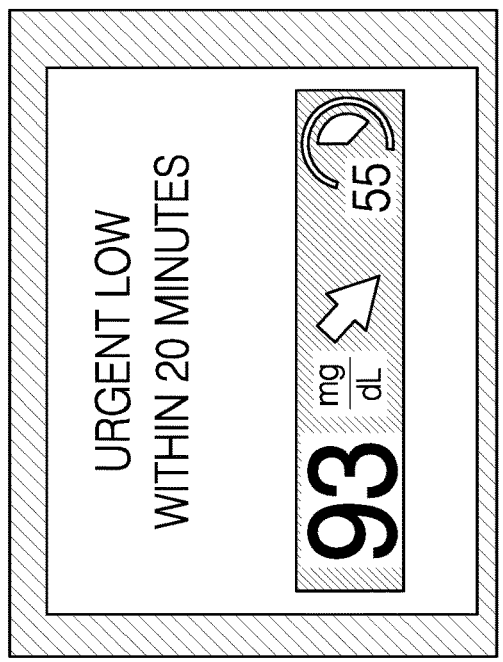
Figure 10:
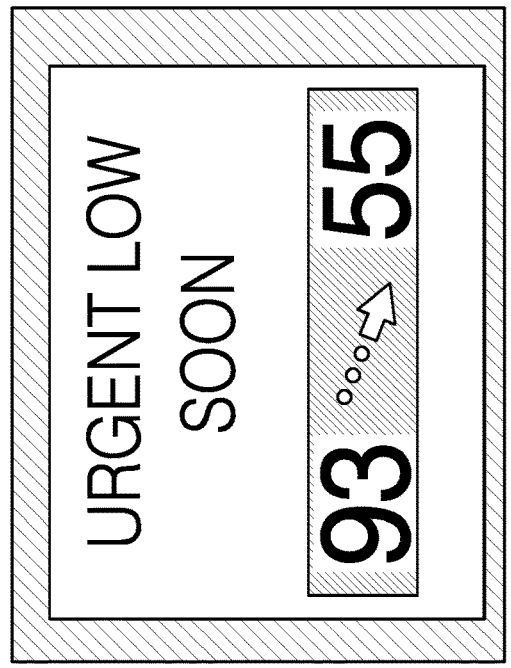
FIGS. 9-14 illustrate additional implementations of smart alert outputs on a user interface according to present principles.
Figure 9:
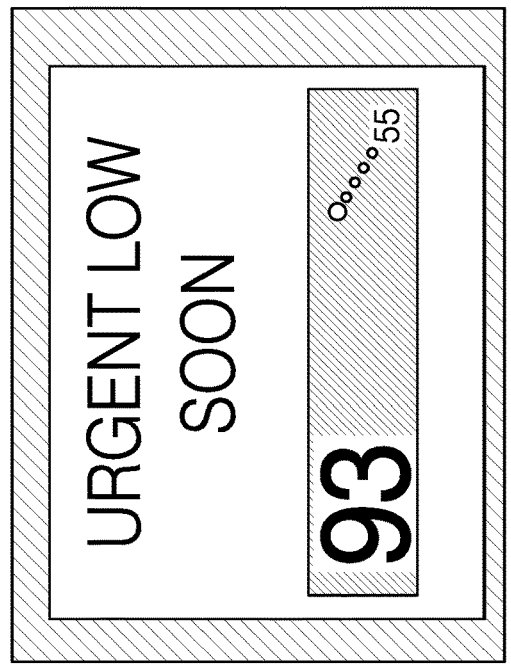

Dynamic risk may play a role in how rapidly input data is accumulated. Dynamic risk may also play a role in how often data is updated, providing a more granular and accurate way for a user to receive notification of and assessment of their risk. This risk may be measured by a suitable calculation based on glucose value and rate of change, or may include more advanced calculations such as including glycemic urgency index as described in the patent application incorporated by reference above. That is, based on a dynamic risk calculation, which can include glucose value, glucose rate of change, and other more complex derived values (generally involving one or more of these real-time values), the system can automatically adjust data transmission settings, e.g., frequency, whether pushed or pulled data is used, screen refresh rate, data updating and recalculation rates, calibration frequency, and so on.

Where smart alerts are generated and rendered on a display and more particularly on a user interface rendered on the display, they may take a number of forms including having various levels of prediction. For example, referring to FIG. 7, a smart alert may indicate a diabetic state warranting attention and may further provide details of current glucose values, expected glucose values, e.g., expected within a certain timeframe, e.g., 20 minutes, and so on. The smart alert, shown in FIG. 7, may be overlaid on top of a trace graph, the trace graph indicated in FIG. 8. As may be seen, the smart alert of FIG. 7 provides a detailed alert to a user who is not cognizant of their diabetic state warranting attention, in this case of an impending low (shown by the local minima of FIG. 8).

FIGS. 9-29 illustrate exemplary user interfaces and smart alerts, which have been constructed based on considerations of interface usability and other factors. For example, while the use of displayed arrows is sometimes helpful to users, their meaning is on occasion not clear. For example, arrows tend to convey a sense of urgency, or a need to take action, but users may be confused about whether the arrow is referring to a prediction or a trend. Thus, in one implementation, it has been found useful to display on the user interface a current value of glucose, a threshold alert level, e.g., the most relevant threshold alert or alarm level given the current value of glucose, e.g., '55', a symbol, and a color, e.g., yellow or red in the case of a diabetic state warranting attention for which the user is cognitively unaware, the particular color depending on the urgency of the state.

Figure 12:
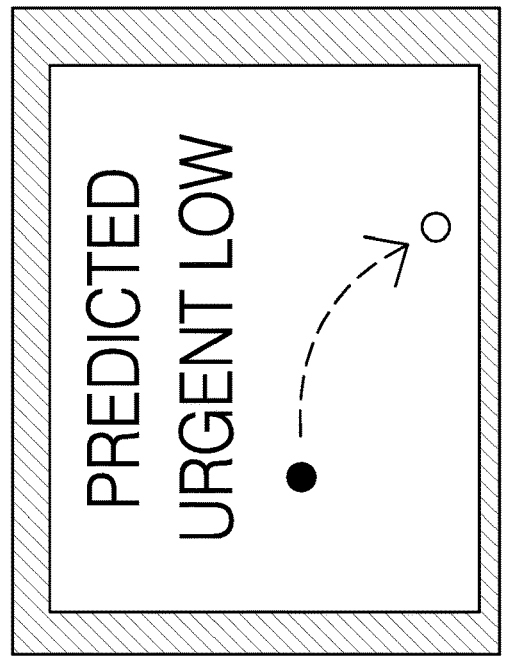
Figure 11:
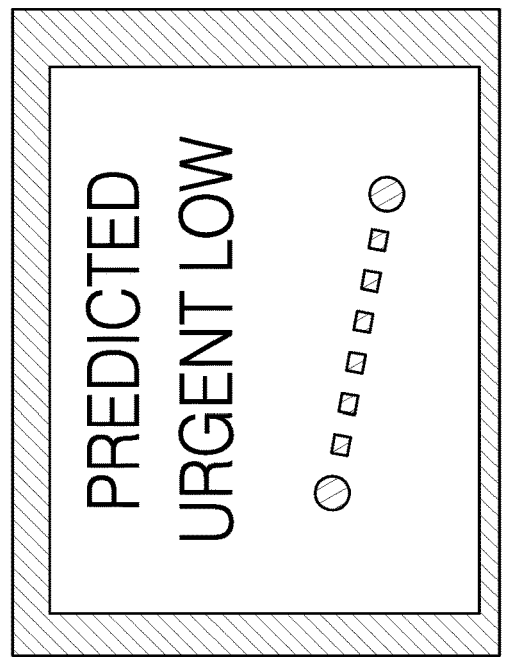
Figure 14:
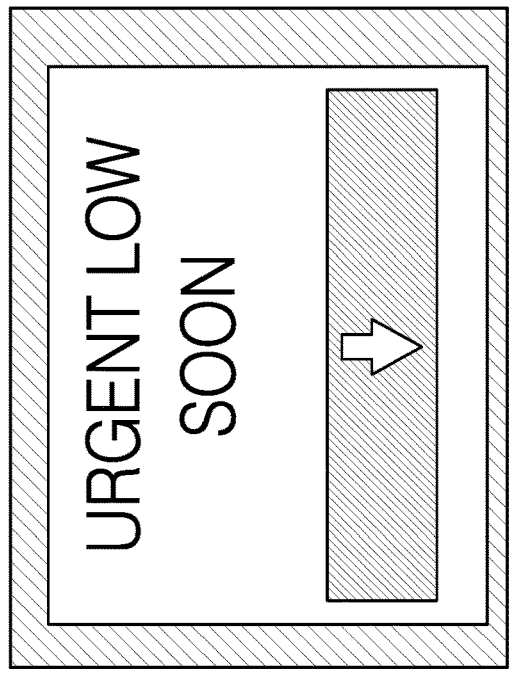
Figure 13:

The symbol may be as indicated in FIGS. 9-14, e.g., a dotted line starting at a bolded point and terminating at a threshold value (FIG. 9), a dotted line with an arrowhead indicating direction (FIG. 10), a dotted line which, if read from left to right, indicates a direction (FIG. 11), a line segment with an arrowhead indicating directionality (FIG. 12). In some cases, e.g., for sophisticated users, just a warning is necessary, and such is shown in FIG. 13. A warning with a trend arrow and color indicator are shown as an alternative user interface in FIG. 14. All of these elements, and their combination, are useful in providing context to the smart alert. Symbols may be particularly convenient for use with children, as the same are more readily identifiable and easy to communicate to parents.

As can be seen in FIGS. 9-14, the smart alerts are generally provided as an overlay above another user interface, which is typically associated with a CGM monitoring application. Thus, the overlay is often above a trend graph, which may or may not include a predictive element, sometimes indicated by an arrow or dotted line. In general, it has been found that the appearance of two different arrows on the screen may be confusing to users, and thus if a trend arrow appears in a smart alert, the same should not appear or should be suppressed in an underlying glucose trace chart.

Figure 16:
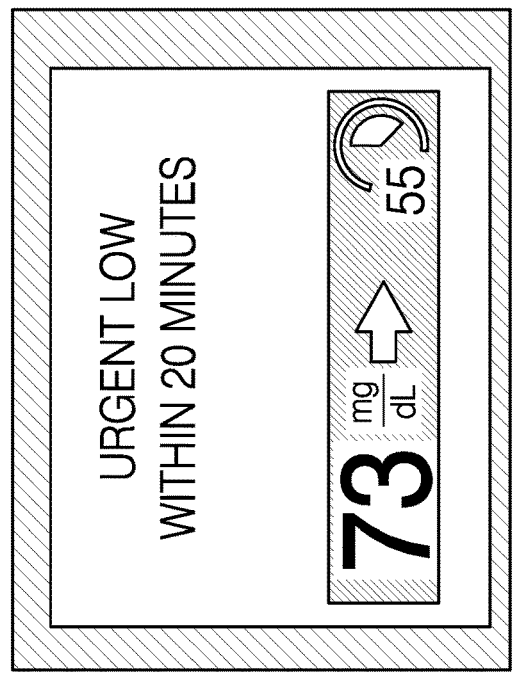
FIGS. 15-17 illustrate yet additional implementations of smart alert outputs on a user interface according to present principles.
Figure 15:
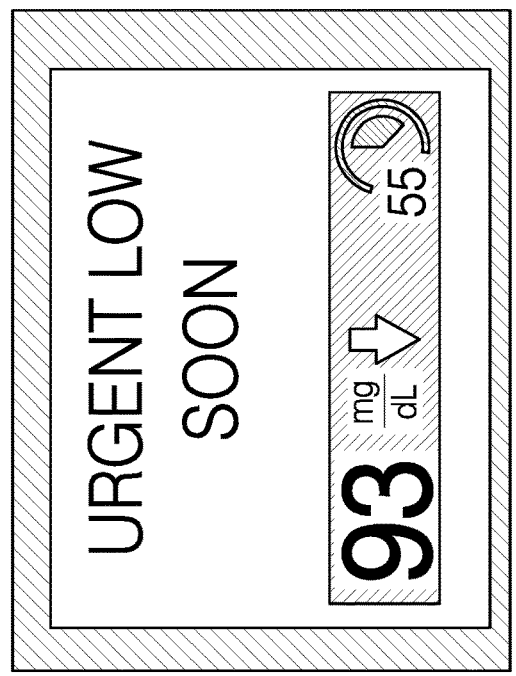
Figure 17:
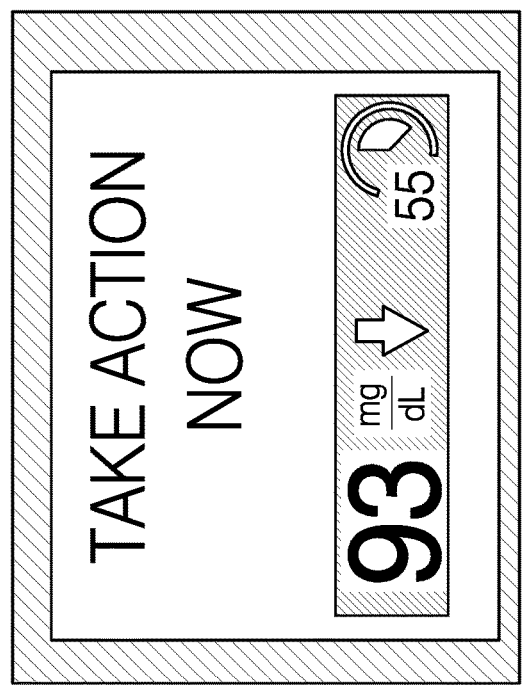

It has also been found beneficial to indicate an endpoint of the trend, and such is indicated in FIGS. 15-17. This endpoint may indicate a time (quantitative, such as "within 20 minutes", or qualitative, such as "soon"), a value, or both. In FIGS. 15-17, the time portion of the endpoint is indicated by a segment on a clock indicating 20 minutes, as well as qualitatively or quantitatively within the textual warning itself. The value portion of the endpoint is indicated by, in this case, a low alert threshold, e.g., 55 mg/dL. A current value is also shown in FIGS. 15-17, along with a trend arrow and a color indicator. The color indicator is generally based on the urgency of the smart alert, as determined by the current glucose value, its rate of change, and the like.

Figure 19:
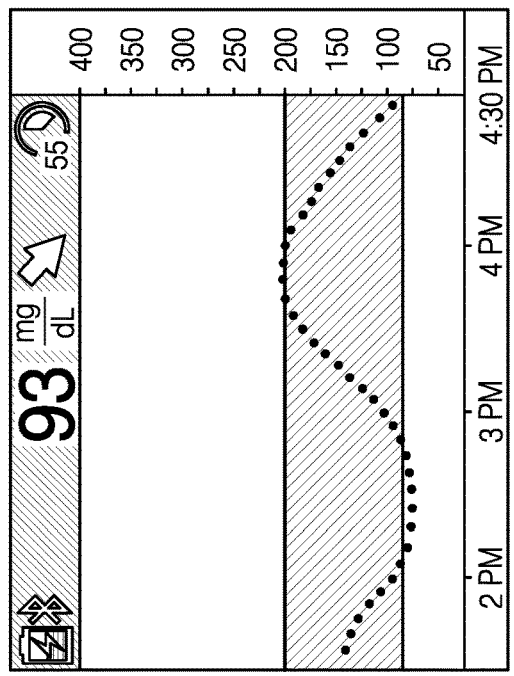
FIGS. 18-21 illustrate additional implementations of smart alerts and respective glucose trace charts on which the smart alerts are overlaid.
Figure 18:
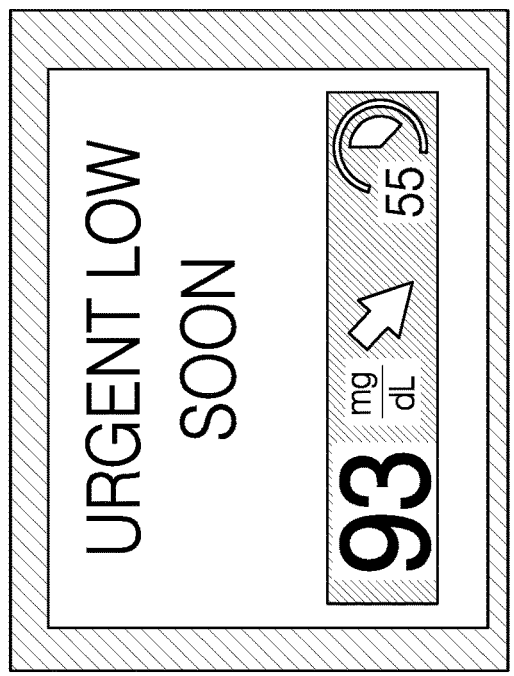
Figure 21:
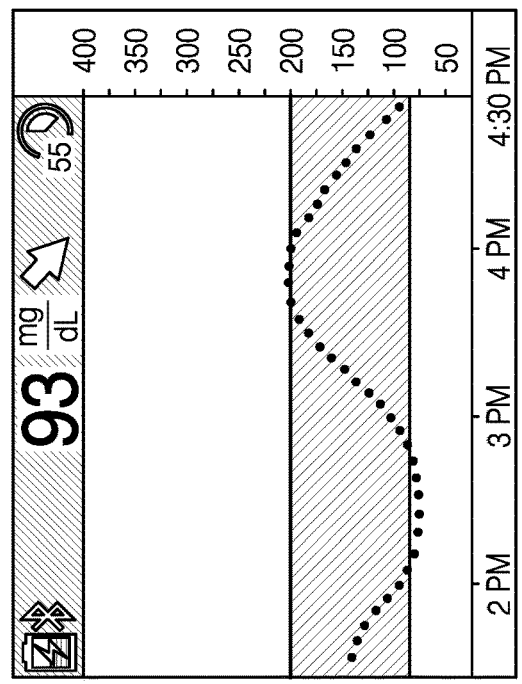
Figure 20:
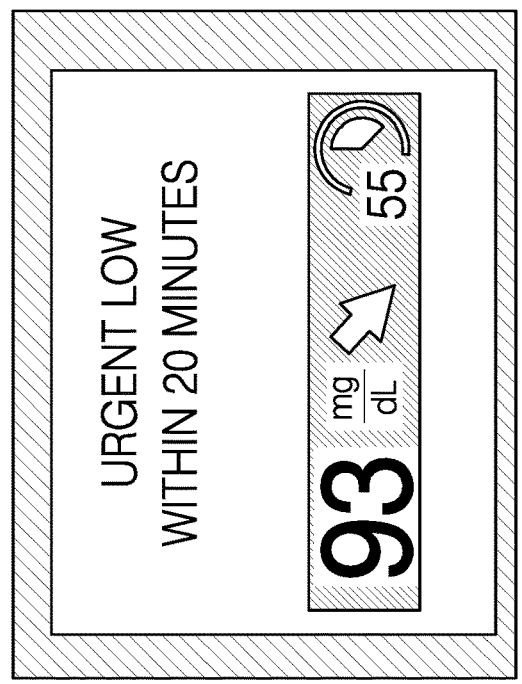

FIGS. 18 and 19 indicate a glucose trace chart (FIG. 19) and a smart alert overlaid on the same (FIG. 18) and similarly FIGS. 20 and 21 indicate a glucose trace chart (FIG. 21) and a smart alert overlaid on the same (FIG. 20). These figures show a smart alert that has been found beneficial, and the same includes a textual warning "urgent low soon", a current value of glucose, i.e., 93 mg/dL, a trend arrow, an indication of the relevant threshold, i.e., 55, and a time indication indicated by a clock segment. FIGS. 20 and 21 further include an indication of the time endpoint within the textual portion of the smart alert warning.

Figure 23:
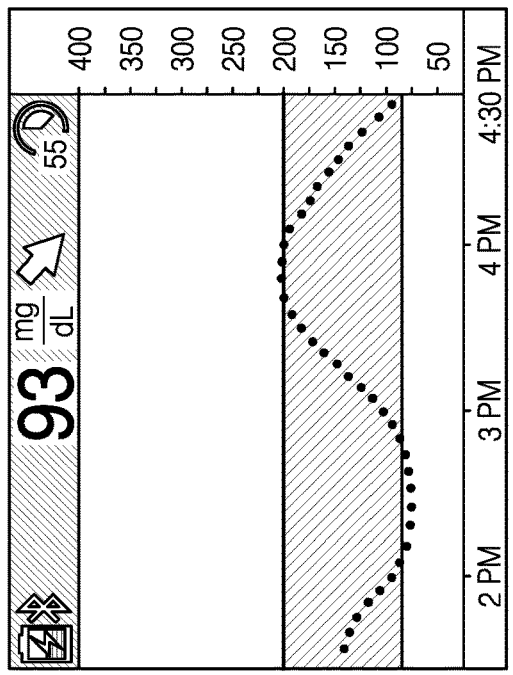
FIGS. 22-29 illustrate a time progression of smart alerts according to present principles.
Figure 22:
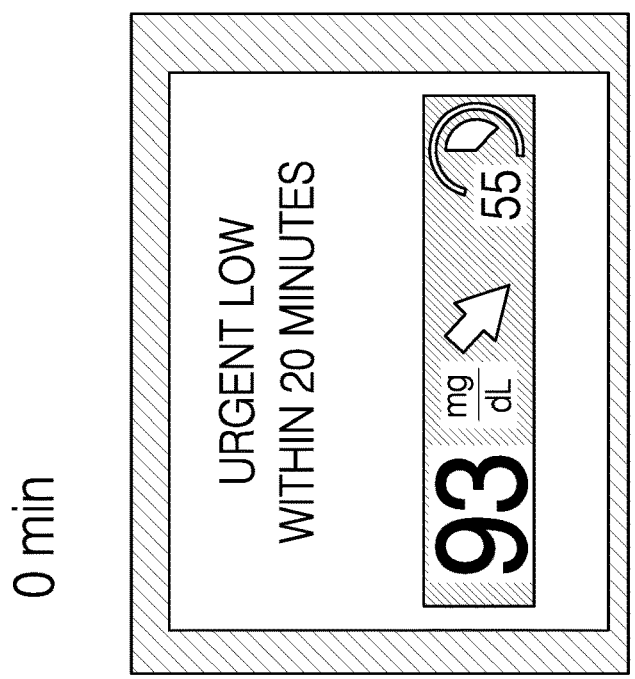
Figure 25:
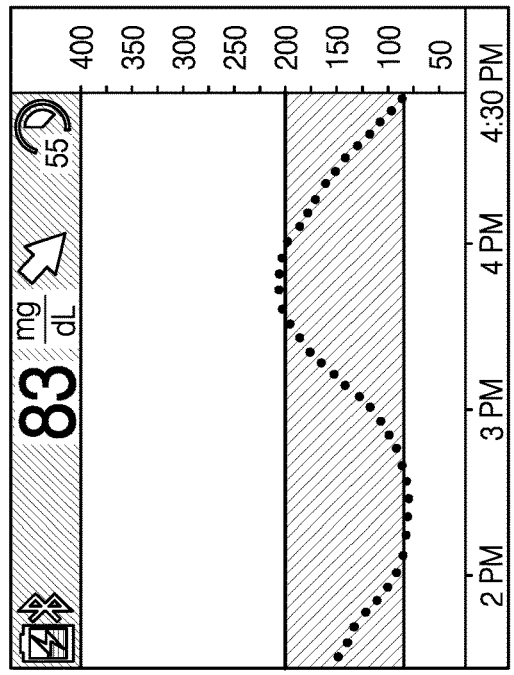
Figure 24:
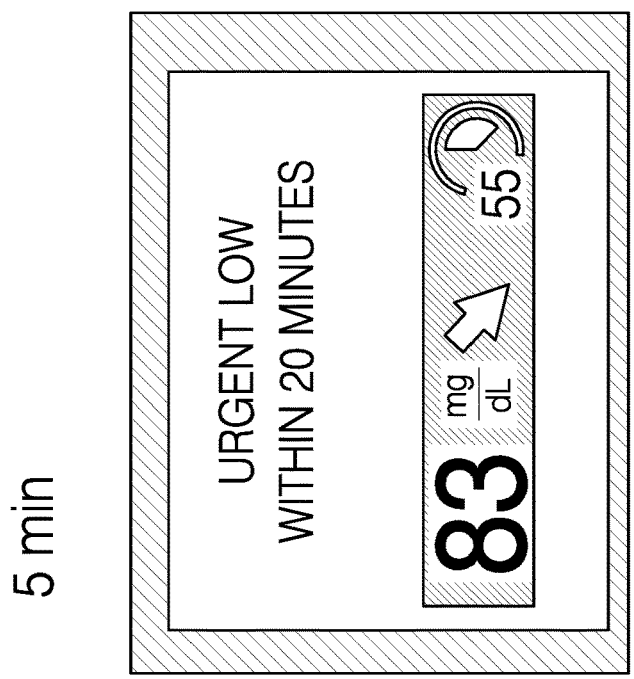
Figure 27:
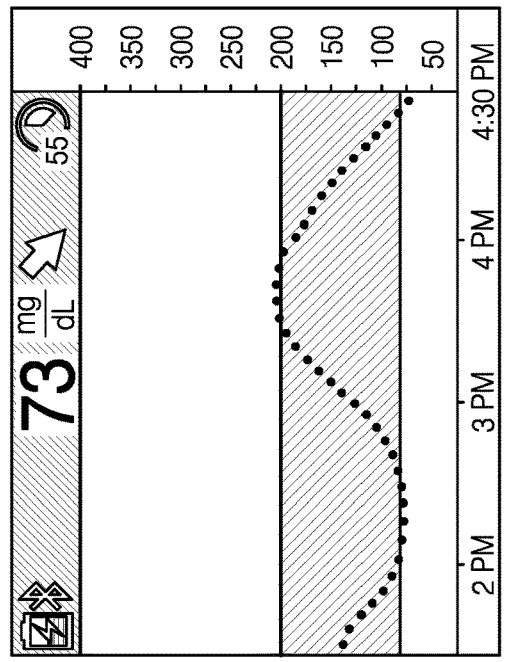
Figure 26:
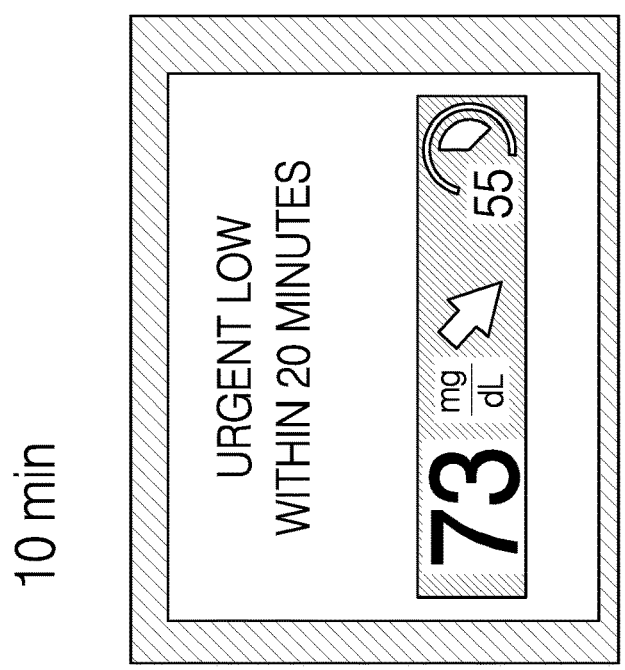
Figure 29:
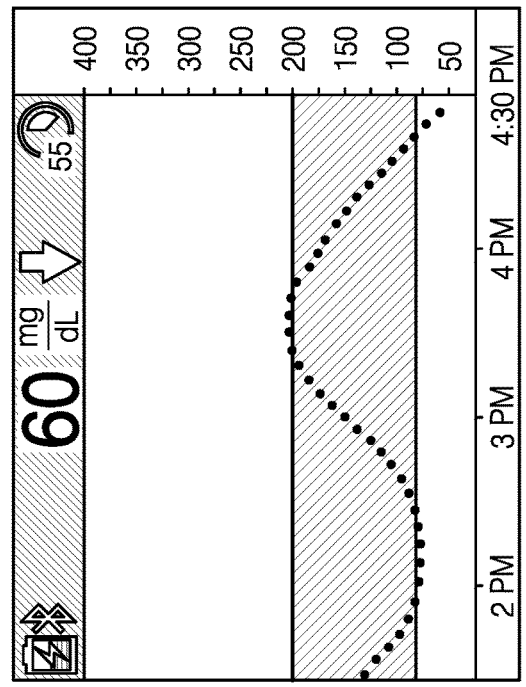
Figure 28:
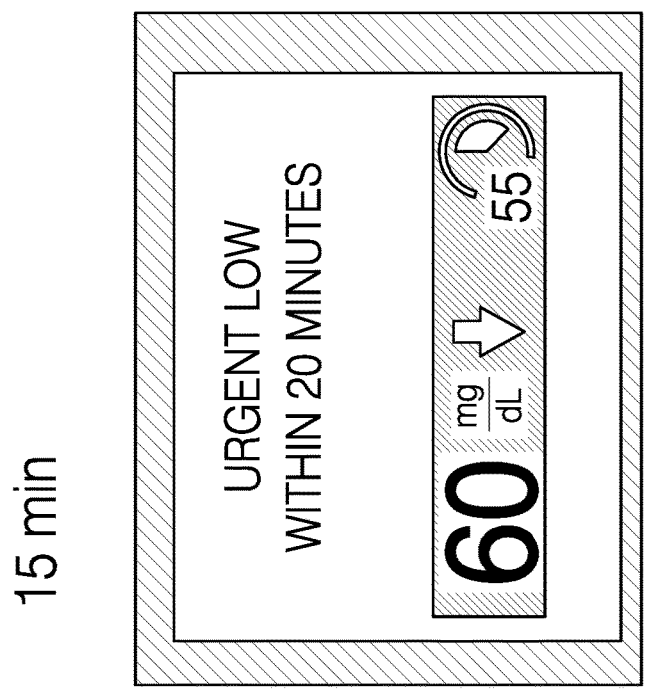

In many cases, as illustrated by FIGS. 22-29, it has been found advantageous to display quantitative time-based warnings rather than qualitative ones. FIGS. 22-29 illustrate a time sequence of smart alerts, showing a time progression over a 15 minute time span. FIGS. 23, 25, 27, and 29 show underlying glucose trace graphs, and their respective smart alerts are shown by FIGS. 22, 24, 26, and 28. An initial time point is indicated by FIGS. 22-23, with a time point 5 minutes later shown by FIGS. 24/25. A time point 10 minutes later is shown by FIGS. 26/27, and a time point 15 minutes following the first is shown by FIGS. 28/29.

As noted above, the use of the color red has been found beneficial in the provision of smart alert. However, the same may be modified based on the urgency of the smart alert. For less urgent smart alerts, for example, a lighter shade of red may be employed.

Figure 31:
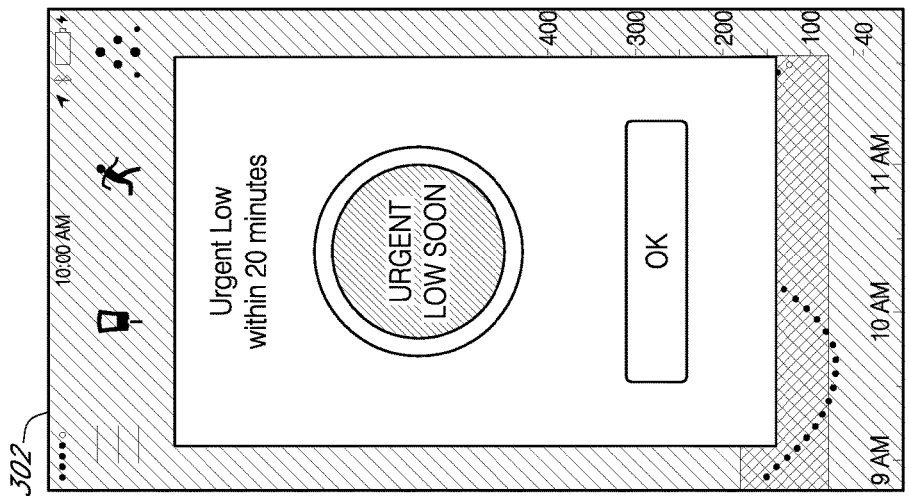
FIGS. 30-41 illustrate implementations of smart alerts as part of a lock screen on a smart phone.
Figure 30:
Figure 32:
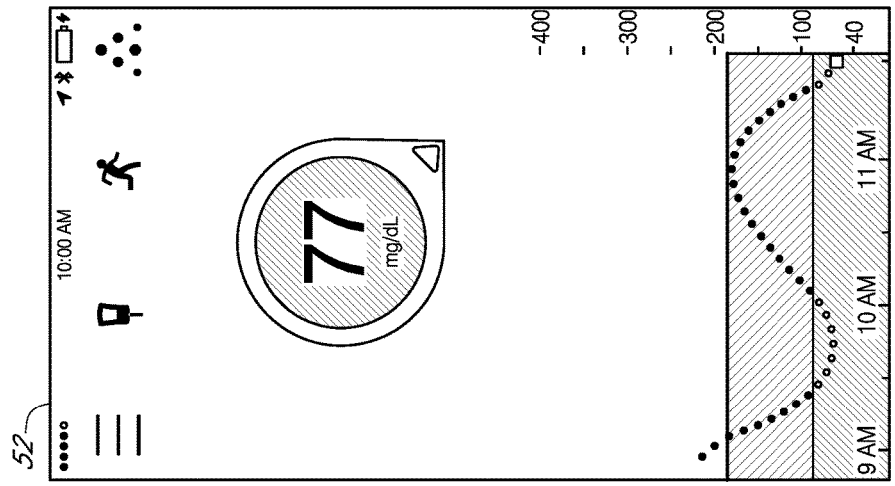
Figure 33:
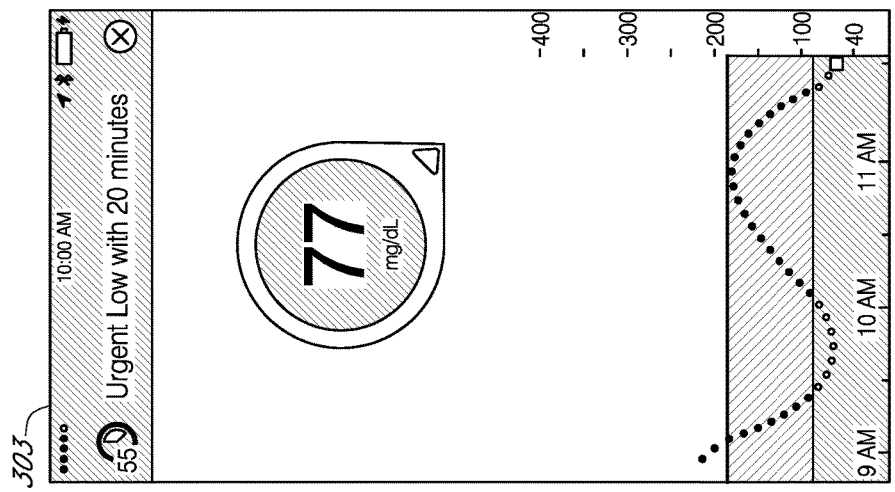
Figure 35:
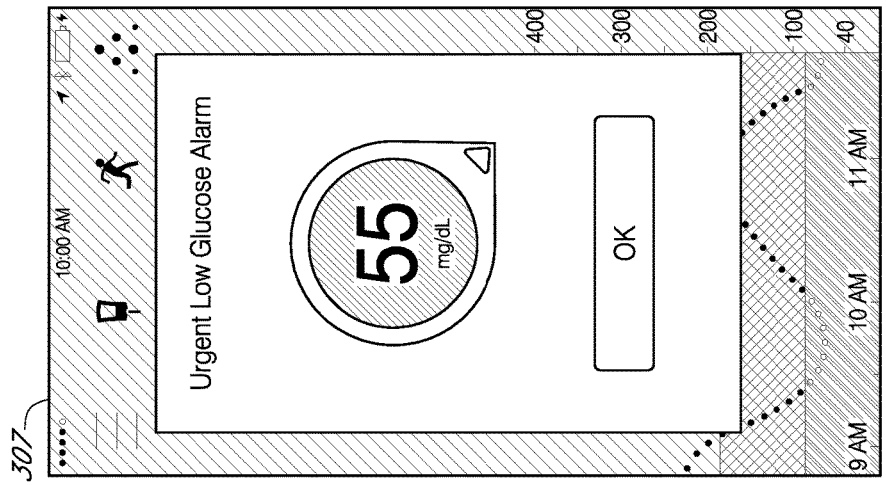
Figure 34:
Figures 36, 37:
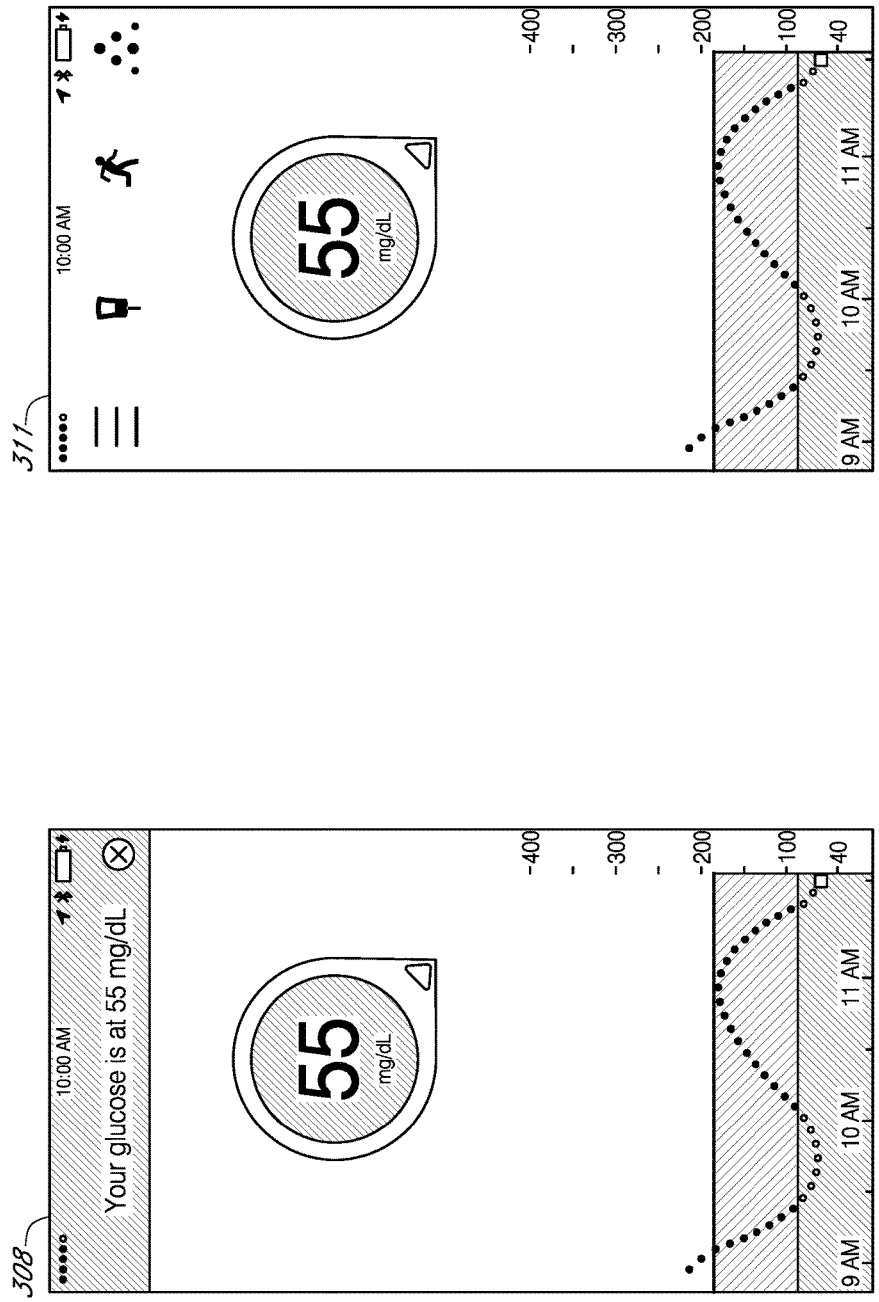
Figure 39:
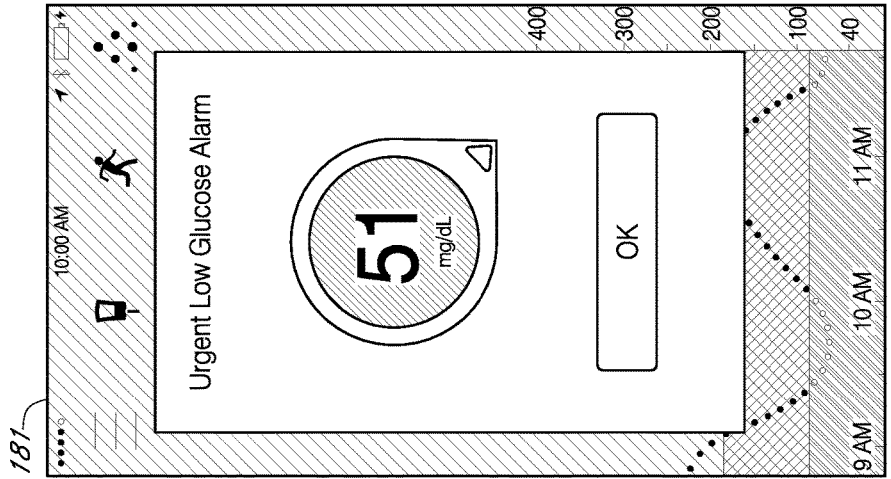
Figure 38:
Figure 41:
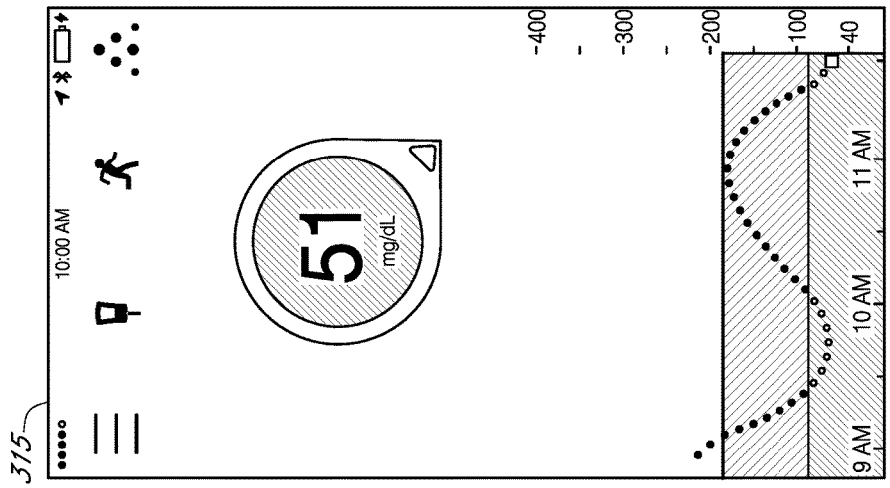
Figure 40:
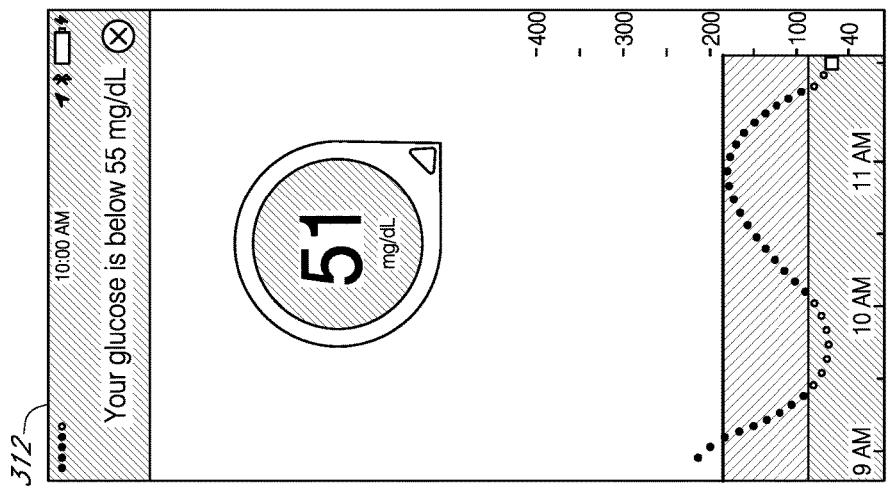

In another implementation, a smart alert may be provided on the lock screen of a smart phone. FIGS. 30-41 indicate such an implementation, both generally and within the context of a low glucose alert. As may be seen, when a user sees a notification on their smart phone (FIGS. 30, 34, and 38), they may unlock their phone and see a "pop over" notification of the alert (FIGS. 31, 35, and 39). An "okay"

button is shown, and upon activation, a trend screen may be displayed (FIGS. 32, 36, and 40). In these figures, a banner covers other navigation buttons within the application, the inability to access such navigation functions reaffirming the importance of the alert. The user can close the banner alert by tapping the X button and continue using the application. Alternatively, the banner will disappear once the user corrects their glucose to raise their glucose value to a satisfactory level. In alternative implementations, the alert banner may be relocated below the navigation pane, enabling the user to use the navigation functions even when the alert is displayed. Such may be configured to be based on the urgency of the alert.

In the displayed user interface implementations, or in any other implementations, tapping an appropriate icon displayed on the screen, e.g., a magnifying glass, may cause the display of additional information or could invoke other functionality. For example, tapping an appropriate icon could lead to various levels of prediction being displayed, e.g., indicating to the user what is expected over the next 10 or 15 minutes. Such prediction may be provided by textual indicators, a dotted line on a glucose trace graph, arrows, time- and glucose-indicating endpoints, and the like.

In another embodiment, smart alert functionality may be implemented such that an alert or alarm sound volume automatically adjusts to be appropriate given a detected ambient noise level. In other words, given a detected ambient noise level, the volume of the alert or alarm may be adjusted such that a signal-to-noise ratio is sufficient to allow a user to hear the alert or alarm. Such volume may also be user customizable. The detection of the ambient noise level may be implemented by including a microphone or other sensor to detect and measure the same. In a smart phone implementation, the phone microphone may be used. Put another way, the system measures or detects an ambient noise level, and automatically adjusts an alert or alarm sound volume to achieve a desired predetermined signal-to-noise ratio or alternatively SINR.

A default volume setting may be provided that is sufficiently greater than an assumed ambient noise level. When the measured noise level is louder than that assumed by the default, or the noise level detected or assumed during customization, the alert/alarm volume may be automatically increased, either on a gradual basis or suddenly, to levels such that the user can hear the alert or alarm. For example, the decibel level of the alert/alarm may be set to have a predetermined relationship with the ambient noise level, e.g., to achieve the predetermined signal-to-noise ratio noted above. The noise level in such implementations can be advantageously measured just prior to the issuance of an alert/alarm.

In other implementations of the outputs, where the user has experienced an unpleasant event, e.g., hypoglycemic, hyperglycemic, out-of-control glucose, or the like, systems and methods according to present principles may automatically generate a post-event smart alert indicating some degree of forensics, informing the user as to how the event occurred, and providing helpful tips to prevent future such events. Such automatic generation of forensic information may be particularly provided where the system, by virtue of determination or detection of a signal characteristic or other diagnostic information, is able to uniquely identify the cause of the unpleasant event. By providing such forensics, the user becomes informed that the smart alerts functionality is configured to track, detect, and is programmed to alert on such unpleasant events, increasing user confidence and trust in the system. In addition, data about such events may be advantageously employed to refine the operation of the smart alerts application/functionality through the use of machine learning algorithms.

The system may further be configured to indicate a caution or other modifier associated with a smart alert. For example, the system could provide an indication such as "I'm waiting an hour before I alarm because I'm waiting for [a known "on-board" therapeutic aspect, e.g., insulin or food or exercise] to kick in. But be aware that there may be an alert or alarm about this condition on the horizon." Such an indication provides a middle ground where the system may have some confidence in an estimation or prediction of user cognitive awareness, but the confidence is not unequivocal; equivalently, the level of estimation or prediction is not enough to unambiguously establish user cognitive awareness or user cognitive unawareness. In a particular implementation, such cautions or modifiers may be configured to appear along with the smart alert (via various string manipulation subroutines) whenever the estimation or prediction of cognitive awareness is within 5% of the threshold level. It will be understood that the content of the string modification will vary depending on the type and content of the smart alert.

Certain smart alerts functionality may be leveraged even during a sensor warm-up period. In more detail, when a new sensor is installed, a period of time generally exists when no information is available, e.g., two hours. During this time, the blood glucose values are not ensured to be accurate. However, trend values may still be obtained, and the display of these advantageous for a user. A finger stick blood glucose value may be employed during this warm-up period to obtain an accurate glucose value, and in some cases system analysis of the indication of the trend obtained during the warm-up period may be employed as a trigger to obtain such a finger stick value. In an implementation, if the glucose monitoring algorithm used the last known reading from the removed sensor, the algorithm may automatically cause an instruction or a user prompt indicating that the user should perform a finger stick as a safety caution. For example, if the last known glucose value from the removed sensor was 76 and had a downward trend, then reduced ion counts during warm-up may indicate that the user is trending towards a hypoglycemic event. As the actual glucose value data is unavailable during warm-up, the estimation or prediction of user cognitive awareness of the diabetic state warranting attention will be correspondingly lower. In this situation, a smart alert may be generated that the user should perform a finger stick. In another example, if the last known glucose value from the removed sensor was 76 and was relatively stable, but real-time reduced ion counts are being measured during warm-up, the same may again indicate that the user is not cognitively aware of a potential hypoglycemic situation, particularly as the user did not even have the benefit of an indication of a downward trend during the prior sensor session. In summary, the smart alerts functionality may employ prior sensor session data as well as real time trend information in the generation of smart alerts, where the generation is based on a level of user cognitive awareness, generally compared to a threshold criterion, which can itself depend on one or more data inputs.

In a further implementation, it is noted that CGM and low glucose alert thresholds assist users with identifying impending hypoglycemia so that the users can take action to avoid or minimize the hypoglycemic episode. Such features are particularly useful when patients have difficulty identifying low glucose based on physiological symptoms such as shakiness, sweating, and so on, and these correspond to users with impaired hypoglycemia awareness. Hypoglycemia awareness is variable from episode to episode, and has been shown to be impacted by recent hypoglycemic events. Notably, recent hypoglycemic events reduce a user's awareness of subsequent episodes.

Accordingly, in this further implementation of systems and methods according to present principles, an alert characteristic may be modified as a function of a recent history of hypoglycemic episodes, such that alerts are more likely to be provided earlier or be more salient in situations where the patient is least likely to become aware of their hypoglycemia as a result of their symptoms. Typical alert characteristics to be modified include, e.g., threshold, intensity, visual display, and so on. Such an implementation minimizes the number and/or annoyance of nuisance alerts (alerts provided when the patient is already aware of the hypoglycemia, or provided more frequently than desired) when alerts are less valuable and maximizes the sensitivity and/or saliency of alerts when patients cannot rely as much on symptoms. Put another way, user cognitive awareness may further be based on recent history of hypoglycemic episodes, as such have been shown to reduce user awareness of subsequent episodes. In an implementation, recent history of hypoglycemic episodes may be gleaned from past or historic data, and used in combination with real-time data, e.g., glucose data, glucose rate of change, and so on, particularly real-time data indicating potential hypoglycemia, to result in a data output useful in the estimation or prediction of user cognitive awareness. The data output useful in the estimation or prediction of user cognitive awareness may be used, e.g., to raise or lower the threshold at which a user is estimated or predicted to be cognitively aware. Where there is a recent history of hypoglycemic episodes, the threshold may be raised, thus leading to additional smart alerts. Where user data indicates that a frequency of hypoglycemic episodes is reduced, e.g., due to better diabetes management by the user, the threshold may conversely be raised, reducing the number of smart alerts.

In alternative implementations, user interface-displayed smart alerts may incorporate or have outputs that may take any form noted in US Patent Publication No. US-2015/0289821, entitled GLYCEMIC URGENCY ASSESSMENT AND ALERTS INTERFACE and owned by the assignee of the present application and herein incorporated by reference in its entirety.

Use with Pumps and Other Delivery Devices

Smart alerts may be beneficially employed in combination with data from infusion pumps and other such delivery devices. In part the use of smart alerts will be dictated by the use of the delivery device, whether in an open loop system, a closed loop system, or a semi-closed loop system.

In an open loop system, the smart alerts may be used as described above, providing alerts on, e.g., bolus information, where the user is estimated or predicted to be cognitively unaware of a diabetic state warranting attention. For example, in the case of a meal bolus, machine learning may be employed to determine a meal pattern of a user, and where a glucose trace is encountered after a meal that is not part of a typical meal pattern, a smart alert can be generated based on such data to suggest a bolus. Besides determining that a bolus should be infused, the machine learning and smart alert may further be employed to determine the timing, e.g., preferably not too late or too early. Such learning typically involves analysis of past data to learn at which point in time during a "meal episode" the bolus should be delivered. In this case, past data, meal episode data, is used in combination with real-time data, e.g., indicating that the user is about to eat a meal or is approaching a typical meal time (determinable by clock data or event data or the like). Similarly, machine learning may be employed to determine that the user often overboluses, e.g., or causes so-called "rebound" or "rage" boluses. Such may be particularly relevant where the smart alerts app or functionality receives data from a pump or pen. If the system can determine that the user has a trend or pattern toward such overbolusing, the trend or pattern information may be employed to provide a smart alert to caution the user against the same. More generally, the information may be used to inform smart alerts functionality generally. Such may be particularly important during times in which a user is trending upward, e.g., towards hyperglycemia, as such times are particularly susceptible to overbolusing.

As another example of the use of smart alerts in the context of delivery devices, when a user changes an infusion set, there is a higher than usual risk of getting an infusion site or cannula that does not have proper insulin absorption or which is occluded. While occlusion alarms exist, the same are generally not useful at detecting problems with the infusion site, particularly if the cannula is not fully occluded. The standard of care dictates that users check their blood glucose levels two hours after changing their infusion sets to ensure that they are getting proper insulin delivery. Undetected cannula problems can lead to hyperglycemia and even ketoacidosis, which can be life-threatening, and constitutes the main risk of using pump therapy versus multiple daily injections.

Systems and methods according to present principles can detect problems with the infusion set early on, before the patient develops ketones, and can employ smart alerts to provide an alert about such a diabetic state warranting attention to a user, who in such situations is generally completely cognitively unaware of the existence of the problem. For example, knowing when a patient changed their infusion set can be used in the determination of a probability of a bad infusion site, and such data can further be employed to distinguish between other rises in blood sugar and infusion set problems. In particular, the system can employ data about cannula fills, reservoir changes, and pump primes to determine instances when a user has changed all or a portion of their infusion set, and such data can be used in combination with CGM data as part of the estimation or prediction of user cognitive awareness; fluid pressure data is useful in learning individualized alarms for possible infusion set problems, and can be similarly used. While CGM data and pump data used separately are generally insufficient at detecting infusion set problems, together they provide more specific alarms that can prevent dangerous events, particularly hyperglycemic events. Such in particular can be used to determine and alert on infusion set problems, alerting the user to address the problem before the onset of medical issues, including ketoacidosis.

Figure 42:
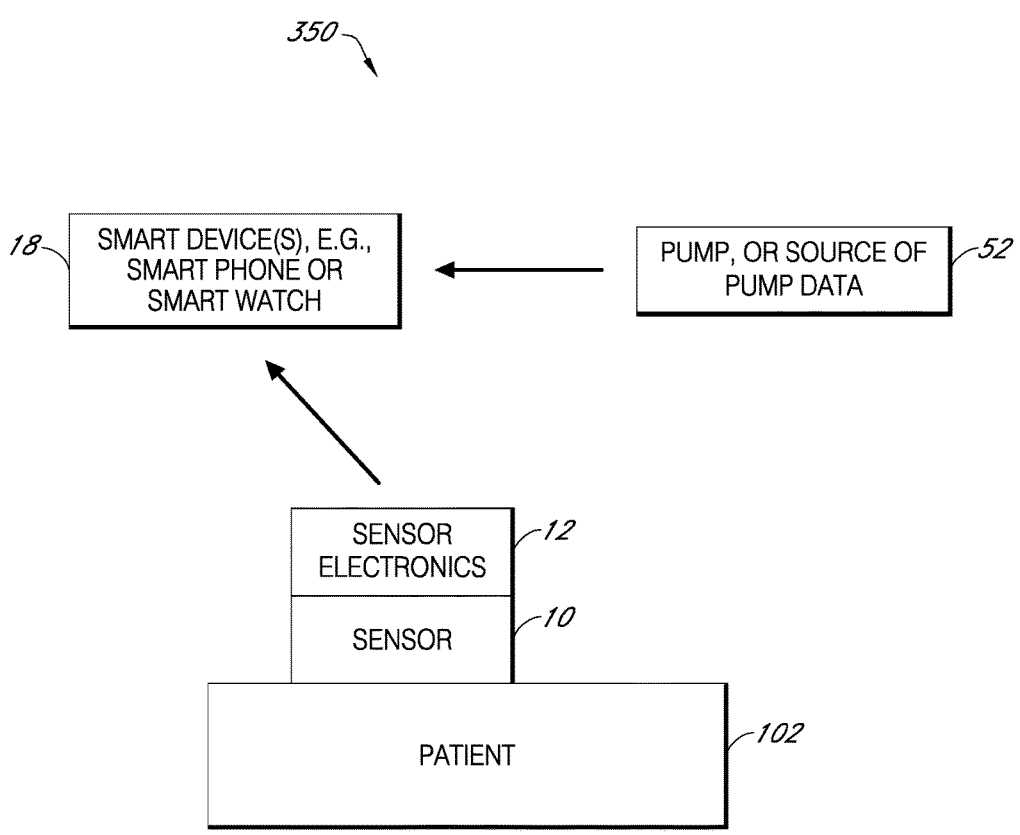
FIG. 42 is a schematic illustration of a system according to present principles incorporating data from a delivery device.
Figure 43:
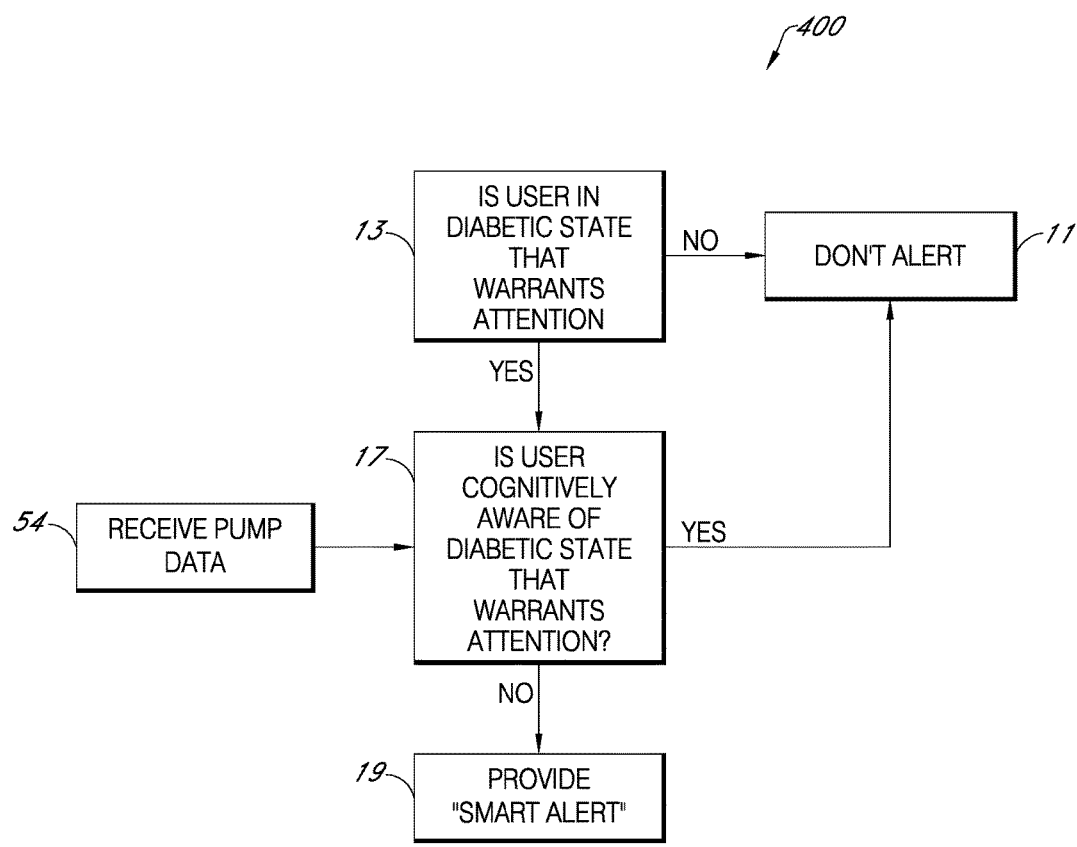
FIG. 43 is a flowchart of a fourth method according to present principles.

In particular, and referring to the system 350 of FIG. 42, the system of FIG. 1 is illustrated as also receiving data from a pump 52 (or a source of pump data). By analysis of pump data, e.g., by comparing received pump data to patterns or signatures of known pump data, particularly associated with issues preventing proper operation of the pump, the CGM app can detect cannula/infusion set problems and provide smart alerts thereabout. Such problems are particularly and notoriously difficult for users to detect, and thus may weigh heavily in prediction or estimation of user cognitive awareness of the diabetic state warranting attention. Thus, and referring to the flowchart 400 of FIG. 43 (based on the flowchart 101 of FIG. 2), the method of providing smart alerts may include a step of receiving pump data (step 54), and the same may be employed in the calculation of the estimation or prediction of user cognitive awareness.

Pump data received in step 54 may include data relating to the bolus information, pump shutoff data, pump alarms, pump rewind (time), pump prime (time), cannula fill (timing and amount), fluid pressure or other data employed to generate occlusion alerts, and so on. In one implementation, APIs allowing access to such data may be employed in monitoring applications. Conversely, smart alerts functionality may also be provided within the context of an application operating and controlling a delivery device, and in this case data from a CGM app or other monitoring app may be employed via an appropriate API to the smart alerts functionality running on the delivery device.

Thus, where users are not cognitively aware of pump problems such as occlusions, smart alerts may be provided to inform them of the diabetic state warranting attention, and thus provide an alert that is more effective to a user than prior alerts.

In other implementations of smart alerts in the context of pumps/pens or other delivery devices, the user interface of such delivery devices may be employed to acknowledge smart alerts, and conversely the user interface of a monitoring device may be employed to acknowledge alerts initiated by the delivery device. Put another way, data about a smart alert generated by one device may be communicated to another device using an appropriate transmission protocol, and rendered and in some cases acknowledged on the other device. If acknowledged, the acknowledgment may be communicated back to the generating device using an appropriate transmission protocol.

Figure 44:
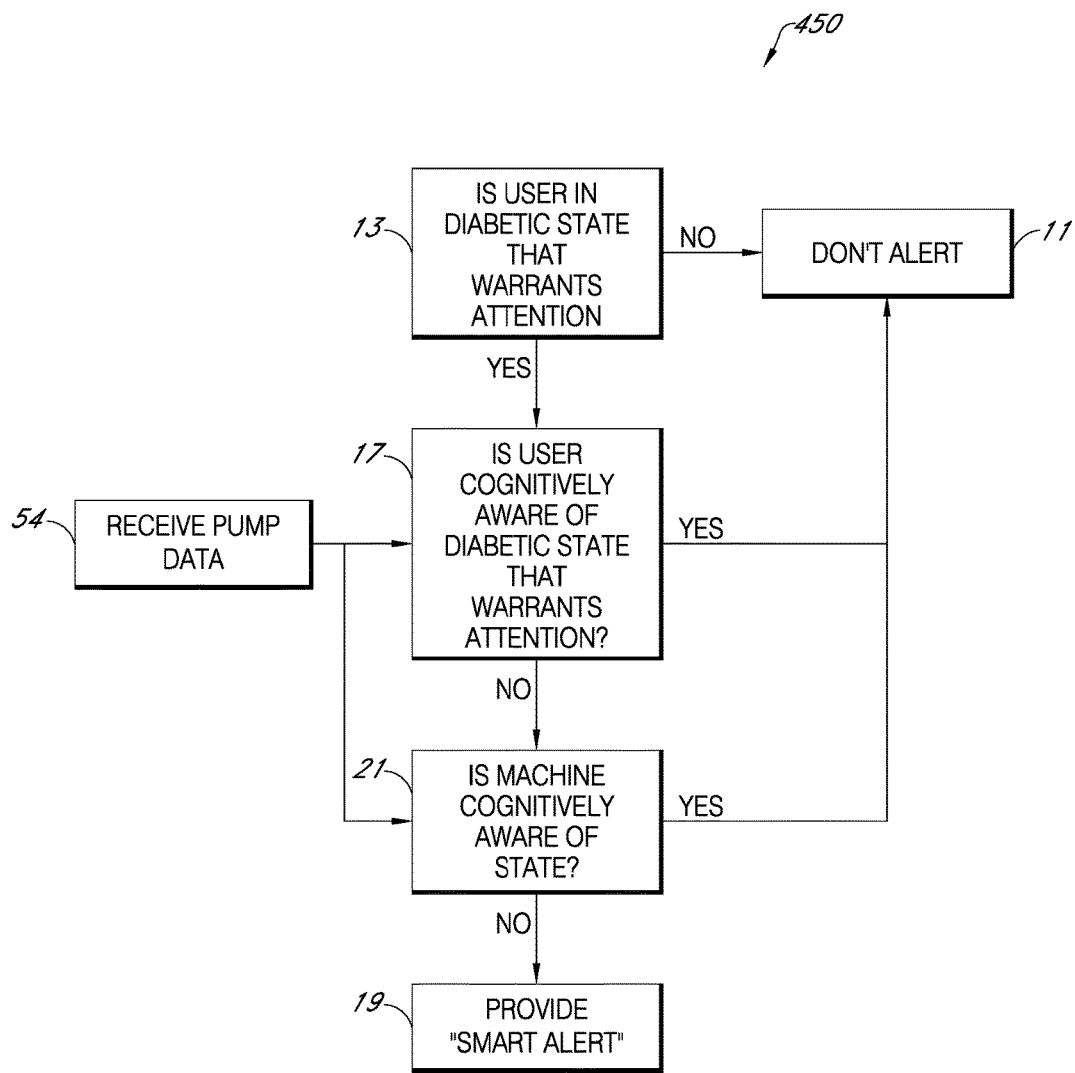
FIG. 44 is a flowchart of a fifth method according to present principles.

Smart alert functionality as implemented in an open loop system may provide smart alerts prompting the user to take various actions, based on user cognitive awareness. In a closed loop system or a semi closed loop system, considerations may be had of both user cognitive awareness and machine cognitive awareness, where the latter relates to machine awareness of a diabetic state warranting attention. This implementation is illustrated by the flowchart 450 of FIG. 44. In the flowchart 450, which is also based on the flowchart 101 of FIG. 2, following a step of determining user cognitive awareness (step 17), a step may be employed of determining if the system is cognitively aware of the diabetic state warranting attention (step 21). If the machine is cognitively aware of the state, then again there is no need for a smart alert, and the same can be suppressed or never generated (step 11). If the machine is not cognitively aware of the state, then a smart alert can be provided (step 19). It is noted that the estimation or prediction of user cognitive awareness is itself a task performed by the machine, but this is distinct from the machine cognitive awareness of step 19 because the latter relates to whether a delivery device is connected and is treating the diabetic state or preparing to treat the same. For example, machine cognitive awareness may cause a shut off of a pump if the system determines, e.g., based on glucose value and rate of change, that the user may become hypoglycemic. Such is distinct from a determination of step 17 that a user is aware of an impending hypoglycemic potentiality and is taking steps to treat the same, e.g., is part of a typical pattern that the user treats by consuming carbohydrates.

As an extra step is provided before a smart alert is generated, smart alerts may be generated less frequently in a closed loop system than in an open loop system or in a semi closed loop system, and generally only where the system itself cannot treat the diabetic state warranting attention.

A particular implementation is described in the context of a user approaching a hypoglycemic situation. Instead of just using a threshold, where an insulin pump would be automatically shut off upon the crossing of a low glucose threshold, if the result of the estimation or prediction of user cognitive awareness performed by the smart alerts functionality is such that the user is estimated or predicted to be cognitively aware of the diabetic state warranting attention, then the pump may be caused to shut off sooner than in the case where the user is not cognitively aware, in order to avoid situations of dangerous hypoglycemia. A typical situation in which the user would be unaware would be nighttime, when the user is sleeping.

What has been described are systems and methods for providing smart alerts to users, such that users may be alerted to diabetic states warranting attention in a more effective way than in prior efforts.

Variations will be understood. For example, systems and methods could interface with other applications and employ the same for provision of alerts. For example, where a user is estimated or predicted by the system to be cognitively unaware of an impending hypoglycemic diabetic state warranting attention, but data from a GPS app on the user smart device indicates proximity to a source of food, e.g., a gas station or food store, an alert may appear on the GPS app about the impending condition and the location at which remedial action may be taken. Generally the data from the GPS app will be that which provides information about the location of the source of food, but data from other apps may also be leveraged, e.g., meal tracking apps, which may also provide information about restaurant locations. Such an alert generally uses an appropriate API between the GPS app and the CGM app and APIs between other employed apps. In some cases, data from the GPS app will indicate that the user is traveling in a direction towards a commonly accessed food source, e.g., a restaurant the user frequents. Especially of the determination can be made unequivocally, e.g., there are no other commonly frequented locations in that direction, then such GPS data may be employed to suppress the generation of a smart alert in the event of potential mild hypoglycemia, at least temporarily. Generally speaking, GPS data used in this way can be advantageously employed in the estimation or prediction of user cognitive awareness. Implementations of Systems and Methods According to Present Principles Enabling Smart Alerts/Functionality.

Various systems may be employed to implement smart alert functionality according to present principles. For example, in one implementation, a mobile computer device, e.g., smart device, e.g., smart phone, may be employed that is dedicated to health and diabetes management. The mobile computer device may be one that is dedicated to health/diabetes management or may be a more general device that is specially adapted for health and diabetes management. The device may be configurable by the user to suit the user's lifestyle and preferences. The mobile device may be based on an Android or iOS (or other) operating system and utilize a touchscreen interface. In some cases the operating system may be customized or controlled for administrative services, e.g., to provide data to the cloud, and to optimize/control elements of the user experience. The device may include one or more common radio communication links, such as Bluetooth® Low Energy. It may also include WiFi or other data connectivity technology, for remote monitoring, data transfer, and software updates.

The mobile computer may be used in conjunction with ("tethered" to) a wearable computing device such as a Smart Watch. The Watch may also function usefully without direct connection (untethered) to the mobile device. Such a watch or other such wearable may include sensors such as heart rate monitors, and data from such monitors may also be employed to inform smart alerts functionality. For example, such monitors may be employed to determine if a user is exercising (perhaps in combination with accelerometer data), and if so, the user may desire more or less alerts/alarms.

Such wearable devices may also allow the possibility of configuring smart alerts functionality to render a tactile display, providing significant privacy and discretion in social situations, and usefulness in, e.g., sleep. The smart alerts functionality may be configured to, if a wearable with a tactile display is detected, first provide the alert on the wearable, followed by alerting on other devices, e.g., smart phones, if the alert or alarm on the wearable is ignored.

The user may select from a curated ecosystem of Apps. This selection may include Apps from, for example, Databetes (meal memory), TrainingPeaks (activity/fitness), Tidepool, MyFitnessPal, Nike+, Withings, etc. Other apps may be included for retrospective insight/pattern recognition aimed at therapy optimization and for the determination of user cognitive awareness of their current diabetic state warranting attention. The ecosystem may further include an app that provides basic diabetes management instructions for the newly-diagnosed user (or parent of user) with T1D. A distinct set of instructions may be included for the newly-diagnosed user with T2D.

The mobile computer allows connectivity of data between user (patient) and clinician, via EMR (e.g. Epic). The mobile computer platform enables and facilitates user/provider dialogue.

In another particular implementation, the mobile computer may be configured such that it does not include functionality unrelated to health management.

Safety settings are generally implemented. For example, the smart alerts functionality may be disabled until such time as CGM data has been collected. In this way, the settings may be data-driven and data validated. For example, one week of data may be required, two weeks of data may be required, one month of data may be required, and so on. As noted above, an initial set up or training may be performed without data, or using data from a prior user device (associated with the subject user). This may be followed up with a subsequent optimization, and in particular the smart alerts functionality may perform a data analysis subroutine or diagnostic subroutine to determine that enough data has been collected to allow functionality related to smart alerts, e.g., to allow prediction or estimation of user cognitive awareness, or may alert the user or the HCP to perform the same. Alternatively, the smart alerts functionality may be automatically implemented, but require confirmation from the user or HCP.

As noted previously, users are often annoyed by receiving multiple alert or alarm notifications, and the smart alerts functionality according to present principles may serve to minimize such annoyances. However, where multiple notifications are called for and provided, smart alerts functionality may also be configured to allow subsequent notifications to include additional information, so that the user receives an aggregate of all of the actual or potential alerts. For example, if a first notification provides an indication that the user may be going low, and then the system, via smart alerts functionality, knows to not alert the user again, or to suppress alerts/alarms, until another alert threshold is reached, then the subsequent notification may include a different substantive message, e.g., "you've been low for 20 minutes now".

Systems and methods according to present principles may further be employed to detect missed windows for opportunities or actions. In particular, machine learning may be employed to learn when a user typically takes an action, particularly one that has a positive outcome. Where a similar situation is encountered, but a user does not act in the positive way, e.g., they are away from their smart device or such and are not aware of the opportunity, a smart alert may subsequently provided regarding the missed opportunity.

What has been described are systems and methods for achieving smart alerts, especially where based on estimated or projected user cognitive awareness of the diabetic state warranting attention. Numerous variations of the above will be understood given this description.

Sensor System

Figure 45:
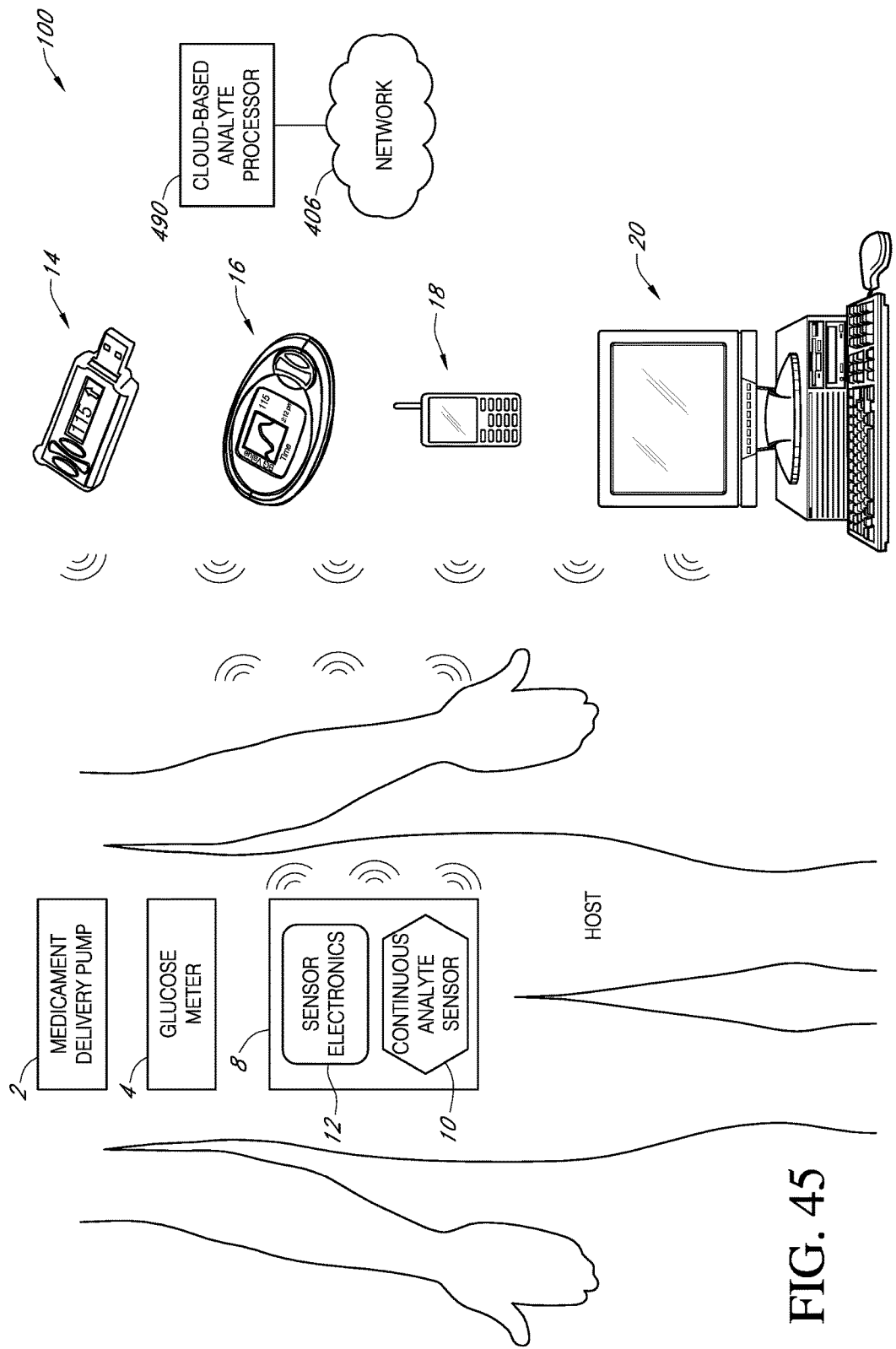
FIG. 45 is a schematic illustration of a system according to present principles.

FIG. 45 depicts an example system 100, in accordance with some example implementations. The system 100 includes a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient-related data) provided via network 406 (e.g., via wired, wireless, or a combination thereof) from sensor system 8 and other devices, such as display devices 14-20 and the like, associated with the host (also referred to as a user or patient) and generate reports providing high-level information, such as statistics, regarding the measured analyte over a certain time frame. A full discussion of using a cloud-based analyte processing system may be found in U.S. patent application Ser. No. 13/788,375, filed 7 Mar. 2013 and published as US-2013/0325352, entitled CALCULATION ENGINE BASED ON HISTOGRAMS, herein incorporated by reference in its entirety. In some implementations, one or more steps of the factory calibration algorithm can be performed in the cloud.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof, to provide measurement of levels of the analyte via a continuous analyte sensor, such as a continuous glucose sensor. An example implementation of the sensor electronics 12 is described further below with respect to FIG. 46.

In one implementation, the factory calibration algorithms described herein may be performed by the sensor electronics.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., smart alerts, medicament delivery information, discrete self-monitoring glucose readings, heart rate monitor, caloric intake monitor, and the like). In some cases, the display device may be, e.g., a user's car, if the car is in signal communication with, e.g., the user's smart phone. For example, the car may be in Bluetooth communication or have a Bluetooth pairing with the smart phone. Other display devices may include televisions, smart refrigerators, and so on.

In one implementation, factory calibration algorithms may be performed at least in part by the display devices.

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information including smart alerts, such as a numerical value, and an arrow, or a color code.

In some example implementations, the relatively large, hand-held display device 16 may comprise a hand-held receiver device, a palm-top computer, and/or the like. This large display device may include a relatively larger display (e.g., larger than the small display device 14) and may be configured to display information including smart alerts, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some example implementations, smart alerts may be provided to alert the user when they are running low on diabetic supplies, and then to automatically reorder or to prompt the user to reorder. For example, in some situations, the system may learn that the user typically orders two days ahead of time, and the system may be aware of the fact that the sensor has two days' worth of life remaining. In this case, the system may provide a smart alert informing the user that it is time to order new supplies.

Where user acknowledgments are employed, the same may be acknowledged on receivers, mobile devices, or other such devices. In some cases, alerts or alarms may be acknowledged on the transmitter directly. In some cases, fingerprint recognition may be employed in the acknowledgments, so that non-users do not deleteriously acknowledge alerts or alarms of a user, thereby potentially causing the user to not receive such an alert or alarm.

Although the disclosure herein refers to some implementations that include a continuous analyte sensor 10 comprising a glucose sensor, the continuous analyte sensor 10 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 46:
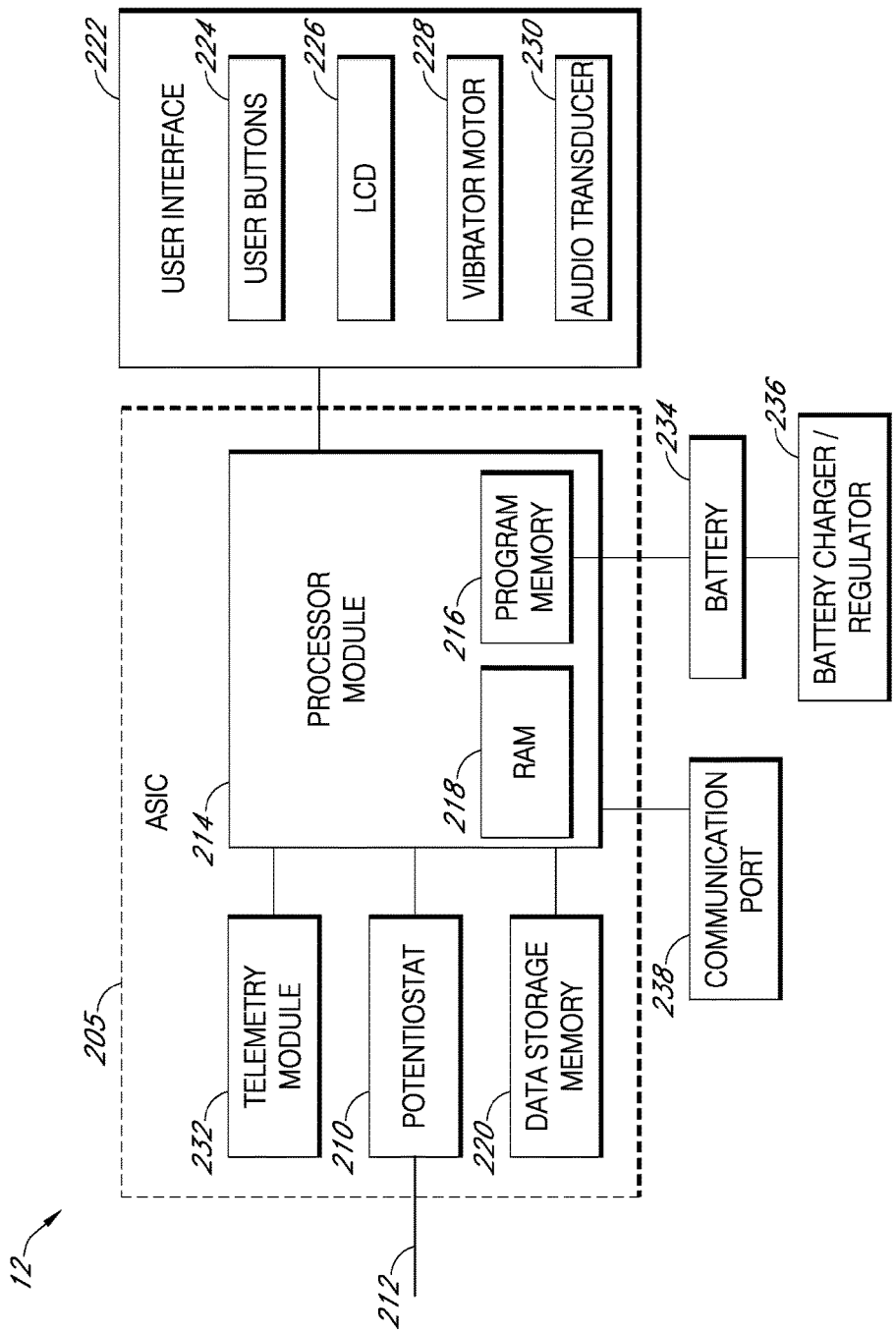
FIG. 46 is a more detailed schematic illustration of a sensor electronics module.

FIG. 46 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by calibration algorithms, smoothing and/or filtering algorithms of sensor data, and/or the like.

In some embodiments, a processor module 214 is configured to achieve a substantial portion, if not all, of the data processing, including data processing pertaining to factory calibration. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronics 12 or other associated devices (e.g., 14, 16, 18, 20 and/or 490). For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a calibration.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such as devices 14, 16, 18, and/or 20, and/or other components for signal processing and data storage (e.g., processor module 214 and data storage memory 220). Although FIG. 46 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 46, through a first input port 211 for sensor data the potentiostat 210 is coupled to a continuous analyte sensor 10, such as a glucose sensor, to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth®, Bluetooth® Low-Energy, ANT, ANT+, ZigBee, IEEE 802.11, IEEE 802.16, cellular radio access technologies, radio frequency (RF), inductance (e.g., magnetic), near field communication (NFC), infrared (IR), paging network communication, magnetic induction, satellite data communication, spread spectrum communication, frequency hopping communication, near field communications, and/or the like. In some example implementations, the telemetry module 232 comprises a Bluetooth® chip, although Bluetooth® technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like). In some cases, an audible alert may be silenced while a visual alert is still rendered. As a particular example, an audible alarm may be silenced while the user may still be enabled to view a glucose trace and/or a threshold line. In this way, the user is informed that they are still high or low, while avoiding the annoyance of the audible alert.

Although audio and vibratory alarms are described with respect to FIG. 46, other alarming mechanisms may be used as well. For example, in some example implementations, a tactile alarm is provided including a poking mechanism configured to "poke" or physically contact the patient in response to one or more alarm conditions.

In one exemplary implementation, a default method of alerting may be employed, e.g., a display on a screen, but if alerts or alarms using the default mode are not acknowledged within a predetermined period of time, the alerts and alarms may escalate in subsequent reminder alerts or alarms, and many employ alternate means of notification, including using connected devices such as medicament delivery devices. For example, if original or initial alerts and alarms are not acknowledged, on the next subsequent or reminder alert or alarm, which may occur, e.g., five minutes later, the mobile device and/or connected medicament device may provide a supplementary or ancillary alert, e.g., an audible alert, e.g., the cell phone may emit a sound. If this alert or alarm is also not acknowledged, and if a pump or pen is connected to the mobile device (for example, in referring to FIG. 45, if the medicament delivery pump 2 is connected to a device performing responsive processing, e.g., mobile device 18 or processor 490, or even in some cases sensor electronics 12), the medicament delivery device (pump or pen) may be caused to emit an audible or tactile or visual alert or alarm, e.g., having a medium amplitude, e.g., medium volume, for a predetermined period of time, e.g., for 20 seconds. Similarly, if these alerts or alarms are also not acknowledged, and again if the pump or pen is connected to the device performing responsive processing, the same may be caused to emit an audible or tactile or visual alert or alarm, e.g., having a high amplitude, e.g., high volume, for a predetermined period of time, e.g., for 20 seconds.

Other means may also be employed for rendering alerts or alarms. For example, dogs are increasingly being used as diabetic alert dogs or as companion animals. In either case, a component of the system may be configured with an ultrasound transmitter such that, if the glucose concentration value of a user is approaching a dangerous value, the ultrasound transducer is caused to render an ultrasonic pulse. The diabetic alert dog will generally detect an imminent hypoglycemia or hyperglycemia situation; however, if they did not, the ultrasonic pulse may provide a reminder. Similarly, a companion animal not trained as a diabetic alert dog may be trained to recognize the pulse as a reason to alert their owner, i.e., the diabetic user. Even if such dogs are not specifically trained, the ultrasonic pulse may cause a level of agitation that provides a warning to the user that something is wrong. The ultrasound transmitter may be signally coupled to various parts of the system, e.g., the transmitter, the smart phone, a receiver, or other device. As the severity of the danger increases, the ultrasonic tone could change, so the diabetic companion could be trained to respond accordingly.

In another example, users may be informed of their glucose alerts, alarms, and notifications, without even looking at their monitoring device by use of distinctive haptic or vibratory patterns as may be rendered on a smart device or watch. Haptic/vibratory patterns may be rendered and structured according to relative urgency or safety concerns using similar principles of the prioritization of auditory or visual alarms and alerts. For example, higher priority alarms may employ a higher vibration speed, a lesser space between vibrations, a greater duration, and vice versa for lower priority alarms. Users may be enabled to conform particular vibratory profiles or curves according to their own dictates and designs. In this way, users can be informed of alerts or alarms and may even receive information about the type and/or urgency of alarms, without having to look at a display screen or listen to an alarm (which latter may also be annoying as it may disturb others in the user's vicinity).

The battery 234 may be operatively connected to the processor module 214 (and possibly other components of the sensor electronics 12) and provide the necessary power for the sensor electronics 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device for retrospective analysis by a patient and/or HCP. As another example of data transmission, factory information may also be sent to the algorithm from the sensor or from a cloud data source.

The one or more communication ports 238 may further include a second input port 237 in which calibration data may be received, and an output port 239 which may be employed to transmit calibrated data, or data to be calibrated, to a receiver or mobile device. FIG. 46 illustrates these aspects schematically. It will be understood that the ports may be separated physically, but in alternative implementations a single communication port may provide the functions of both the second input port and the output port.

Exemplary Embodiments

Non-transitory computer readable medium 1: A non-transitory computer readable medium, comprising instructions for causing a computing environment to perform a method of dynamically adjusting or tuning user alerts based on a cognitive awareness determination, thereby providing data relevant to treatment of a diabetic state warranting attention, the method comprising steps of: identifying a current or future diabetic state warranting attention, the identifying based at least partially on a glucose concentration value; estimating or predicting a cognitive awareness of the user of the identified current or future diabetic state warranting attention; and if the result of the estimating or predicting is that the user is cognitively unaware of the identified current or future diabetic state warranting attention, then alerting a user with a user prompt on a user interface of a monitoring device, the user prompt indicating the diabetic state warranting attention, whereby the user is only alerted of the diabetic state warranting attention if and at a time that the user is unaware of the diabetic state warranting attention and that the notification is effective for the user.

Non-transitory computer readable medium 2: An embodiment of non-transitory computer readable medium 1, wherein the alerting is optimized for cognitive awareness of the patient such that fewer alarms occur than would otherwise be provided without consideration of user cognitive awareness.

Non-transitory computer readable medium 3: An embodiment of any of non-transitory computer readable media 1-2, wherein the monitoring device is a smart phone, a smart watch, a dedicated monitoring device, or a tablet computer.

Non-transitory computer readable medium 4: An embodiment of any of non-transitory computer readable media 1-3, whereby over-prompting, repeat prompts, or nuisance prompts are minimized or avoided.

Non-transitory computer readable medium 5: An embodiment of any of non-transitory computer readable media 1-4, whereby the user is enabled to build trust in the system, that the system will only alert on notifications optimized or effective for the user.

Non-transitory computer readable medium 6: An embodiment of any of non-transitory computer readable media 1-5, wherein the estimating or predicting a cognitive awareness of the user includes determining if the identified current or future diabetic state warranting attention includes an atypical glucose trace.

Non-transitory computer readable medium 7: An embodiment of non-transitory computer readable medium 6, wherein the atypical glucose trace includes an atypical pattern or an atypical glucose response.

Non-transitory computer readable medium 8: An embodiment of any of non-transitory computer readable media 1-7, wherein the estimating or predicting a cognitive awareness of the user includes determining if the user has previously treated a like identified diabetic state warranting attention by taking an action without a user prompt.

Non-transitory computer readable medium 9: An embodiment of non-transitory computer readable medium 8, wherein the action is dosing of a medicament.

Non-transitory computer readable medium 10: An embodiment of non-transitory computer readable medium 8, wherein the action is eating a meal.

Non-transitory computer readable medium 11: An embodiment of non-transitory computer readable medium 8, wherein the action is exercising.

Non-transitory computer readable medium 12: An embodiment of any of non-transitory computer readable media 1-11, wherein the estimating or predicting a cognitive awareness of the user includes determining if the user has entered meal or bolus data, or has requested a bolus calculation.

Non-transitory computer readable medium 13: An embodiment of any of non-transitory computer readable media 1-12, wherein the estimating or predicting a cognitive awareness of the user includes determining if user behavior is consistent with cognitive awareness.

Non-transitory computer readable medium 14: An embodiment of any of non-transitory computer readable media 1-13, wherein the estimating or predicting a cognitive awareness of the user includes receiving user input and basing the estimating or predicting at least in part on the received input.

T Non-transitory computer readable medium 15: An embodiment of any of non-transitory computer readable media 1-14, wherein the estimating or predicting a cognitive awareness of the user includes analyzing historic data of glucose values of the user versus time.

Non-transitory computer readable medium 16: An embodiment of any of non-transitory computer readable media 1-15, wherein the steps of identifying and estimating or predicting are repeated until such a time as the user is estimated or predicted to be cognitively unaware of the identified diabetic state warranting attention, and then performing a step of alerting the user with the user prompt.

Non-transitory computer readable medium 17: An embodiment of any of non-transitory computer readable media 1-16, wherein the estimating or predicting a cognitive awareness of the user includes receiving data from an application or website through an appropriate API.

Non-transitory computer readable medium 18: An embodiment of any of non-transitory computer readable media 1-17, wherein the estimating or predicting is based at least partially on location data, namely GPS data.

Non-transitory computer readable medium 19: An embodiment of non-transitory computer readable medium 18, wherein the location data is that of the user.

Non-transitory computer readable medium 20: An embodiment of non-transitory computer readable medium 18, wherein the location data is that of a follower of the user.

Non-transitory computer readable medium 21: An embodiment of any of non-transitory computer readable media 1-20, wherein the estimating or predicting a cognitive awareness of the user is based at least partially on one or more of the following: population data, data associated with behavioral or contextual information, data associated with a life goal of the user, data associated with a user privacy setting, or a combination of these.

Non-transitory computer readable medium 22: An embodiment of any of non-transitory computer readable media 1-21, wherein the estimating or predicting a cognitive awareness of the user is based at least partially on real-time data, and wherein the real-time data includes one or more of the following: data associated with a GPS application in the monitoring device, data associated with an accelerometer in the monitoring device, data associated with behavioral or contextual information, data associated with a location of a follower of the user, data associated with a metabolic rate of the user, data associated with a glycemic urgency index of the user, heart rate data, sweat content data, data associated with a wearable sensor of the user, insulin data, or a combination of these.

Non-transitory computer readable medium 23: An embodiment of any of non-transitory computer readable media 1-22, wherein the estimating or predicting a cognitive awareness of the user includes recognizing one or more individualized patterns associated with the user.

Non-transitory computer readable medium 24: An embodiment of non-transitory computer readable medium 23, wherein the individualized pattern corresponds to an envelope of characteristic analyte concentration signal traces occurring before or after an event.

Non-transitory computer readable medium 25: An embodiment of non-transitory computer readable medium 24, wherein the event is associated with a meal, exercise, or sleep.

Non-transitory computer readable medium 26: An embodiment of non-transitory computer readable medium 25, wherein the determination is that the user is cognitively unaware if a current signal trace falls outside the envelope of characteristic analyte concentration signal traces.

Non-transitory computer readable medium 27: An embodiment of any of non-transitory computer readable media 1-26, wherein the method further comprises indicating a confidence level associated with the user prompt.

Non-transitory computer readable medium 28: An embodiment of any of non-transitory computer readable media 1-27, wherein if the result of the estimating or predicting is that the user is not cognitively aware of the diabetic state warranting attention, then displaying the user prompt immediately.

Non-transitory computer readable medium 29: An embodiment of any of non-transitory computer readable media 1-28, wherein the estimating or predicting is further based on location information of the user, wherein the location information indicates that the user is within a predetermined threshold proximity of a food store or restaurant.

Non-transitory computer readable medium 30: An embodiment of any of non-transitory computer readable media 1-29, wherein if the result of the estimating or predicting is that the user is not cognitively aware of the diabetic state that warrants attention, then alerting the user with the user prompt after a time delay, a duration of the time delay based on at least the identified diabetic state warranting attention and the glucose concentration value and/or a glucose concentration value rate of change.

Non-transitory computer readable medium 31: An embodiment of any of non-transitory computer readable media 1-30, wherein the user prompt includes a query for a user to enter data.

Non-transitory computer readable medium 32: An embodiment of non-transitory computer readable medium 31, wherein the query requests data for the user to enter about dosing, meals or exercise.

Non-transitory computer readable medium 33: An embodiment of any of non-transitory computer readable media 1-32, wherein if the user ignores the user prompt as determined by data from the user interface or data from an accelerometer associated with the monitoring device, and if the user prompt does not correspond to a danger condition, then storing information about the user ignoring the user prompt under prior conditions and using the stored information as part of a subsequent estimating or predicting step.

Non-transitory computer readable medium 34: An embodiment of any of non-transitory computer readable media 1-33, wherein the identifying a current or future diabetic state warranting attention includes determining a clinical value of a glucose concentration and/or a glucose rate of change and/or a glycemic urgency index value.

Non-transitory computer readable medium 35: An embodiment of any of non-transitory computer readable media 1-34, wherein identifying a current or future diabetic state warranting attention includes measuring a glucose signal signature and comparing the measured signature with a plurality of binned signatures, and classifying the diabetic state warranting attention into one of a plurality of bins based on the comparison.

Non-transitory computer readable medium 36: An embodiment of any of non-transitory computer readable media 1-35, wherein the identifying a current or future diabetic state warranting attention determining one or more time-based trends in the glucose concentration value, and basing the identified state on the determined trend.

Non-transitory computer readable medium 37: An embodiment of non-transitory computer readable medium 36, wherein the trend correspond to whether the glucose concentration value is hovering within a range or is rising or falling, wherein hovering constitutes staying within a predetermined range for a period of greater than 5 or 10 or 15 or 30 minutes.

Non-transitory computer readable medium 38: An embodiment of non-transitory computer readable medium 37, wherein fuzzy boundaries are employed for defining the range.

Non-transitory computer readable medium 39: An embodiment of any of non-transitory computer readable media 1-28, further comprising transmitting an indication of the diabetic state warranting attention to a medicament pump.

Non-transitory computer readable medium 40: An embodiment of non-transitory computer readable medium 39, wherein if the result of the estimating or predicting is that the user is not cognitively aware of the diabetic state warranting attention, then further comprising activating the medicament pump to provide a medicament bolus.

Non-transitory computer readable medium 41: An embodiment of non-transitory computer readable medium 40, wherein the medicament bolus is a meal bolus of insulin.

Non-transitory computer readable medium 42: An embodiment of non-transitory computer readable medium 42, if the result of the estimating or predicting is that the user is not cognitively aware of the diabetic state warranting attention, then further comprising activating the medicament pump to change a basal rate.

Non-transitory computer readable medium 43: An embodiment of non-transitory computer readable medium 40, wherein the medicament is insulin.

Non-transitory computer readable medium 44: An embodiment of non-transitory computer readable medium 39, further comprising determining if the medicament pump can treat the diabetic state warranting attention either fully or partially, and if so, then not alerting the user or altering the user prompt, respectively, as compared to a case where the medicament pump cannot treat the diabetic state.

Non-transitory computer readable medium 45: An embodiment of any of non-transitory computer readable media 1-44, wherein, if the result of the estimating or predicting is that the user is not cognitively aware of the diabetic state warranting attention, then determining when to alert the user with the user prompt.

Non-transitory computer readable medium 46: An embodiment of any of non-transitory computer readable media 1-45, wherein the user prompt, if displayed, includes a color or arrow instead of or in addition to a glucose concentration value.

Non-transitory computer readable medium 47: An embodiment of any of non-transitory computer readable media 1-46, wherein the user prompt, if displayed, includes a prediction of a glucose concentration value.

Non-transitory computer readable medium 48: An embodiment of any of non-transitory computer readable media 1-47, wherein the user prompt, if displayed, includes an audible indicator, and wherein the volume of the audible indicator is automatically adjusted for ambient noise as measured by the monitoring device or by a device in signal communication with the monitoring device, wherein the adjusting for ambient noise includes raising the volume of the audible indicator relative to the ambient noise until a threshold level of signal to noise ratio is achieved.

Non-transitory computer readable medium 49: An embodiment of any of non-transitory computer readable media 1-48, wherein the user prompt is related to a diabetic state warranting attention occurring during a period when the user has a glycemic urgency index that is low.

Non-transitory computer readable medium 50: An embodiment of any of non-transitory computer readable media 1-49, wherein if the result of the estimating or predicting is that the user is not cognitively aware of the diabetic state warranting attention, then alerting the user with the user prompt after a delay based not on a time duration but on the identified diabetic state warranting attention and on the glucose concentration value and/or a glucose concentration value rate of change.

Non-transitory computer readable medium 51: An embodiment of any of non-transitory computer readable media 1-50, wherein if the result of the estimating or predicting is that the user is not cognitively aware of the diabetic state warranting attention, then alerting the user with the user prompt after a delay based not on a time duration but on an individualized pattern learned by the monitoring device.

Non-transitory computer readable medium 52: An embodiment of any of non-transitory computer readable media 1-51, wherein the identified diabetic state warranting attention corresponds to an atypical glucose response or an atypical pattern, and wherein the atypical response or atypical pattern is learned by a monitoring device and not by user entry.

Non-transitory computer readable medium 53: An embodiment of any of non-transitory computer readable media 1-52, wherein the user prompt is displayed with dynamic timing on a predesigned user interface and not on an adaptive user interface.

Non-transitory computer readable medium 54: An embodiment of any of non-transitory computer readable media 1-53, wherein if the result of the estimating or predicting is that the user is not cognitively aware of the diabetic state warranting attention, then alerting the user with the user prompt immediately regardless of indications to not alert the user with a user prompt received from other monitoring device applications.

Non-transitory computer readable medium 55: An embodiment of any of non-transitory computer readable media 1-54, wherein if the result of the estimating or predicting is that the user is not cognitively aware of the diabetic state warranting attention, then alerting the user with the user prompt immediately regardless of indications to not alert the user with a user prompt based on other user-entered data or settings.

Non-transitory computer readable medium 56: An embodiment of any of non-transitory computer readable media 1-55, wherein the estimating or predicting if the user is cognitively aware of the diabetic state warranting attention is based at least in part on real-time data and not entirely on retrospective data.

Non-transitory computer readable medium 57: An embodiment of any of non-transitory computer readable media 1-56, wherein the alerting a user with a user prompt on a user interface of a monitoring device includes rendering an ultrasonic pulse.

Non-transitory computer readable medium 58: An embodiment of any of non-transitory computer readable media 1-57, wherein the alerting a user with a user prompt on a user interface of a monitoring device includes, if the user ignores a first alerting, then causing a prompt on a second user interface of the monitoring device.

Non-transitory computer readable medium 59: An embodiment of non-transitory computer readable medium 58, wherein the monitoring device is a mobile cellular device, and wherein the second user interface includes an audio channel.

Non-transitory computer readable medium 60: An embodiment of non-transitory computer readable medium 59, wherein the prompt is an audible prompt and is played through the audio channel.

Non-transitory computer readable medium 61: An embodiment of non-transitory computer readable medium 58, wherein the monitoring device is a mobile cellular device, and wherein the second user interface includes a vibratory, haptic, or tactile rendering system.

Non-transitory computer readable medium 62: An embodiment of non-transitory computer readable medium 61, wherein the prompt is a vibratory prompt and is played through the vibratory, haptic, or tactile rendering system.

Non-transitory computer readable medium 63: An embodiment of non-transitory computer readable medium 62, wherein the monitoring device is a mobile cellular device, and wherein the second user interface includes an audio channel, wherein the prompt is an audible prompt and is played through the audio channel, and wherein the vibratory prompt is caused to be rendered if the audible prompt is not acknowledged by a user.

Non-transitory computer readable medium 64: An embodiment of any of non-transitory computer readable media 1-63, wherein the alerting a user with a user prompt on a user interface of a monitoring device includes, if the user ignores a first alerting, then causing a prompt on a second user interface of a second device.

Non-transitory computer readable medium 65: An embodiment of non-transitory computer readable medium 64, wherein the second device is a medicament delivery device, and where the prompt is audible or vibratory.

Non-transitory computer readable medium 66: An embodiment of any of non-transitory computer readable media 1-65, wherein the alerting a user with a user prompt on a user interface of a monitoring device includes rendering a haptic or vibratory signal.

Non-transitory computer readable medium 67: An embodiment of non-transitory computer readable medium 66, wherein the rendering is on the monitoring device.

Non-transitory computer readable medium 68: An embodiment of non-transitory computer readable medium 66, wherein the rendering is on a device in signal communication with the monitoring device.

Non-transitory computer readable medium 69: An embodiment of non-transitory computer readable medium 68, wherein the monitoring device is a smart phone and the device in signal communication with the monitoring device is a smart watch.

Non-transitory computer readable medium 70: An embodiment of non-transitory computer readable medium 66, wherein the rendering includes rendering the user prompt in a pattern, the pattern corresponding to the diabetic state warranting attention.

System 71: A system for providing smart alerts corresponding to diabetic states warranting user attention, comprising: a CGM application running on a mobile device, the CGM application configured to receive data from a sensor on an at least periodic or occasional basis and to calibrate and display glucose concentration data in clinical units; and a smart alerts application running as a subroutine within the CGM application or running as a parallel process with the CGM application on the mobile device and receiving data from the CGM application, the smart alerts application configured to perform the method contained on the medium of Non-transitory computer readable medium 1.

Non-transitory computer readable medium 72: A non-transitory computer readable medium, comprising instructions for causing a computing environment to perform a method of safely reducing alerting of users to diabetic states that require attention, the method comprising steps of: identifying a current or future diabetic state warranting attention, the identifying based at least partially on a glucose concentration value; determining if the identified diabetic state warranting attention is atypical for the user; if a result of the determining is that the identified diabetic state is atypical for the user, then alerting the user with a user prompt on a user interface of a monitoring device, the user prompt indicating the diabetic state warranting attention, whereby the user is only notified of the diabetic state warranting attention if the identified diabetic state is atypical for the user.

Non-transitory computer readable medium 73: An embodiment of non-transitory computer readable medium 72, wherein the determining if the identified diabetic state warranting attention is atypical for the user includes determining if the identified diabetic state includes a glucose trace following a pattern that is not typical of other patterns associated with the user.

Non-transitory computer readable medium 74: An embodiment of any of non-transitory computer readable media 72-73, wherein the determining if the identified diabetic state warranting attention is atypical for the user includes determining if the identified diabetic state includes a glucose trace following a trend that is not typical of other trends associated with the user.

Non-transitory computer readable medium 75: A non-transitory computer readable medium, comprising instructions for causing a computing environment to perform a method of prompting a user about a diabetic state that warrants attention, the computing environment in signal communication with a medicament delivery device, the user prompt optimized for effectiveness to the user at least in part by being reduced in number, the user prompt providing data relevant to treatment of the diabetic state warranting attention, the method comprising steps of: identifying a current or future diabetic state warranting attention, the identifying based at least partially on a glucose concentration value; performing a first estimating or predicting of a cognitive awareness of the user of the identified current or future diabetic state warranting attention; if the result of the first estimating or predicting is that the user is cognitively unaware of the identified current or future diabetic state warranting attention, then performing a second estimating or predicting of a computer awareness of the medicament delivery device of the identified current or future diabetic state warranting attention; if the result of the second estimating or predicting is that the medicament delivery device is unaware of the identified current or future diabetic state warranting attention, then alerting the user with a user prompt on a user interface of a monitoring device, the user prompt indicating the diabetic state warranting attention, whereby the user is only notified of the diabetic state warranting attention if and at a time that both the user and the medicament delivery device are unaware of the diabetic state warranting attention and that the notification is effective for the user.

Non-transitory computer readable medium 76: An embodiment of non-transitory computer readable medium 75, wherein the method further comprises steps of determining if the medicament delivery device is capable of treating the identified current or future diabetic state warranting attention, and if the result of the determining is that the medicament delivery device is incapable of treating the identified diabetic state, then alerting the user with the user prompt.

Non-transitory computer readable medium 77: An embodiment of any of non-transitory computer readable media 75-76, wherein the current or future diabetic state includes hypoglycemia, and wherein the medicament delivery device is an insulin delivery device, and further comprising shutting off or reducing activity of the insulin delivery device based on the diabetic state of hypoglycemia.

Non-transitory computer readable medium 78: An embodiment of non-transitory computer readable medium 77, wherein the shutting off or reducing activity occurs sooner in the case where the user is cognitively unaware of the hypoglycemia.

Non-transitory computer readable medium 79: An embodiment of any of non-transitory computer readable media 75-78, wherein the performing a first estimating or predicting is based at least partially on user interaction with the medicament delivery device.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) maybe implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, estimate or predict cognitive awareness of the user, and/or the like.

Although separate data storage and program memories are shown in FIG. 46, a variety of configurations may be used as well. For example, one or more memories may be used to provide storage space to support data processing and storage requirements at sensor electronics 12.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 46) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, WiFi, Bluetooth®, RFID, NFC, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer-readable medium may comprise non-transitory computer-readable medium (e.g., tangible media). In addition, in some aspects a computer-readable medium may comprise transitory computer-readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a"

or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The system and method may be fully implemented in any number of computing devices. Typically, instructions are laid out on computer readable media, generally non-transitory, and these instructions are sufficient to allow a processor in the computing device to implement the method of the aspects and embodiments. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated. For example, outputs may be stored on a memory chip, hard drive, flash drives, flash memory, optical media, magnetic media, or any other type of output. It should also be noted that the aspects and embodiments may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where smart alerts are contemplated, the plural inputs may allow plural users to input relevant data at the same time.

What is claimed is:

1. A non-transitory computer readable medium, comprising instructions for causing a computing environment to perform a method of dynamically adjusting or tuning user alerts based on a cognitive awareness determination, thereby providing data relevant to treatment of a diabetic state warranting attention, the method comprising steps of:
  identifying a current or future diabetic state warranting attention, the identifying based at least partially on a glucose concentration value;
  estimating or predicting a cognitive awareness of a user of the identified current or future diabetic state warranting attention, wherein the estimating or predicting the cognitive awareness is based on an established pattern of behavior of the user; and
  if the result of the estimating or predicting is that the user is cognitively unaware of the identified current or future diabetic state warranting attention, then alerting the user with a user prompt on a user interface of a monitoring device, the user prompt indicating the diabetic state warranting attention,
  whereby the user is only alerted of the diabetic state warranting attention if and at a time that the user is unaware of the diabetic state warranting attention and that the notification is effective for the user; and wherein the alerting the user with the user prompt on the user interface of the monitoring device includes, if the user ignores a first alerting, then causing a prompt on a second user interface of the monitoring device or causing a prompt on a second user interface of a second device.

2. The medium of claim 1, wherein the monitoring device is a mobile cellular device, and wherein the second user interface includes an audio channel.

3. The medium of claim 2, wherein the user prompt is an audible prompt and is played through the audio channel.

4. The medium of claim 1, wherein the monitoring device is a mobile cellular device, and wherein the second user interface includes a vibratory, haptic, or tactile rendering system.

5. The medium of claim 4, wherein the user prompt is a vibratory prompt and is played through the vibratory, haptic, or tactile rendering system.

6. The medium of claim 5, wherein the second user interface includes an audio channel, wherein the user prompt is an audible prompt and is played through the audio channel, and wherein the vibratory prompt is caused to be rendered if the audible prompt is not acknowledged by the user.

7. The medium of claim 1, wherein the second device is a medicament delivery device, and where the user prompt is audible or vibratory.

8. The medium of claim 1, wherein the alerting a user with a user prompt on a user interface of a monitoring device or on a second device includes rendering a haptic or vibratory signal.

9. The medium of claim 8, wherein the rendering is on the monitoring device.

10. The medium of claim 8, wherein the rendering is on the second device, the second device in signal communication with the monitoring device.

11. The medium of claim 10, wherein the monitoring device is a smart phone and the second device in signal communication with the monitoring device is a smart watch.

12. The medium of claim 8, wherein the rendering includes rendering the user prompt in a pattern, the pattern corresponding to the diabetic state warranting attention.

13. A non-transitory computer readable medium, comprising instructions for causing a computing environment to perform a method of safely reducing alerting of users to diabetic states that require attention, the method comprising steps of:

identifying a current or future diabetic state warranting attention, the identifying based at least partially on a glucose concentration value;

determining if the identified diabetic state warranting attention is atypical for the user;

if a result of the determining is that the identified diabetic state is atypical for the user, then alerting the user with a user prompt on a user interface of a monitoring device, the user prompt indicating the diabetic state warranting attention, whereby the user is only notified of the diabetic state warranting attention if the identified diabetic state is atypical for the user, wherein the identified diabetic state is atypical if it does not follow other patterns associated with the user.

14. The medium of claim 13, wherein the determining if the identified diabetic state warranting attention is atypical for the user includes determining if the identified diabetic state includes a glucose trace following a pattern that is not typical of other patterns associated with the user.

15. The medium of claim 13, wherein the determining if the identified diabetic state warranting attention is atypical for the user includes determining if the identified diabetic state includes a glucose trace following a trend that is not typical of other trends associated with the user.

16. A system for providing smart alerts corresponding to diabetic states warranting user attention, comprising:

a CGM application running on a mobile device, the CGM application configured to receive data from a sensor on an at least periodic or occasional basis and to calibrate and display glucose concentration data in clinical units; and a smart alerts application running as a subroutine within the CGM application or running as a parallel process with the CGM application on the mobile device and receiving data from the CGM application, the smart alerts application configured to perform the method contained on the medium of claim 1.

17. A system for providing smart alerts corresponding to diabetic states warranting user attention, comprising:

a CGM application running on a mobile device, the CGM application configured to receive data from a sensor on an at least periodic or occasional basis and to calibrate and display glucose concentration data in clinical units; and a smart alerts application running as a subroutine within the CGM application or running as a parallel process with the CGM application on the mobile device and receiving data from the CGM application, the smart alerts application configured to perform the method contained on the medium of claim 13.

* * * * *

UNITED STATES PATENT AND TRADEMARK OFFICE
CERTIFICATE OF CORRECTION

PATENT NO. : 10,406,287 B2
APPLICATION NO. : 16/029476
DATED : September 10, 2019
INVENTOR(S) : Anna Leigh Davis et al.

Page 1 of 1

It is certified that error appears in the above-identified patent and that said Letters Patent is hereby corrected as shown below:

On the Title Page

On page 3, Column 2, item (56), other publications, Line 3, delete "(Approved" and insert -- Approved --, therefor.

On page 4, Column 1, item (56), other publications, Line 11, delete "Imperiod Collegel" and insert -- Imperial College --, therefor.

On page 4, Column 1, item (56), other publications, Line 13, delete "Imperiod College" and insert -- Imperial College --, therefor.

In the Specification

In Column 7, Line 38, delete "claim" and insert -- claim. --, therefor.

In Column 10, Line 65, delete "tryptophan); andrenostenedione;" and insert -- tryptophan; androstenedione; --, therefor.

In Column 11, Line 14, delete "diptheria" and insert -- diphtheria --, therefor.

In Column 11, Line 21, delete "perioxidase;" and insert -- peroxidase; --, therefor.

In Column 11, Line 34, delete "Giardia duodenalisa," and insert -- Giardia duodenalis, --, therefor.

In Column 11, Line 43, delete "stomatis" and insert -- stomatitis --, therefor.

In Column 25, Line 49, delete "patterns)" and insert -- patterns). --, therefor.

In Column 33, Line 5, delete "(or" and insert -- or --, therefor.

Signed and Sealed this
Tenth Day of December, 2019

Andrei Iancu
*Director of the United States Patent and Trademark Office*